United States Patent [19]

Kurabayashi et al.

[11] Patent Number: 4,997,848

[45] Date of Patent: Mar. 5, 1991

[54] OCTAHYDRONAPHTHALENE OXIME DERIVATIVES FOR CHOLESTEROL SYNTHESIS INHIBITION

[75] Inventors: Masaaki Kurabayashi; Hiroshi Kogen; Hiroshi Kadokawa; Hideshi Kurihara; Kazuo Hasegawa; Masao Kuroda, all of Hiromachi, Japan

[73] Assignee: Sankyo Company, Limited, Tokyo, Japan

[21] Appl. No.: 261,739

[22] Filed: Oct. 21, 1988

[30] Foreign Application Priority Data

Oct. 27, 1987 [JP] Japan .................. 62-271512

[51] Int. Cl.$^5$ .................. A61K 31/36; C07D 319/06
[52] U.S. Cl. .................. 514/452; 549/373; 549/372; 549/292; 549/71; 549/484; 549/65; 549/66; 549/420; 549/279; 549/492; 548/201; 548/562; 548/561; 548/248; 548/236; 546/322; 546/326; 546/206; 544/149; 544/172; 544/335; 514/448; 514/365; 514/423; 514/350; 514/471; 514/424; 514/427; 514/445; 514/438; 514/256; 514/451; 514/378; 514/374; 514/319; 514/236; 514/514; 514/510; 560/256; 560/254; 560/255
[58] Field of Search .................. 549/373, 372, 292; 514/452

[56] References Cited

U.S. PATENT DOCUMENTS 3,983,140  9/1976  Endo .................. 549/292
4,604,472  8/1986  Ide .................. 549/292
4,733,003  3/1988  Ide .................. 549/292

Primary Examiner—Jane T. Fan

Attorney, Agent, or Firm—Frishauf, Holtz, Goodman & Woodward

[57] ABSTRACT

Compounds of formula (I):

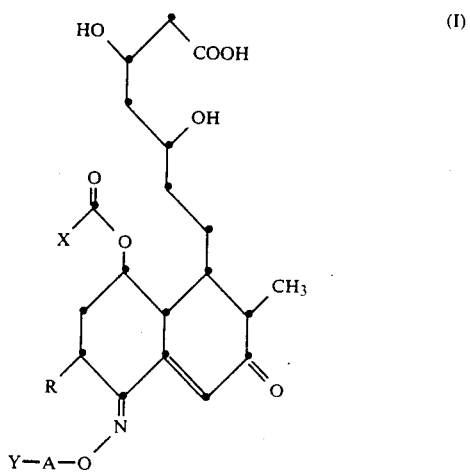

in which: R represents hydrogen, methyl of hydroxy; X represents an alkyl, alkenyl, cycloalkyl, aryl, aralkyl, or heterocyclic group; A represents a single bond, or an alkylene, alkenylene, alkynylene or alkadienylene group; Y represents hydrogen, or an aryl, cycloalkyl or heterocyclic group] have valuable antihypercholesteremic activities and may be used in the treatment of disorders arising from a blood cholesterol imbalance in humans and other animals.

24 Claims, No Drawings

OCTAHYDRONAPHTHALENE OXIME DERIVATIVES FOR CHOLESTEROL SYNTHESIS INHIBITION

BACKGROUND OF THE INVENTION

The present invention relates to a series of new octahydronaphthalene oxime derivatives, which are derivatives of the known compounds designated as Ml-236A, ML-236B, MB-530A and MB-530B. These compounds have the ability to inhibit the biosynthesis of cholesterol in vivo, and can therefore be used in the treatment and prophylaxis of hypercholesterolemia. The invention also provides processes for preparing these compounds and compositions and methods using them.

In recent years, a number of compounds having the essential skeletal structure of 3,5-dihydroxy-5-[2-(1-polyhydronaphthyl)ethyl]pentanoic acid have been discovered. The first of these, which were designated ML-236A and ML-236B, have the following formulae (i) and (ii), respectively:

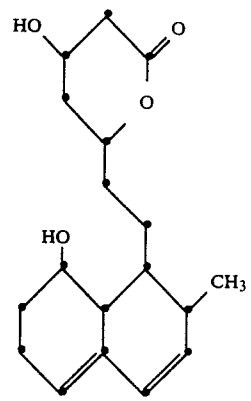

(i)

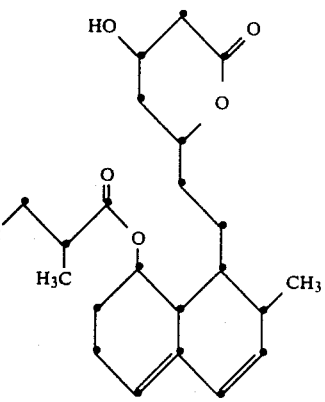

(ii)

and are disclosed in U.S. Pat. No. 3,983,140. These compounds can exist either in the form of a lactone (shown in the formulae above) or as a corresponding free hydroxy-carboxylic acid. They have been isolated and purified from the metabolic products of microorganisms of the genus Penicillium, especially Penicillium citrinum, a species of blue mold. They have been shown to inhibit the biosynthesis of cholesterol by enzymes or cultured cells separated from experimental animals by competing with the rate-limiting enzyme active in the biosynthesis of cholesterol, namely 3-hydroxy-3-methylglutaryl-coenzyme A reductase and, as a result, significantly reduce serum chloresterol levels of animals [Journal of Antibiotics 29, 1346 (1976)].

Subsequently, another compound having a similar structure was discovered in the metabolic products of a mold of the genus Monascus, especially Monascus ruber, and this compound, which is disclosed inter alia in U.K. Patent Specification No. 2 046 737A may be represented by the formula (iii):

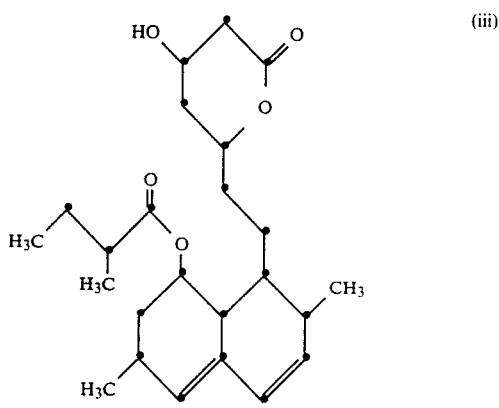

(iii)

This compound is referred to as "Monacolin K" in that United Kingdom Patent Specification, but has subsequently been referred to, and is herein referred to, as "MB-530B".

Subsequently, a similar compound, having similar antihypercholesteremic activity, was disclosed in U.K. Patent Specification No. 2 073 193A and was given the name "MB-530A; this compound may be represented by the formula (iv):

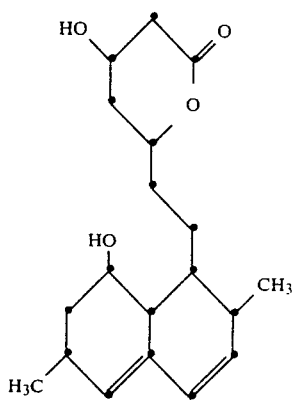

(iv)

Salts and esters of ML-236A, ML-236B, MB-530A and MB-530B are disclosed in U.K. Patent Specification No. 2 073 199, while further derivatives are disclosed in U.K. Patent Specification No. 2 075 013A.

The structure common to all of these compounds is shown below as formula (v), which also shows the numbering system employed herein to identify points of attachment and/or substitution:

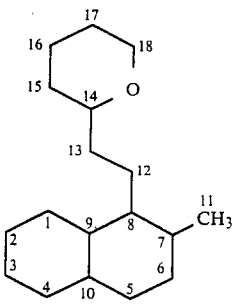

All of the above-mentioned compounds have double bonds between the 4- and 10- positions and the 5- and 6-positions. The hypothetical compounds having the same structure except that the double bonds are between the 3- and 4-positions and the 10- and 5- positions are named by adding the prefix "iso" before the name of the parent compound. Thus, the "iso" compounds corresponding to the compounds of formulae (i) and (iv) may be represented by the following formulae (vi) to (ix), respectively:

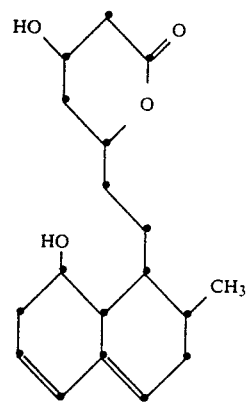
(vi)

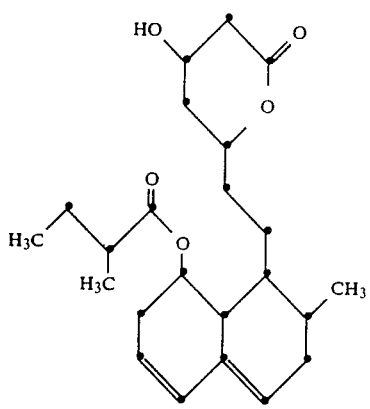
(vii)

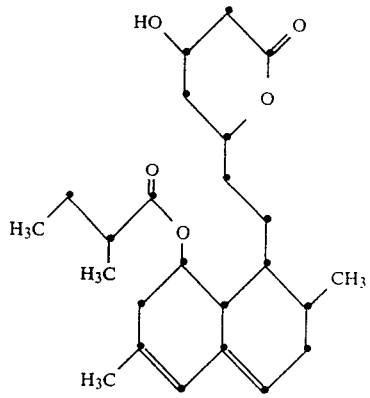
(viii)

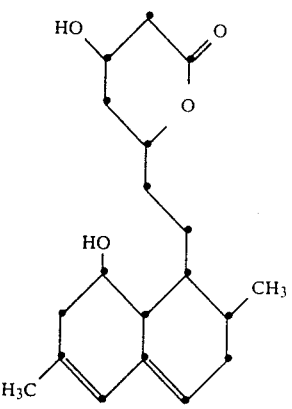
(ix)

As will be seen hereinafter, the nomenclature of the compounds of the present invention is based upon the names assigned to the compounds having the aforementioned formulae (i) to (iv) and (vi) to (ix).

We have now discovered a series of compounds which are derivatives of the ML-236 and MB-530 compounds: many of these new compounds have valuable antihypercholesteremic activity, the activities of some of these compounds being at least an order of magnitude greater than the activities of the known compounds.

Various derivatives of the primary compounds described above have been disclosed in the prior art. The prior art compounds believed to be closest structurally to the compounds of the present invention are disclosed in European Patent Publication No. 76 601, where there are disclosed ML-236A, ML-236B, MB-530A and MB-530B derivatives having a hydroxyimino group at the 4-position. These compounds differ from those of the present invention in the nature of the groups at the 4-and/or 3- positions, and the compounds of the present invention have a substantially better cholesterol synthesis inhibitory activity than do these prior art compounds.

BRIEF SUMMARY OF INVENTION

Accordingly, the present invention provides compounds of formula (I):

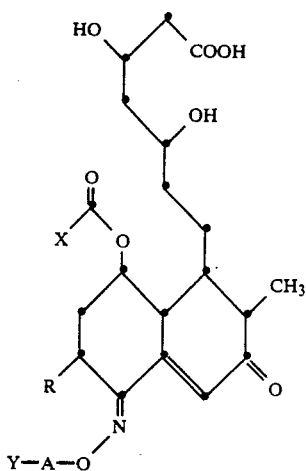

(I)

in which:
R represents a hydrogen atom, a methyl group or a hydroxy group;
X represents a $C_1-C_{10}$ alkyl group, a $C_3-C_{10}$ alkenyl group, a $C_3-C_{10}$ cycloalkyl group, a $C_6-C_{10}$ aryl group, a $C_7-C_{12}$ aralkyl group, or a heterocyclic group having 5 or 6 ring atoms of which from 1 to 3 are hetero-atoms selected from the group consisting of nitrogen, oxygen and sulfur atoms, said alkyl and alkenyl groups being unsubstituted or having at least one substituent selected from the group consisting of substituents (a), defined below, and said cycloaklyl, aryl, aralkyl and heterocyclic groups being unsubstituted or having at least one substituent selected from the group consisting of substituents (b), defined below;
A represents a single bond, a $C_1-C_{10}$ alkylene group, a $C_3-C_{10}$ alkenylene group, a $C_3-C_{10}$ alkynylene group or a $C_5-C_{10}$ alkadienylene group, said alkylene, alkenylene, alknynlene and alkadienylene groups being unsubstituted or having at lest one substituent selected from the group consisting of substituents (c), defined below;
Y represents a hydrogen atom, a $C_6-C_{14}$ aryl group, a $C_3-C_{10}$ cycloalkyl group, a heterocyclic group having 5 or 6 ring atoms of which from 1 to 3 are hetero-atoms selected from the group consisting of nitrogen, oxygen and sulfur hetero-atoms or a heterocyclic group having 5 or 6 ring atoms of which from 1 to 3 are hetero-atoms selected from the group consisting of nitrogen, oxygen and sulfur hetero-atoms and being fused to a benzene ring, said aryl, cycloalkyl and heterocyclic groups being unsubstituted or having at least one substituent selected from the group consisting of substituents (d), defined below;
provided that, where X represents a 1-methylpropyl group and -A-Y represents a hydrogen atom or an alkyl group, then R represents a hydroxy group;

substituents (a):
halogen atoms, hydroxy groups, $C_1-C_4$ alkoxy groups, $C_2-C_5$ aliphatic carboxylic acyloxy groups, amino groups, carboxy groups and protected carboxy groups;

substituents (b):
halogen atoms, hydroxy groups, $C_1-C_4$ alkoxy groups, $C_2-C_5$ aliphatic carboxylic acyloxy groups, amino groups, carboxy groups and protected carboxy groups, $C_1-C_5$ alkyl groups and $C_1-C_5$ haloalkyl groups;

substituents (c):
halogen atoms, hydroxy groups, $C_1-C_4$ alkoxy groups, $C_6-C_{14}$ aryloxy groups, $C_7-C_9$ aralkyloxy groups, $C_2-C_5$ aliphatic carboxylic acyloxy groups, $C_7-C_{15}$ aromatic carboxylic acyloxy groups, amino groups, $C_1-C_4$ alkylamino groups, dialkylamino groups in which each alkyl group is $C_1-C_4$, $C_6-C_{14}$ arylamino groups, diarylamino groups in which each aryl group is $C_6-C_{14}$, $C_7-C_9$ aralkylamino groups, diaralkylamino groups in which each aralkyl group is $C_7-C_9$, $C_2-C_5$ aliphatic carboxylic acylamino groups, $C_7-C_{15}$ aromatic carboxylic acylamino groups, carboxy groups and protected carboxy groups, wherein the aryl groups of said aryloxy, aralkyloxy, aromatic carboxylic acyloxy, arylamino, diarylamino, aralkylamino, diaralkylamino and aromatic carboxylic acylamino groups are unsubstituted or have at least one substituent selected from the group consisting of substituents (e), defined below;

substituents (d):
halogen atoms, hydroxy groups, $C_1-C_4$ alkoxy groups, $C_6-C_{14}$ aryloxy groups, $C_7-C_9$ aralkyloxy groups, $C_2-C_5$ aliphatic carboxylic acyloxy groups, $C_7-C_{15}$ aromatic carboxylic acyloxy groups, mercapto groups, $C_1-C_4$ alkylthio groups, $C_6-C_{14}$ arylthio groups, $C_7-C_9$ aralkylthio groups, amino groups, $C_1-C_4$ alkylamino groups, dialkylamino groups in which each alkyl group is $C_1-C_4$, $C_6-C_{14}$ arylamino groups, diarylamino groups in which each aryl group is $C_6-C_{14}$, $C_7-C_9$ aralkylamino groups, diaralkylamino groups in which each aralkyl group is $C_7-C_9$, $C_2-C_5$ aliphatic carboxylic acylamino groups, $C_7-C_{15}$ aromatic carboxylic acylamino groups, nitro groups, cyano groups, carboxy groups, protected carboxy groups, $C_1-C_5$ alkyl groups and $C_1-C_5$ alkyl groups having at least one substituent selected from the group consisting of substituents (f), defined below, wherein the aryl groups of said aryloxy, aralkyloxy, aromatic carboxylic acyloxy, arylthio, aralkylthio, arylamino, diarylamino, aralkylamino, diaralkylamino and aromatic carboxylic acylamino groups are unsubstituted or have at least one substituent selected from the group consisting of substituents (e), defined below;

substituents (e):
$C_1-C_4$ alkyl groups, hydroxy groups, halogen atoms, $C_1-C_4$ alkoxy groups, carboxy groups, protected carboxy groups and amino groups;

substituents (f):
halogen atoms, hydroxy groups and $C_2-C_5$ aliphatic carboxylic acyloxy groups;

pharmaceutically acceptable salts and esters thereof and the corresponding ring-closed lactones.

The invention also provides a pharmaceutical composition comprising an agent for inhibiting cholesterol biosynthesis in admixture with a pharmaceutically acceptable carrier or diluent, wherein said agent is selected from the group consisting of compounds of formula (I), as defined above, and pharmaceutically acceptable salts, esters and lactones thereof.

The invention still further provides a method of treating a mammal suffering from a disorder arising from a blood cholesterol imbalance, which comprises administering to said mammal an effective amount of an agent inhibiting cholesterol biosynthesis, wherein said agent is selected from the group consisting of compounds of formula (I), as defined above, and pharmaceutically acceptable salts, esters and lactones thereof.

The invention also provides processes for preparing the compounds of the present invention, which are described in more detail hereinafter.

DETAILED DESCRIPTION OF INVENTION

For the avoidance of doubt, the lactone compounds of the present invention have the following formula (II):

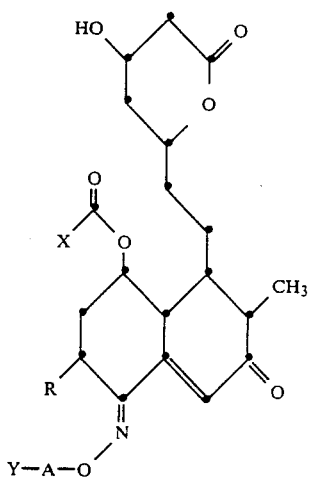

(II)

in which R, X, A and Y are as defined above.

In the above formulae (I) and (II), when X represents an alkyl group, it may be a straight or branched chain alkyl group having from 1 to 10 carbon atoms, preferably from 1 to 7 carbon atoms, for example a methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 2,2-dimethylpropyl, 1,2-dimethylpropyl, 1-ethylpropyl, hexyl, 1-methylpentyl, 2-methylpentyl, 1,1-dimethylbutyl, 1,3-dimethylbutyl, 1-ethylbutyl, 2-ethylbutyl, 1-methyl-1-ethylpropyl, heptyl, 1-methyl-1-ethylbutyl, 2-methyl-2-ethylbutyl, octyl, 1-methylheptyl, 2-ethylhexyl, 1,1,3,3-tetramethylbutyl, nonyl, decyl or 3,7-dimethyloctyl group.

When X represents an alkenyl group, it may be a straight or branched chain alkenyl group having from 3 to 10 carbon atoms, preferably from 3 to 7 carbon atoms, for example a 1-propenyl, 2-propenyl, 2-butenyl, 3-butenyl, 2-methyl-2-propenyl, 2-pentenyl, 3-pentenyl, 4-hexenyl, 5-heptenyl, 2-octenyl, 4-octenyl, 2-nonenyl, 3-nonenyl, 4-nonenyl, 3-decenyl or 5-decenyl group.

When X represents a cycloalkyl group, it may be a cycloalkyl group having from 3 to 10 carbon atoms, preferably from 3 to 7 carbon atoms, and may be monocyclic or polycyclic, e.g. bicyclic, group, for example a cyclopropyl, cyclobutyl, cyclopentyl, cyclohexyl, cycloheptyl, cyclooctyl, cyclononyl or cyclodecyl group.

When X represents an aryl group, it may have from 6 to 10 carbon atoms, and examples include the phenyl, 1-naphthyl and 2-naphthyl groups, preferably the phenyl group.

When X represents an aralkyl group, it may have in total form 7 to 12 carbon atoms, preferably from 7 to 9 carbon atoms; the alkyl part thereof preferably has from 1 to 6 carbon atoms, more preferably from 1 to 3 carbon atoms, most preferably 1 or 2 carbon atoms; and the aryl part preferably has from 6 to 10 carbon atoms, more preferably 6 or 10 carbon atoms, and is most preferably the phenyl group. Examples of such groups include the benzyl, 1-methylbenzyl, phenethyl, 3-phenylpropyl, 1,1-dimethylbenzyl, 4-phenylbutyl, 1-methyl-3-phenylpropyl, 5-phenylpentyl and 6-phenylhexyl groups.

When X represents a heterocyclic group, it contains 5 or 6 ring atoms, of which from 1 to 3 are oxygen atoms and/or sulfur atoms and/or nitrogen atoms. It may be a fully unsaturated heterocyclic group and examples of such groups include the 2-furyl, 3-furyl, 2-thienyl, 3-thienyl, 2-thiazolyl, 4-thiazolyl, 1-pyrrolyl, 2-pyrrolyl, 3-pyridyl, 4-pyridyl, 2-pyrimidinyl, 5-pyrimidinyl, 2-pyranyl, 4-pyranyl, 3-isoxazolyl, 5-isoxazolyl, 2-oxazolyl and 5-oxazolyl groups. Alternatively, it may be a a wholly or partially saturated group, for example a 2-tetrahydrofuryl, 3-tetrahydrofuryl, 2-tetrahydrothienyl, 3-tetrahydrothienyl, 1-pyrrolidinyl, 3-pyrrolidinyl, 2-piperazyl, piperidino, 2-piperidyl, morpholino, 3-morpholinyl, 2-tetrahydropyranyl, 4-tetrahydropyranyl, 1,4-dioxan-2-yl, 1,3-dioxan-4-yl or 1,3-dioxan-5-yl group. Of these, we prefer the 5- and 6-membered unsaturated heterocyclic groups containing from 1 to 3 oxygen atoms and/or sulfur atoms and/or nitrogen atoms.

When X represents an alkyl group or an alkenyl group, such groups may be substituted or unsubstituted and, if substituted, the substituents are selected from the group consisting of substituents (a), defined above. There is, in principle, no restriction on the number of substituents on any alkyl or alkenyl group represented by X, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms;

halogen atoms, such as the chlorine, bromine and fluorine atoms;

the hydroxy group;

$C_1$-$C_4$ alkoxy groups, such as the methoxy and ethoxy groups;

$C_2$-$C_5$ aliphatic carboxylic acyloxy groups, especially $C_2$-$C_5$ alkanoyloxy groups, such as the acetoxy, propionyloxy and butyryloxy groups;

the amino group;

the carboxy group;

protected carboxy groups in which the protecting group is preferably as defined below.

Protecting groups for carboxy groups are well known in this field and the skilled man would have no difficulty in determining what groups may be used. By way of illustration only, examples of such groups include lower (e.g. $C_1$-$C_4$) alkyl groups, to form a protected group such as the methoxycarbonyl, ethoxycarbonyl or t-butoxycarbonyl group; aralkyl groups (preferably as defined above as such groups which may be represented by X), to form a protected group, such as the benzyloxycarbonyl, diphenylmethoxycarbonyl, 4-nitrobenzyloxycarbonyl or 2-nitrobenzyloxycarbonyl group; lower (e.g. $C_2$-$C_4$) alkenyl and haloalkenyl groups, to form a protected group, such as the allyloxycarbonyl or 2-chloroallyloxycarbonyl group; lower (e.g. $C_1$-$C_4$) haloalkyl groups, to form a protected group such as the 2,2,2-trichloroethoxycarbonyl or 2,2,2-tribromoethoxycarbonyl group; and tri(substituted)silylalkyl groups in which the substituents are preferably $C_1$–$C_4$ alkyl groups and/or phenyl groups and in which the alkyl group is $C_1$–$C_4$, to form a protected group such as the 2-(trimethylsilyl)ethoxycarbonyl group.

Of these substituents, the most preferred are the halogen atoms, the hydroxy group, $C_2$–$C_5$ aliphatic carboxylic acyloxy groups, the carboxy group, and protected carboxy groups; and most preferred of all are the halogen atoms and the carboxy group.

When X represents a cycloalkyl group, an aryl group, an aralkyl group or a heterocyclic group, such groups may be substituted or unsubstituted and, if substituted, the substituents are selected from the group consisting of substituents (b), defined above. There is, in principle, no restriction on the number of substituents on any cycloalkyl, aryl, aralkyl or heterocyclic group represented by X, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms:

halogen atoms, such as the chlorine, bromine and fluorine atoms;

the hydroxy group;

$C_1$–$C_4$ alkoxy groups, such as the methoxy and ethoxy groups;

$C_2$–$C_5$ aliphatic carboxylic acyloxy groups, especially $C_2$–$C_5$ alkanoyloxy groups, such as the acetoxy, propionyloxy and butyryloxy groups;

the amino group;

the carboxy group;

protected carboxy groups in which the protecting group is preferably as defined above for the protected groups of substituents (a), such s the methoxycarbonyl, ethoxycarbonyl, t-butoxycarbonyl, benzyloxycarbonyl, diphenylmethoxycarbonyl, 4-nitrobenzyloxycarbonyl, 2-nitrobenzyloxycarbonyl, allyloxycarbonyl, 2-chloroallyloxycarbonyl, 2,2,2-trichloroethoxycarbonyl, 2,2,2-tribromoethoxycarbonyl and 2-(trimethylsilyl)ethyloxycarbonyl groups;

$C_1$–$C_5$ alkyl groups, such as the methol, ethyl, propyl, isopropyl, butyl and pentyl groups; and halogen-substituted $C_1$–$C_5$ alkyl groups, such as the trifluoromethyl group.

Of these substituents, the most preferred are the halogen atoms, the hydroxy group, $C_1$–$C_4$ alkoxy groups, $C_2$–$C_5$ aliphatic carboxylic acyloxy groups, $C_1$–$C_5$ alkyl groups and halogen substituted $C_1$–$C_5$ alkyl groups, and the most preferred of al are the halogen atoms and halogen-substituted $C_1$–$C_5$ alkyl groups.

When A represents a divalent saturated acyclic hydrocarbon group, it may be an alkylene group having from 1 to 10 carbon atoms, preferably form 1 to 5 carbon atoms. The group may be a straight or branched chain group, and the two "free" valences may be on the same carbon atom (in which case, the group is sometimes known as an "alkylidene"0 group) or they may be on different carbon atoms. Examples of such groups include the methylene, ethylidene, ethylene, 1-methylethylene trimethylene, 1,2-dimethylethylene, 1-ethylethylene, 1-methyltrimethylene, 2-methyltrimethylene, tetramethylene, 1-propylethylene, 1-ethyl-2-methylethylene, 1-ethyltrimethylene, 2-ethyltrimethylene, 1,3-dimethyltrimethylene, 1-methyltetramethylene, 2-methyltetramethylene, pentamethylene, 1-butylethylene, 1-methyl-2-propylethylene, 1,2-diethylethylene, 1-methyl-1-propylethylene, 2-propyltriethylene, 1-ethyl-3-methyltrimethylene, 1-ethyltetramethylene, 2-ethyltetramethylene, 1,3-dimethyltetramethylene, 1-methylpentamethylene, 2-methylpentamethylene, 3-methylpentamethylene, hexamethylene, 1-pentylethylene, 1-butyl-2-methylethylene, 1-ethyl-2-propylethylene, 1-butyltrimethylene, 2; butyltrimethylene, 1,3-diethyltrimethylene, 1-methyl-3-propyltrimethylene, 1-propyltetramethylene, 2-propyltetramethylene, 1-ethyl-4-methyltetramethylene, 3-ethyl-1methyltetramethylene, 1-ethylpentamethylene, 3-ethylpentamethylene, 1,3-dimethylpentamethylene, 1-methylhexamethylene, 3-methylhexamethylene, heptamethylene, 1-hexylethylene, 1-methyl-2-pentylethylene, 1-butyl-2-ethylethylene, 1,2-dipropylethylene, 1-pentyltrimethylene, 2-pentyltrimethylene, 1-butyl-3-methyltrimethylene, 1-butyl-2-methyltrimethylene, 1-ethyl-3-propyltrimethylene, 1,2-dimethyl-3-propyltrimethylene, 1-butyltetramethylene, 1-methyl-4-propyltetramethylene, 1-propylpentamethylene, 3-propylpentamethylene, 2-ethyl-4-methylpentamethylene, 1-ethylhexamethylene, 3-ethylhexamethylene, 1,3-dimethylhexamethylene, 1-methylheptamethylene, 4-methylheptamethylene, octamethylene and 2,6-dimethyloctamethylene.

When A represents a divalent unsaturated acyclic hydrocarbon group, it may be an alkenylene group having from 3 to 10 carbon atoms, preferably from 3 to 7 carbon atoms, and most preferably from 3 to 5 carbon atoms. The group may be a straight or branched chain group, and the two "free" valences may be on the same carbon atom or they may be on different carbon atoms. Examples of such groups include the 2-propenylene, 2-methyl-2-propenylene, 2-butenylene, 3-butenylene, 2-pentenylene, 4-pentenylene, 2-methyl-2-butenylene, 2-hexenylene, 2-heptenylene, 3-methyl-2-hexenylene, 3-ethyl-2-pentenylene, 2-methyl-3-hexenylene, 2-octenylene, 4-octenylene, 3-methyl-2-heptenylene, 3,5-dimethyl-2-hexenylene, 2-nonenylene, 3-methyl-2-octenylene, 3,5-dimethyl-3-heptenylene, 2-decenylene and 3,7-dimethyl-2-octenylene groups. Alternatively, it may be an alkadienylene group having from 5 to 10 carbon atoms, preferably from 5 to 8 carbon atoms. The group may be a straight or branched chain group, and the two "free" valences may be on the same carbon atom or they may be on different carbon atoms. Examples of such groups include the 2,4-pentadienylene, 2,4-hexadienylene, 4-methyl-2,4-pentadienylene, 2,4-heptadienylene, 2,6-heptadienylene, 3-methyl-2,4-hexadienylene, 2,6-octadienylene, 3-methyl-2,6-heptadienylene, 2-methyl-2,4-heptadienylene, 2,8-nonadienylene, 3-methyl-2,6-octadienylene, 2,6-decadienylene, 2,9-decadienylene and 3,7-dimethyl-2,6-octadienylene groups. It may also be an alkynylene group having from 3 to 10 carbon atoms, preferably from 3 to 5 carbon atoms. The group may be a straight or branched chain group, and the two "free" valences may be on the same carbon atom or they may be on different carbon atoms. Examples of such groups include the 2-propynylene, 2-butynylene, 2-pentynylene, 2-hexynylene, 4-methyl-2-pentynylene, 2-heptynylene, 3-octynylene and 4-decynylene groups.

These divalent saturated or unsaturated acyclic hydrocarbon groups may be substituted or unsubstituted and, if substituted, the substituents are selected from the group consisting of substituents (c), defined above. There is, in principle, no restriction on the number of substituents on any such group, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms:

halogen atoms, such as the chlorine, bromine and fluorine atoms;

the hydroxy group; $C_1$–$C_4$ alkoxy groups, such as the methoxy and ethoxy groups;

$C_6$–$C_{14}$ aryloxy groups, such as the phenoxy, 1-naphthyloxy or 2-naphthyloxy group, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the 4-tolyloxy, 4-hydroxyphenoxy, 4-chlorophenoxy, 4-fluorophenoxy, 4-methoxyphenoxy, 4-carboxyphenoxy, 4-methoxycarbonylphenoxy and 4-aminophenoxy groups;

$C_7$–$C_9$ aralkyloxy groups in which the aryl part is preferably a phenyl group and the alkyl part is preferably $C_1$–$C_3$, such as the benzyloxy or phenethyloxy groups, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the 4-methylbenzyloxy, 4-hydroxybenzyloxy, 4-chlorobenzyloxy, 4-methoxybenzyloxy, 4-carboxybenzyloxy, 4-methoxycarbonylbenzyloxy and 4-aminobenzyloxy groups;

$C_2$–$C_5$ aliphatic carboxylic acyloxy groups, especially $C_2$–$C_5$ alkanoyloxy groups, such as the acetoxy, propionyloxy and butyryloxy groups;

$C_7$–$C_{15}$ aromatic carboxylic acyloxy groups, especially benzoyloxy and naphthoyloxy groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the benzoyloxy, 1-naphthoyloxy, 2-naphthoyloxy, 4-methylbenzoyloxy, 2-hydroxybenzoyloxy, 4-hydroxybenzopyloxy, 4-chlorobenzoyloxy, 4-methoxybenzoyloxy, 4-carboxybenzoyloxy, 4-methoxycarbonylbenzoyloxy and 4-aminobenzoyloxy groups;

the amino group;

mono- and di-$C_1$–$C_4$ alkyl substituted amino groups, such as the methylamino, dimethylamino and diethylamino groups;

mono- and di-$C_6$–$C_{14}$ aryl substituted amino groups, especially phenylamino and naphthylamino groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl hydroxy groups, halogen atoms, $C_1$–$C_4$ alkoxy groups, carboxy groups, protected carboxy groups, e.g. as exemplified above in relation to substituents (a), and amino groups; examples of such groups include the phenylamino, 1-naphthylamino, 2-naphthylamino, 4-tolylamino, 4-hydroxyphenylamino, 4-chlorophenylamino, 4-methoxyphenylamino, 4-carboxyphenylamino, 4-methoxycarbonylphenylamino and 4-aminophenylamino groups;

mono- and di-$C_7$–$C_9$ aralkyl substituted amino groups, especially benzylamino and phenethylamino groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the benzylamino, phenethylamino, 4-methylbenzylamino, 4-hydroxybenzylamino, 4-chlorobenzylamino, 4-methoxybenzylamino, 4-carboxybenzylamino, 4-methoxycarbonylbenzylamino and 4-aminobenzylamino groups;

$C_2$–$C_5$ aliphatic carboxylic acyl substituted amino groups, especially $C_2$–$C_5$ alkanoylamino groups, such as the acetamido, propionamido and butyramido groups;

$C_7$–$C_{15}$ aromatic carboxylic acyl substituted amino groups, especially benzamido and naphthoylamido groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the benzamido, naphthoylamido, 4-methylbenzamido, 4-hydroxybenzamido, 4-chlorobenzamido, 4-methoxybenzamido, 4-carboxybenzamido, 4-methoxycarbonylbenzamido and 4-aminobenzamido groups;

the carboxy group; and protected carboxy groups in which the protecting group is preferably as defined above for the protected groups of substituents (a), such as the methoxycarbonyl, ethoxycarbonyl, t-butoxycarbonyl, benzyloxycarbonyl, diphenylmethoxycarbonyl, 4-nitrobenzyloxycarbonyl, 2-nitrobenzyloxycarbonyl, allyloxycarbonyl, 2-chloroallyloxycarbonyl, 2,2,2-trichloroethoxycarbonyl, 2,2,2-tribromoethoxycarbonyl and 2-(trimethylsilyl)ethyloxycarbonyl groups.

Of these substituents, the preferred ones are:

halogen atoms; hydroxy groups; $C_1$–$C_4$ alkoxy groups; $C_6$–$C_{14}$ aryloxy groups (wherein the aryl moieties may have from 1 to 3 substituents, which may be the same or different from one another, such as $C_1$–$C_4$ alkyl, hydroxy, halogen, $C_1$–$C_4$ alkoxy, carboxy, protected carboxy and amino); $C_2$–$C_5$ aliphatic carboxylic acyloxy groups; amino groups; mono-and di-$C_1$–$C_4$ alkyl substituted amino groups; $C_2$–$C_5$ aliphatic carboxylic acyl substituted amino groups, $C_7$–$C_{15}$ aromatic carboxylic acyl substituted amino groups (wherein the aryl moieties may have from 1 to 3 substituents which may be the same or different from one another, such as $C_1$–$C_4$ alkyl, hydroxy, halogen, $C_1$–$C_4$ alkoxy, carboxy, protected carboxy and amino); carboxy groups; and protected carboxy groups;

more preferably;

halogen atoms; hydroxy groups, $C_1$–$C_4$ alkoxy groups; amino groups; mono- or di-$C_1$–$C_4$ alkyl substituted amino groups; and $C_2$–$C_5$ aliphatic carboxylic acryl substituted amino groups; and most preferably;

hydroxy groups and $C_1$–$C_4$ alkoxy groups.

When Y represents an aryl group, it may be an aryl group having from 6 to 14 carbon atoms, preferably from 6 to 10 carbon atoms, and examples include the phenyl, 1-naphthyl, 2-naphthyl, anthracenyl and phenanthrenyl groups, which may be substituted or unsubstituted, and, if substituted, have at least one substituent selected from the group consisting of substituents (d), defined above and exemplified below.

When Y represents a cycloalkyl group, it may be a monocyclic or polycyclic (e.g. cicyclic or tricyclic) cycloalkyl group (which term, as used herein, includes the terpenyl hydrocarbon groups) having from 3 to 10 carbon atoms, preferably from 3 to 8 carbon atoms, most preferably from 5 to 7 carbon atoms, and examples include the cyclopropyl, cyclobutyl, cyclopentyl, cyclohexyl, cycloheptyl, cyclooctyl, cyclononyl, cyclodecyl, adamantyl, pinanyl, bornyl and menthyl groups, which may be substituted or unsubstituted, and, if substituted, have at least one substituent selected from the group consisting of substituents (d), defined above and exemplified below.

When Y represents a heterocyclic group, it may be a simple 5- or 6-membered unsaturated heterocyclic group containing from 1 to 3 oxygen atoms and/or sulfur atoms and/or nitrogen atoms, which may be substituted or unsubstituted. Examples of the unsubstituted groups include the 2-furyl, 3-furyl, 2-thienyl, 3-thienyl, 2-thiazolyl, 4-thiazolyl, 1-pyrrolyl, 2-pyrrolyl, 3-pyridyl, 4-pyridyl, 2-pyrimidinyl, 5-pyrimidinyl, 2-pyranyl, 4-pyranyl, 3-isoxazolyl, 5-isoxazolyl, 2-oxazolyl and 5-oxazolyl groups.

Alternatively, it may be a 5- or 6-membered saturated heterocyclic group containing from 1 to 3 oxygen atoms and/or sulfur atoms and/or nitrogen atoms, which may be substituted or unsubstituted. Examples of the unsubstituted groups include the 2-tetrahydrofuryl, 3-tetrahydrofuryl, 2-tetrahydrothienyl, 3-tetrahydrothienyl, 1-pyrrolidinyl, 3-pyrrolidinyl, 2-piperazyl, piperidino, 2-piperidyl, morpholino, 3-morpholinyl, 2-tetrahydropyranyl, 4-tetrahydropyranyl, 1,4-dioxan-2-yl, 1,3-dioxan-4-yl and 1,3-dioxan-5-yl groups.

Alternatively, it may be a condensed heterocyclic group in which a 5- o 6- membered saturated heterocyclic group containing from 1 to 3 oxygen atoms and/or sulfur atoms and/or nitrogen atoms is condensed with a benzene ring. The heterocyclic part of such a ring system may be fully unsaturated or partially unsaturated, and the group may be substituted or unsubstituted. Examples of the unsubstituted groups include the 2-benzofuranyl, 2-2H-chromenyl, 2-benzothienyl, 2-indolinyl, 3-indolinyl, 2-dihydrobenzofuranyl, 2-chromanyl, 1,4-benzodioxan-2-yl, 4-quinolyl and 1-isoquinolyl groups.

These heterocyclic groups are preferably 5- or 6-membered unsaturated, saturated or condensed heterocyclic groups having 1 or 2 oxygen atoms and/or nitrogen atoms, most suitably 5- or 6-membered saturated or unsaturated heterocyclic groups containing 1 or 2 oxygen atoms and/or nitrogen atoms. Any of these heterocyclic groups may be substituted or unsubstituted, and, if substituted, they have at least one substituent selected from the group consisting of substituents (d), defined above and exemplified below.

These aryl, cycloalkyl and heterocyclic groups represented by Y may be substituted or unsubstituted and, if substituted, the substituents are selected from the group consisting of substituents (d), defined above. There is, in principle, no restriction on the number of substituents on any such group, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms:

halogen atoms, such as the chlorine, bromine and fluorine atoms;

the hydroxy group;

$C_1$–$C_4$ alkoxy groups, such as the methoxy and ethoxy groups;

$C_6$–$C_{14}$ aryloxy groups, such as the phenoxy, 1-naphthyloxy and 2-naphthyloxy groups, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms $C_1$–$C_4$ alkoxy groups, carboxy groups, protected carboxy groups, e.g. as exemplified above in relation to substituents (a), and amino groups; examples of such groups include the 4-tolyloxy, 4-hydroxyphenoxy, 4-chlorophenoxy, 4-fluorophenoxy, 2-methoxyphenoxy, 4-methoxyphenoxy, 4-carboxyphenoxy, 4-methoxycarbonylphenoxy and 4-aminophenoxy groups;

$C_7$–$C_9$ aralkyloxy groups in which the aryl part is preferably a phenyl group and the alkyl part is preferably $C_1$–$C_3$, such as the benzyloxy and phenethyloxy groups, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the 4-methylbenzyloxy, 4-hydroxybenzyloxy, 4-chlorobenzyloxy, 4-methoxybenzyloxy, 4-carboxybenzyloxy, 4-methoxycarbonylbenzyloxy and 4-aminobenzyloxy groups;

$C_2$–$C_5$ aliphatic carboxylic acyloxy groups, especially $C_2$–$C_5$ alkanoyloxy groups, such as the acetoxy, propionyloxy and butyryloxy groups;

$C_7$–$C_{15}$ aromatic carboxylic acyloxy groups, especially benzoyloxy and naphthoyloxy groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the benzoyloxy, 1-naphthoyloxy, 2-naphthoyloxy, 4-methylbenzoyloxy, 2-hydroxybenzoyloxy, 4-hydroxybenzoyloxy, 4-chlorobenzoyloxy, 4-methoxybenzoyloxy, 4-carboxybenzoyloxy, 4-methoxycarbonylbenzoyloxy and 4-aminobenzoyloxy groups; $C_1$–$C_4$ alkylthio groups, such as the methylthio and ethylthio groups;

$C_6$–$C_{14}$ arylthio groups, especially phenylthio and naphthylthio groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the phenylthio, 1-naphthylthio, 2-naphthylthio, 4-tolylthio, 4-hydroxyphenylthio, 4-chlorophenylthio, 4-methoxyphenylthio, 4-carboxyphenylthio, 4-methoxycarbonylphenylthio and 4-aminolphenylthio groups;

$C_7$–$C_9$ aralkylthio groups, especially benzylthio and phenethylthio groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the benzylthio, phenethylthio, 4-methylbenzylthio, 4-hydroxybenzylthio, 4-chlorobenzylthio, 4-methoxybenzylthio, 4-carboxybenzylthio, 4-methoxycarbonylbenzylthio and 4-aminobenzylthio groups;

the amino group;

mono- and di-$C_1$–$C_4$ alkyl substituted amino groups, such as the methylamino, dimethylamino and diethylamino groups;

mono- and di-$C_6$–$C_{14}$ aryl substituted amino groups, especially phenylamino and naphthylamino groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl hydroxy groups, halogen atoms, $C_1$–$C_4$ alkoxy groups, carboxy groups, protected carboxy groups, e.g. as exemplified above in relation to substituents (a), and amino groups; examples of such groups include the phenylamino, 1-naphthylamino, 2-naphthylamino, 2-tolylamino, 4-tolylamino, 4-hydroxyphenylamino, 4-chlorophenylamino, 4-methoxyphenylamino, 4-carboxyphenylamino, 4-methoxycarbonylphenylamino and 4-aminophenylamino groups;

mono- and di-$C_7$–$C_9$ aralkyl substituted amino groups, especially benzylamino and phenethylamino groups which are substituted or unsubstituted, and wherein the aryl moieties may be unsubstituted or have, for example, from 1 to 5 substituents, preferably from 1 to 3 substituents, selected from the group consisting of substituents (e), which may be the same or different from one another such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the benzylamino, phenethylamino, 4-methylbenzylamino, 4-hydroxybenzylamino, 4-chlorobenzylamino, 4-methoxybenzylamino, 4-carboxybenzylamino, 4-methoxycarbonylbenzylamino and 4-aminobenzylamino groups;

$C_2$–$C_5$ aliphatic carboxylic acyl substituted amino groups, especially $C_2$–$C_5$ alkanoylamino groups, such as the acetamido, propionamido and butyramido groups;

$C_7$–$C_{15}$ aromatic carboxylic acyl substituted amino groups, especially benzamido and naphthoylamido groups which are substituted or unsubstituted, wherein the aryl moieties may be unsubstituted or have, for example, from 1 to 5 substituents, preferably from 1 to 3 substituents, selected from the group consisting of substituents (e), which may be the same or different from one another, such as $C_1$–$C_4$ alkyl groups, hydroxy groups, halogen atoms, $C_1$–$C_4$ alkoxy groups, carboxy groups, protected carboxy groups, e.g. as exemplified above in relation to substituents (a), and amino groups; examples of such groups include the benzamido, naphthoylamido, 4-methylbenzamido, 4-hydroxybenzamido, 4-chlorobenzamido, 4-methoxybenzamido, 4-carboxybenzamido, 4-methoxycarbonylbenzamido and 4-aminobenzamido groups;

the nitro group;

the cyano group;

the carboxy group;

protected carboxy groups in which the protecting group is preferably as defined above for the protected groups of substituents (a), such as the methoxycarbonyl, ethoxycarbonyl, t-butoxycarbonyl, benzyloxycarbonyl, diphenylmethoxycarbonyl, 4-nitrobenzyloxycarbonyl, 2-nitrobenzyloxycarbonyl, allyloxycarbonyl, 2-chloroallyloxycarbonyl, 2,2,2-trichloroethoxycarbonyl, 2,2,2-tribromoethoxycarbonyl and 2-(trimethylsilyl)-ethoxycarbonyl groups;

$C_1$–$C_5$ alkyl groups, which may be straight or branched chain groups, such as the methyl, ethyl, propyl, butyl and pentyl groups;

halogen substituted $C_1$–$C_5$ alkyl groups, which may be straight or branched chain groups, such as the trifluoromethylgroup;

$C_1$–$C_5$ hydroxyalkyl groups, such as the hydroxymethyl and hydroxyethyl groups; and $C_1$–$C_5$ alkyl groups having at least one, and preferably only one, $C_2$–$C_5$ aliphatic carboxylic acyloxy substituent; examples of the alkyl group include those exemplified above in relation to substituents (b), and examples of the acyloxy group include those exemplified above in relation to substituents (a); examples of these acyloxyalkyl groups include the acetoxymethyl, 1- and 2- propionyloxyethyl and 5-butyryloxypentyl groups.

Of these substituents we prefer: the halogen atoms; the hydroxy group; the $C_1$–$C_4$ alkoxy groups; and $C_6$–$C_{14}$ aryloxy groups (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); the $C_7$–$C_9$ aralkyloxy groups (wherein the aryl moieties are unsubstituted or may have from 1 to 3 substituents, which may be the same or different from one another, such as $C_1$–$C_4$ alkyl, hydroxy, halogen $C_1$–$C_4$ alkoxy, carboxy, protected carboxy and amino substituents); the $C_2$–$C_5$ aliphatic carboxylic acyloxy groups; the $C_7$–$C_{15}$ aromatic carboxylic acyloxy groups (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); the mercapto group; the $C_1$–$C_4$ alkylthio groups; the amino group; the mono-and di-$C_1$–$C_4$ alkyl-substituted amino groups; the $C_2$–$C_5$ aliphatic carboxylic acylamino groups; the nitro group; the cyano group; the carboxy group; the protected carboxy groups; the $C_1$–$C_5$ alkyl groups; the halogen-substituted $C_1$–$C_5$ alkyl groups; the $C_1$–$C_5$ hydroxyalkyl groups; and the $C_2$–$C_5$ aliphatic carboxylic acyloxy-substituted $C_1$–$C_5$ alkyl groups.

Of these, the more preferred substituents are: the halogen atoms; the hydroxy group; the $C_1$–$C_4$ alkoxy groups; the $C_6$–$C_{14}$ aryloxy groups (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); $C_7$–$C_9$ aralkyloxy groups (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); the amino group; the mono- and di-$C_1$–$C_4$ alkyl-substituted amino groups; the $C_2$–$C_5$ aliphatic carboxylic acylamino groups; the nitro group; the cyano group; the carboxy group; the protected carboxy groups; the $C_1$–$C_5$ alkyl groups; the $C_1$–$C_5$ haloalkyl groups; the $C_1$–$C_5$ hydroxyalkyl groups; and the $C_2 \geq C_5$ aliphatic carboxylic acyloxy-substituted $C_1$–$C_5$ alkyl groups, especially $C_2 \geq C_5$ alkanoyloxy $C_1$–$C_5$ alkyl groups.

Most preferred of all are the halogen atoms; the hydroxy group; the $C_1$–$C_4$ alkoxy groups; the amino group; the mono- and di-$C_1$–$C_4$ alkyl-substituted amino groups; the $C_2$–$C_5$ aliphatic carboxylic acylamino groups; the nitro group; the $C_1$–$C_5$ haloalkyl groups; and the $C_1$–$C_5$ hydroxyalkyl groups.

Where the compound of the present invention is a hydroxy-carboxylic acid of formula (I), the compound is an acid and hence can form slats and esters. There is no particular restriction upon the nature of such salts and esters, provided that, where they are intended for therapeutic use, they should be "pharmaceutically acceptable", which, as is well known to those skilled in the art, means that they should not have a reduced activity (or unacceptably reduced activity) or an increased toxicity (or unacceptably increased toxicity) as compared with the free acids. Where the compounds are intended for non-therapeutic use, for example as intermediates in the preparation of other compounds, even these restrictions do not apply.

Preferred examples of such esters include: alkyl esters, especially $C_1$–$C_6$ alkyl esters, such as the methyl, ethyl, propyl, isopropyl, butyl, isobutyl and pentyl esters; and aralkyl esters, in which the aralkyl group is preferably as hereinbefore defined in relation to X, such as the benzyl and phenethyl esters. Of these, the most preferred are the methyl, ethyl and benzyl esters.

Pharmacologically acceptable salts of the carboxylic acids of formula (I) may be exemplified by metal salts, amino acid salts and amine salts. Examples of the metal salts include: alkali metal salts, such as the sodium and potassium salts; alkaline earth metal salts, such as the calcium and magnesium salts; and other metal salts, such as the aluminum salts, iron salts, zinc salts, copper salts, nickel salts and cobalt salts. Of these we prefer the alkali metal salts, alkaline earth metal salts and aluminum salts, and most prefer the sodium salts, potassium salts, calcium salts and aluminum salts. Examples of the amino acid salts include salts with basic amino acids, such as arginine, lysine, histidine, $\alpha\gamma$-diaminobutyric acid and ornithine. Examples of the amino salts include t-octylamine, dibenzylamine, dicyclohexylamine, morpholine, D-phenylglycine alkyl ester and D-glucosamine salts.

Preferred compounds of the present invention are:

(A) Those compounds of formula (I), in which:

R represents a hydrogen atom, a methyl group or a hydroxy group;

X represents a $C_1$–$C_{10}$ alkyl group, a $C_3$–$C_{10}$ alkenyl group, a $C_3$–$C_{10}$ cycloalkyl group, a phenyl group, a $C_7$–$C_9$ aralkyl group or an unsaturated heterocyclic group having 5 or 6 ring atoms, of which 1 or 2 are hetero-atoms selected from the group consisting of oxygen, sulfur and nitrogen hetero-atoms, in which said alkyl and alkenyl groups are unsubstituted or have from 1 to 4 substituents selected from the group consisting of substituents (a'), defined below, and said cycloalkyl, phenyl, aralkyl and heterocyclic groups are unsubstituted or have from 1 to 4 substituents selected from the group consisting of substituents (b), defined above;

A represents a single bond, a $C_1$–$C_{10}$ alkylene group, a $C_3$–$C_{10}$ alkenylene group, a $C_5$–$C_{10}$ alkadienylene group or a $C_3$–$C_5$ alkynylene group, in which said alkylene, alkenylene, alkadienylene and alkynylene groups are unsubstituted or have from 1 to 4 substituents selected from the group consisting of substituents (c'), defined below;

Y represents a $C_6$–$C_{10}$ aryl group or a $C_3$–$C_8$ cycloalkyl group, each of which may be unsubstituted or have 1 or 2 substituents independently selected from the group consisting of substituents (d'), defined below;

substituents (a'):

halogen atoms, hydroxy groups, $C_1$–$C_4$ alkoxy groups, $C_2$–$C_5$ aliphatic carboxylic acyloxy groups, amino groups, carboxy groups and protected carboxy groups;

substituents (c'):

halogen atoms, hydroxy groups, $C_1$–$C_4$ alkoxy groups, $C_6$–$C_{14}$ aryloxy groups, $C_2$–$C_5$ aliphatic carboxylic acyloxy groups, amino groups, mono-and di-$C_1$–$C_4$ alkyl-substituted amino groups, $C_2$–$C_5$ aliphatic carboxylic acylamino groups, $C_7$–$C_{15}$ aromatic carboxylic acylamino groups, carboxy groups and protected carboxy groups, in which the aryl groups of said aryloxy and aromatic carboxylic acylamino groups are unsubstituted or have from 1 to 3 substituents selected from the group consisting of substituents (e'), defined below;

substituents (d')

halogen atoms, hydroxy groups, $C_1$–$C_4$ alkoxy groups, $C_6$–$C_{14}$ aryloxy groups, $C_7$–$C_9$ aralkyloxy groups, $C_2$–$C_5$ aliphatic carboxylic acyloxy groups, $C_7$–$C_{15}$ aromatic carboxylic acyloxy groups, mercapto groups, $C_1$–$C_4$ alkylthio groups, amino groups, mono-and di-$C_1$–$C_4$ alkylsubstituted amino groups, $C_2$–$C_5$ aliphatic carboxylic acylamino groups, nitro groups, cyano groups, carboxy groups, protected carboxy groups, $C_1$–$C_5$ alkyl groups, $C_1$–$C_5$ haloalkyl groups, $C_1$–$C_5$ hydroxyalkyl groups and $C_1$–$C_5$ alkyl groups having a $C_2$-$C_5$ aliphatic carboxylic acyloxy substituent, in which the aryl groups of said aryloxy, aralkyloxy and aromatic carboxylic acyloxy groups are unsubstituted or have from 1 to 3 substituents selected from the group consisting of substituents (e'), defined below; and substituents (e')

$C_1$-$C_4$ alkyl groups, hydroxy groups, halogen, $C_1$-$C_4$ alkoxy groups, carboxy groups, protected carboxy groups and amino groups;

and pharmaceutically acceptable salts and esters thereof and the corresponding ring-closed lactones.

(B) Those compounds of formula (I) in which:

R and X are as defined in (A) above;

A represents $C_1$-$C_{10}$ alkylene group, a $C_5$-$C_{10}$ alkadienylene group, a $C_3$-$C_{10}$ alkenylene group or a $C_3$-$C_5$ alkynylene group, in which said alkylene, alkenylene, alkadienylene and alkynylene groups are unsubstituted or have 1 or 2 substituents selected from the group consisting of substituents (c'), defined in (A) above; and Y represents a heterocyclic group having 5 or 6 ring atoms of which from 1 to 3 are hetero-atoms selected from the group consisting of nitrogen, oxygen and sulfur hetero-atoms or a heterocyclic group having 5 or 6 ring atoms of which from 1 to 3 are hetero-atoms selected from the group consisting of nitrogen, oxygen and sulfur hetero-atoms and being fused to a benzene ring, said heterocyclic groups being unsubstituted or having 1 or 2 substituents selected from the group consisting of substituents (d'), defined in (A) above;

and pharmaceutically acceptable salts and esters thereof and the corresponding ring-closed lactones.

(C) Those compounds of formula (I) in which:

R and X are as defined in (A) above;

A represents a $C_3$-$C_{10}$ alkenylene group, a $C_5$-$C_{10}$ alkadienylene group or a $C_3$-$C_{10}$ alkynylene group, in which said alkenylene, alkadienylene and alkynylene groups are unsubstituted or have 1 or 2 substituents selected from the group consisting of substituents (c'), defined in (A) above; and Y represents a hydrogen atom;

and pharmaceutically acceptable salts and esters thereof and the corresponding ring-closed lactones.

Still more preferred compounds of the present invention are:

(D) Those compounds of formula (I) in which:

R represents a hydrogen atom, a methyl group or a hydroxy group;

X represents a $C_1$-$C_{10}$ alkyl group, a $C_3$-$C_{10}$ alkenyl group or a $C_3$-$C_7$ cycloalkyl group, in which said alkyl and alkenyl groups are unsubstituted or have 1 or 2 substituents selected from the group consisting of substituents (a''), defined below, and said cycloalkyl groups are unsubstituted or have 1 or 2 substituents selected from the group consisting of substituents (b'), defined below;

A represents a single bond, a $C_1$-$C_5$ alkylene group, a $C_3$-$C_5$ alkenylene group or a $C_5$-$C_8$ alkadienylene group, in which said alkylene, alkenylene and alkadienylene groups are unsubstituted or have 1 or 2 substituents selected from the group consisting of substituents (c''), defined below;

Y represents a $C_6$-$C_{10}$ aryl group or a $C_5$-$C_7$ cycloalkyl group, each of which may be unsubstituted or have 1 or 2 substituents independently selected from the group consisting of substituents (d''), defined below;

substituents (a''):

halogen atoms, hydroxy groups, $C_2$-$C_5$ aliphatic carboxylic acyloxy groups, carboxy groups and protected carboxy groups;

substituents (b'):

halogen atoms, hydroxy groups, $C_1$-$C_4$ alkoxy groups, $C_2$-$C_5$ aliphatic carboxylic acyloxy groups, $C_1$-$C_5$ alkyl groups and $C_1$-$C_5$ haloalkyl groups;

substituents (c''):

halogen atoms, hydroxy groups, $C_1$-$C_4$ alkoxy groups, amino groups, mono and di-$C_1$-$C_4$ alkyl-substituted amino groups and $C_2$-$C_5$ aliphatic carboxylic acylamino groups; and substituents (d''):

halogen atoms, hydroxy groups, $C_1$-$C_4$ alkoxy groups, $C_6$-$C_{14}$ aryloxy groups, $C_7$-$C_9$ aralkyloxy groups, amino groups, mono- and di-$C_1$-$C_4$ alkyl-substituted amino groups, $C_2$-$C_5$ aliphatic carboxylic acylamino groups, nitro groups, cyano groups, carboxy groups, protected carboxy groups, $C_1$-$C_5$ alkyl groups, $C_1$-$C_5$ haloalkyl groups, $C_1$-$C_5$ hydroxyalkyl groups and $C_1$-$C_5$ alkyl groups having a $C_2$-$C_5$ aliphatic carboxylic acyloxy substituent;

and pharmaceutically acceptable salts and esters thereof and the corresponding ring-closed lactones.

(E) Those compounds of formula (I) in which:

R and X are as defined in (D) above;

A represents a $C_1$-$C_5$ alkylene group, a $C_3$-$C_5$ alkenylene group or a $C_5$-$C_8$ alkadienylene group, in which said alkylene, alkenylene and alkadienylene groups are unsubstituted or have 1 or 2 substituents independently selected from the group consisting of substituents (c''), defined in (D) above; and Y represents a heterocyclic group having 5 or 6 ring atoms of which 1 or 2 are hetero-atoms selected from the group consisting of nitrogen and oxygen hetero-atoms or a heterocyclic group having 5 or 6 ring atoms of which 1 or 2 are hetero-atoms selected from the group consisting of nitrogen and oxygen hetero-atoms and being fused to a benzene ring, said heterocyclic groups being unsubstituted or having 1 or 2 substituents independently selected from the group consisting of substituents (d''), defined in (D) above;

and pharmaceutically acceptable salts and esters thereof and the corresponding ring-closed lactones.

(F) Those compounds of formula (I) in which:

R and X are as defined in (D) above;

A represents a $C_3$-$C_{10}$ alkenylene group or a $C_5$-$C_{10}$ alkadienylene group, in which said alkenylene and alkadienylene groups are unsubstituted or have 1 or 2 substituents independently selected from the group consisting of substituents (c''), defined in (D) above; and Y represents a hydrogen atom;

and pharmaceutically acceptable salts and esters thereof and the corresponding ring-closed lactones.

Of the compounds of the invention described above, even more preferred compounds are:

(G) Those compounds of formula (I), in which:

R represents a hydrogen atom; X represents a $C_1$-$C_7$ alkyl group, a $C_3$-$C_5$ alkenyl group or a $C_3$-$C_7$ cycloalkyl group, said alkyl and alkenyl groups being unsubstituted or having 1 or 2 substituents independently selected from the group consisting of substituents (a'''), defined below, and said cycloalkyl groups being unsubstituted or having at least one substituent selected from the group consisting of substituents (b'''), defined below;

A represents a single bond, a $C_1$-$C_5$ alkylene group or a $C_3$-$C_5$ alkenylene group, each of which may be unsubstituted or have 1 or 2 substituents independently selected from the group consisting of substituents ($c^{iv}$), defined below;

Y represents a $C_6$–$C_{10}$ aryl group or a $C_5$–$C_7$ cycloalkyl group, each of which may be unsubstituted or have 1 or 2 substituents independently selected from the group consisting of substituents ($d^{iv}$), defined below;

substituents ($a^{iv}$):
halogen atoms and carboxy groups;
substituents ($b'''$):
halogen atoms and $C_1$–$C_5$ haloalkyl groups;
substituents ($c^{iv}$):
hydroxy groups and $C_1$–$C_4$ alkoxy groups;
substituents ($d^{iv}$):
halogen atoms, hydroxy groups, $C_1$–$C_4$ alkoxy groups, amino groups, mono- and di-$C_1$–$C_4$ alkylsubstituted amino groups, $C_2$–$C_5$ aliphatic carboxylic acylamino groups, nitro groups, $C_1$–$C_5$ alkyl groups, $C_1$–$C_5$ haloalkyl groups and $C_1$–$C_5$ hydroxyalkyl groups;
and pharmaceutically acceptable salts and esters thereof and the corresponding ring-closed lactones.

(H) Those compounds of formula (I), in which:
R and X are as defined in (G) above;
A represents a $C_1$–$C_5$ alkylene group or a $C_3$–$C_5$ alkenylene group, each of which may be unsubstituted or have 1 or 2 substituents independently selected from the group consisting of substituents ($c^{iv}$), defined in (G) above; and
Y represents a heterocyclic group having 5 or 6 ring atoms of which 1 or 2 are hetero-atoms selected from the group consisting of nitrogen and oxygen heteroatoms, which may be unsubstituted or have 1 or 2 substituents independently selected from the group consisting of substituents ($d^{iv}$), defined in (G) above;
and pharmaceutically acceptable salts and esters thereof and the corresponding ring-closed lactones.

(I) Those compounds of formula (I), in which:
R and X are as defined in (G) above;
A represents a $C_3$–$C_7$ alkenylene group or a $C_3$–$C_8$ alkadienylene group, each of which may be unsubstituted or have 1 or 2 substituents independently selected from the group consisting of substituents ($c^{iv}$), defined in (G) above; and
Y represents a hydrogen atom;
and pharmaceutically acceptable salts and esters thereof and the corresponding ring-closed lactones.

Still more preferred are:

(J) Those compounds of formula (I) in which:
R represents a hydrogen atom;
X represents a $C_1$–$C_{10}$ alkyl group, a $C_3$–$C_{10}$ alkenyl group or a $C_3$–$C_{10}$ cycloalkyl group, said alkyl and alkenyl groups being unsubstituted or having at least one substituent selected from the group consisting of substituents ($a'41$), defined below, and said cycloalkyl groups being unsubstituted or having at least one substituent selected from the group consisting of substituents ($b''$), defined below;
A represents a single bond, a $C_1$–$C_{10}$ alkylene group or a $C_3$–$C_{10}$ alkenylene group, said alkylene and alkenylene groups being unsubstituted or having at least one substituent selected from the group consisting of substituents ($c'41$), defined below;
Y represents a hydrogen atom, a $C_6$–$C_{14}$ aryl group, a $C_3$–$C_{10}$ cycloalkyl group, a heterocyclic group having 5 or 6 ring atoms of which from 1 to 3 are hetero-atoms selected from the group consisting of nitrogen, oxygen and sulfur hetero-atoms or a heterocyclic group having 5 or 6 ring atoms of which from 1 to 3 are hetero-atoms selected from the group consisting of nitrogen, oxygen and sulfur hetero-atoms and being fused to a benzene ring, said aryl, cycloalkyl and heterocyclic groups being unsubstituted or having at least one substituent selected from the group consisting of substituents ($d'''$), defined below;
provided that, where X represents a 1-methylpropyl group, then —A—Y does not represent a hydrogen atom or an alkyl group;

substituents ($a'''$):
halogen atoms, carboxy groups and protected carboxy groups;
substituents ($b''$):
halogen atoms, carboxy groups, protected carboxy groups, $C_1$–$C_5$ alkyl groups and $C_1$–$C_5$ haloalkyl groups;
substituents ($c'''$):
halogen atoms, hydroxy groups and $C_1$–$C_4$ alkoxy groups; and
substituents ($d'''$):
halogen atoms, hydroxy groups, $C_1$–$C_4$ alkoxy groups, amino groups $C_1$–$C_4$ alkylamino groups, dialkylamino groups in which each alkyl group is $C_1$–$C_4$, nitro groups, carboxy groups, protected carboxy groups, $C_1$–$C_5$ alkyl groups and $C_1$–$C_5$ alkyl groups having at least one substituent selected from the group consisting of halogen atoms and hydroxy groups;
and pharmaceutically acceptable salts and esters thereof and the corresponding ring-closed lactones.

Examples of specific compounds of the invention are those compounds of formula (I) in which R, X, Y and A are as defined in the following Table 1. The compounds of the invention are hereinafter, where appropriate, identified by the numbers appended to them in this Table. In the Table, the following abbreviations are used:

| | |
|---|---|
| Ac | acetyl |
| Ada | adamantyl |
| Bdix | benzodioxanyl |
| Bfur | benzofuranyl |
| Boz | benzoyl |
| Bpyn | 3,4-dihydrobenzopyranyl |
| Bthi | benzothienyl |
| Bu | butyl |
| cBu | cyclobutyl |
| sBu | sec-butyl |
| tBu | t-butyl |
| Bun | 2-butenyl |
| Bz | benzyl |
| Chr | 2H-chromenyl |
| Dix | dioxanyl... |
| | 1,3-Dix(5) is 1,3-dioxan-5-yl & |
| | 1,4-Dix(2) is 1,4-dioxan-2-yl |
| Etc | ethoxycarbonyl |
| Fur | furyl |
| Hex | hexenyl |
| cHx | cyclohexyl |
| Ind | indolyl |
| Isox | isoxazolyl |
| Me | methyl |
| Mec | methoxycarbonyl |
| Mor | morpholino |
| Np | naphthyl |
| Ph | phenyl |
| Pin | pinanyl |
| Pip | piperidyl |
| Piz | piperazinyl |
| Pn | pentyl |
| cPn | cyclopentyl |
| tPn | t-pentyl |
| Pr | propyl |
| cPr | cyclopropyl |
| iPr | isopropyl |

| | |
|---|---|
| Pre | propenyl |
| iPre | isopropenyl |
| Pyr | pyridyl |
| Pyrd | pyrrolidinyl |
| Pyrr | pyrrolyl |
| Quin | quinolyl |
| iQuin | isoquinolyl |
| Tfm | trifluoromethyl |
| Thf | tetrahydrofuryl |
| Thi | thienyl |
| Thiz | thiazolyl |
| Thp | tetrahydropyranyl |
| Tht | tetrahydrothienyl |

TABLE 1

| Cpd No. | R | X | Y | A |
|---|---|---|---|---|
| 1 | H | sBu | Ph | —CH$_2$— |
| 2 | H | tPn | Ph | —CH$_2$— |
| 3 | H | 3-AcO-1,1-diMePr | Ph | —CH$_2$— |
| 4 | H | sBu | 4-ClPh | —CH$_2$— |
| 5 | H | sBu | 3-HOPh | —CH$_2$— |
| 6 | H | sBu | 4-MeOPh | —CH$_2$— |
| 7 | H | CCl$_3$ | 3,4-diMeOPh | —CH$_2$— |
| 8 | H | sBu | 2,6-diMePh | —CH$_2$— |
| 9 | H | sBu | 2-Tfm-Ph | —CH$_2$— |
| 10 | H | sBu | 3,4,5-triMeOPh | —CH$_2$— |
| 11 | H | sBu | 2-(HOMe)Ph | —CH$_2$— |
| 12 | H | tPn | 2-(HOMe)Ph | —CH$_2$— |
| 13 | H | tPn | 3-(HOMe)Ph | —CH$_2$— |
| 14 | H | sBu | 4-(AcOMe)Ph | —CH$_2$— |
| 15 | H | sBu | 4-NO$_2$Ph | —CH$_2$— |
| 16 | H | sBu | Ph | — |
| 17 | H | sBu | Ph | —CH$_2$CH$_2$— |
| 18 | H | sBu | Ph | —(CH$_2$)$_3$— |
| 19 | H | iPre | 4-NH$_2$Ph | —CH$_2$CH$_2$— |
| 20 | H | 1-Pre | 4-NMe$_2$Ph | —CH$_2$CH$_2$— |
| 21 | H | tBu | 4-(AcNH)Ph | —CH$_2$CH$_2$— |
| 22 | H | sBu | Ph | —CHOHCH$_2$— |
| 23 | H | 1,1-diFPr | 4-EtcPh | —(CH$_2$)$_3$— |
| 24 | H | 1,1-diEtPr | 2-HOPh | —CH$_2$CH$_2$CHMeCH$_2$— |
| 25 | H | Ph | 3-HSPh | —(CH$_2$)$_5$— |
| 26 | H | 2-MeOPh | 3-MeSPh | —CH$_2$CH$_2$CH—<br>—(NMe$_2$)CH$_2$CH$_2$— |
| 27 | H | 2-HOOCEt | 2-AcOPh | —CH$_2$CH$_2$CHMe-<br>—(CH$_2$)$_3$CHMeCH$_2$— |
| 28 | H | sBu | Ph | —CH=CHCH$_2$— |
| 29 | H | 1,1-diMePn | 3,4-diMeOPh | —CH=CHCH$_2$— |
| 30 | H | sBu | Ph | —C≡CCH$_2$— |
| 31 | H | cPr | 4-NC-Ph | —CH=CHCH$_2$CH=CHCH$_2$— |
| 32 | H | 1-Et-1-MePr | 2,6-diMeOPh | —CH$_2$CH=CMeCH$_2$— |
| 33 | H | 1-NH$_2$-2-MePr | 2-AcOPh | —CH$_2$CH=CMeCH$_2$—<br>—CH$_2$CH=CMeCH$_2$— |
| 34 | H | sBu | 1-Np | —CH$_2$— |
| 35 | H | 2-Fur | 5-MeO-1-Np | —CH$_2$— |
| 36 | H | 2,6-diMePh | 4-HOOC-Ph | —CH$_2$— |
| 37 | H | sBu | 3-Pyr | —CH$_2$— |
| 38 | H | sBu | 4-Pyr | —CH$_2$— |
| 39 | H | sBu | 2-Fur | —CH$_2$— |
| 40 | H | iPre | 3-Fur | —CH$_2$— |
| 41 | H | sBu | 2-Fur | —CH=CHCH$_2$— |
| 42 | H | 1-Etc-1-MeEt | 2-Thi | —CH$_2$— |
| 43 | H | 4-Tfm-Ph | 2-Thiz | —CH$_2$— |
| 44 | H | 3-Me-Bun | 2-Pyrr | —CH$_2$— |
| 45 | H | sBu | 2-Thf | —CH$_2$— |
| 46 | H | 1-Me-1-Pre | 2-Tht | —CH$_2$— |
| 47 | H | sBu | 2-Thp | —CH$_2$— |
| 48 | H | cPn | 2-Pyrd | —CH$_2$— |
| 49 | H | 4-FPh | 1-Me-2-Pyrd | —CH$_2$— |
| 50 | H | 2,6-diMeOPh | 2-Pip | —CH$_2$— |
| 51 | H | cHx | 2-Piz | —CH$_2$CH$_2$— |
| 52 | H | cHx | Mor | —CH$_2$CH$_2$— |
| 53 | H | 4-HOPh | 1,4-Dix(2) | —CH$_2$— |
| 54 | H | sBu | 1,3-Dix(5) | —CH$_2$— |
| 55 | H | 4-HOBu | cPr | —CH$_2$— |
| 56 | H | 4-AcOPh | 2,2-diMecPr | —CH$_2$— |
| 57 | H | 4-iPrPh | cBu | —CH$_2$— |
| 58 | H | 1-F-1-MePr | cPn | —CH$_2$CH(OMe)CH$_2$— |
| 59 | H | 1,1-diMeBu | 2-HOcPn | —(CH$_2$)$_3$— |
| 60 | H | sBu | cHx | —CH$_2$— |
| 61 | H | sBu | 4-HOcHx | —CH$_2$— |
| 62 | H | tPn | 4-HOcHx | —CH$_2$— |
| 63 | H | 1-Et-1-FPr | 4-tBucHx | —CH$_2$— |
| 64 | H | sBu | H | —CH$_2$C(Me)=CHCH$_2$— |
| 65 | H | sBu | H | —CH(OH)C(Me)=CHCH$_2$— |
| 66 | H | 4-AcO-1-MeBu | H | —CH$_2$C(Me)=CHCH$_2$—<br>—CH$_2$C(Me)=CHCH$_2$— |

TABLE 1-continued

| Cpd No. | R | X | Y | A |
|---|---|---|---|---|
| 67 | H | sBu | H | —CH(OH)C(Me)=CHCH₂— |
| 68 | H | 1-Hex | 4-Quin | —CH₂C(Me)=CHCH₂— |
| 69 | H | 3-Fur | 1-iQuin | —CH₂— |
| 70 | H | 2-Thi | 4-(2-MeOPhO)Ph | —CH(NH₂)—CH₂— |
| 71 | H | sBu | H | —CH(2-HOPhOCO)— |
| 72 | H | sBu | H | —CMe=CHCH₂— |
| 73 | H | 1-NH₂-3-MecPr | 4-BozOPh | —CH(NBz₂)CH₂— |
| 74 | H | 3-Pyr | 4-PhSPh | —CH₂CH(MeO)CH₂— |
| 75 | H | Pn | 4-(2-MePhNH)Ph | —CH₂CH(Mec)CH₂— |
| 76 | H | sBu | H | —CH₂CH(BzO)CH₂— |
| 77 | H | 4-HOOC-Bu | 4-PhSPh | —CH(4-FPhO)CH(AcO)— —CH₂— |
| 78 | H | 2-EtcPh | 4-PhOPh | —CHCl(CH₂)₄— |
| 79 | H | sBu | 2-Bfur | —CH₂— |
| 80 | H | sBu | 2-Bfur | —CH=CHCH₂— |
| 81 | H | sBu | 2-Bpyn | —CH₂— |
| 82 | H | 4-Pyr | 2-Bthi | —CH₂— |
| 83 | H | 4-ClPh | 3-Ind | —CH₂— |
| 84 | H | 1-EtPr | 2,3-diH-Bfur | —CH₂— |
| 85 | H | sBu | 2-Chr | —CH(BozO)CH₂— |
| 86 | H | sBu | 2-Bdix | —CH₂— |
| 87 | H | iPre | 3-Pin | —CH₂— |
| 88 | H | HOCH₂C(Me)=CH— | Ada | —CH(NHAc)CH₂— |
| 89 | Me | sBu | Ph | —CH₂— |
| 90 | Me | tPn | Ph | —CH₂— |
| 91 | Me | 1,1-diFPr | 3-HOPh | —CH₂— |
| 92 | Me | sBu | 3,4-diMeOPh | —(CH₂)₃— |
| 93 | Me | 1,1-diEtPr | 2-HOMePh | —CH₂— |
| 94 | Me | sBu | 3-AcOMePh | —CH=CHCH₂— |
| 95 | Me | 1-F-1-MePr | 3-Pyr | —CH₂— |
| 96 | Me | tPn | 2-Fur | —CH₂— |
| 97 | Me | 3-HO-1,1-diMePr | 2-Fur | —CH=CHCH₂— |
| 98 | Me | tBu | 2-Thf | —CH₂— |
| 99 | Me | 1-EtBu | Mor | —(CH₂)₂— |
| 100 | Me | iPre | 1,3-Dix(5) | —CH₂— |
| 101 | Me | 4-Etc-1-MeBu | 4-HOcHx | —CH₂— |
| 102 | Me | 1-Cl-1-MePr | 4-HOcHx | —CH₂— |
| 103 | Me | sBu | H | —CH₂C(Me)=CHCH₂— |
| 104 | Me | tPn | H | —CH(OH)C(Me)=CHCH₂— |
| 105 | Me | sBu | H | —CH(OPh)CH₂— |
| 106 | Me | iPre | H | —CH(4-MeOBzO)CH₂— |
| 107 | Me | 4-HO-1,1-diMeBu | 2-Bfur | —CH₂— |
| 108 | Me | sBu | 2-Bdix | —CH₂— |
| 109 | OH | sBu | Ph | —CH₂— |
| 110 | OH | tPn | Ph | —CH₂— |
| 111 | OH | 1-Et-1-MePr | 2-TfmPh | —CH₂— |
| 112 | OH | 1,1-diFPr | 2-AcOMePh | —CH₂— |
| 113 | OH | sBu | 3-Pyr | —CH₂— |
| 114 | OH | sBu | 2-Fur | —CH₂— |
| 115 | OH | 2-MeOEt | 2-Fur | —CH=CHCH₂— |
| 116 | OH | 1-Me-1-Pre | cHx | —CH₂— |
| 117 | OH | sBu | H | —CH₂C(Me)=CHCH₂— |
| 118 | OH | sBu | H | —CH(BzO)C(Me)=CHCH₂— |
| 119 | H | sBu | 3-Tfm-Ph | —CH₂— |
| 120 | H | sBu | 3-(HOMe)Ph | —CH₂— |
| 121 | H | sBu | 2-HOPh | —CH₂CH₂— |
| 122 | H | sBu | Mor | —CH₂CH₂— |
| 123 | H | sBu | 4-MePh | —CH₂— |
| 124 | H | sBu | 2,5-diMePh | —CH₂— |
| 125 | H | sBu | 2-(1-HO-1-MeEt)Ph | —CH₂— |
| 126 | H | sBu | 2-EtOPh | —CH₂— |
| 127 | H | sBu | 4-BuOPh | —CH₂— |
| 128 | H | sBu | 5-Isox | —CH₂— |
| 129 | H | sBu | 4-FPh | —CH₂— |
| 130 | H | sBu | 1,3-Dix(5) | —CH=CHCH₂— |
| 131 | H | sBu | 4,6-diMe1,3-Dix(5) | —CH₂— |
| 132 | H | sBu | 3-MeOPh | —CH₂— |
| 133 | H | sBu | 4-BrPh | —CH₂— |
| 134 | H | sBu | 4-(HOMe)Ph | —CH₂— |

Of the compounds listed above, the following compounds are preferred, that is to say Compounds No. 1, 6, 11, 17, 18, 22, 37, 39, 45, 47, 54, 60, 61, 64, 65, 120, 122, 123, 124, 126, 127, 128, 129, 130, 131, 132 and 18, 22, 37, 39, 45, 47, 54, 60, 61, 64, 65, 120, 122, 123, 124, 126, 127, 128, 129, 130, 131, 132 and 18, 22, 37, 39, 45, 47, 54, 60, 61, 64, 65, 120, 122, 123, 124, 126, 127, 128, 129, 130, 131, 132 and 143, and the following are the most preferred;

1. 1-(2-methylbutyryl)-3,4-dihydro-6-oxo-4-benzyloxyiminoiso-ML-236A lactone and its salts and esters, especially sodium 1-(2-methylbutyryl)-3,4-dihydro-6-oxo-4-benzyloxyiminoiso-ML-236A carboxylate and benzyl 1-(2-methylbutyryl)-3,4-dihydro-6-oxo-4-benzyloxyiminoiso-ML-236A carboxylate;

18. 1-(2-methylbutyryl)-3,4-dihydro-6-oxo-4-(3-phenylpropyl)oxyiminoiso-ML-236A lactone and its salts and esters, especially sodium 1-(2-methylbutyryl)-3,4-dihydro-6-oxo-4-(3-phenylpropyl)oxyiminoiso-ML-236A carboxylate;

39. 1-(2-methylbutyryl)-3,4-dihydro-6-oxo-4-furfuryloxyiminoiso-ML-236A lactone and its salts and esters, especially sodium 1-(2-methylbutyryl)-3,4-dihydro-6-oxo-4-furfuryloxyiminoiso-ML-236A carboxylate and benzyl 1-(2-methylbutyryl)-3,4-dihydro-6-oxo-4-furfuryloxyiminoiso-ML-236A carboxylate;

54. 1-(2-methylbutyryl)-3,4-dihydro-6-oxo-4-(1,3-dioxan-5-yl-methyl)oxyiminoiso-ML-236A lactone and its salts and esters, especially sodium 1-(2-methylbutyryl)-3,4-dihydro-6-oxo-4-(1,3-dioxan-5-yl methyl)-oxyiminoiso-ML-236A carboxylate;

60. 1-(2-methylbutyryl)-3,4-dihydro-6-oxo-4-cyclohexylmethyloxyiminoiso-ML-236A lactone and its salts and esters, especially sodium 1-(2-methylbutyryl)-3,4-dihydro-6-oxo-4-cyclohexylmethyloxyiminoiso-ML-236A carboxylate;

61. 1-(2-methylbutyryl)-3,4-dihydro-6-oxo-4-(cis-4-hydroxycyclohexylmethyl)oxyiminoiso-ML-236A lactone and its salts and esters, especially sodium 1-(2-methylbutyryl)-3,4-dihydro-6-oxo-4-(cis-4-hydroxycyclohexyl methyl)oxyiminoiso-ML-236A carboxylate;

64. 1-(2-methylbutyryl)-3,4-dihydro-6-oxo-4-(3-methyl-2-butenyl)oxyiminoiso-ML-236A lactone and its salts and esters, especially sodium 1-(2-methylbutyryl)-3,4-dihydro-6-oxo-4-(3-methyl-2-butenyl)oxyiminoiso-ML-236A carboxylate.

The compounds of the present invention contain or can contain several asymmetric carbon atoms, and these can give rise to various optical isomers. Also, because of the presence of the oxime moiety ($=NO-A-Y$), syn and anti stereoisomers exist for all of the compounds of the invention, both the free acids and their salts and esters of formula (I) and the lactone compounds of formula (II). Although these isomers are all represented herein by a single plane formula, it will be understood that the present invention contemplates both the individual isolated isomers and mixtures thereof.

In one preferred embodiment, the carboxylic acids of formula (I), esters and pharmacologically acceptable salts thereof, and the lactone compounds of formula (II), can be prepared by the process illustrated below in Reaction Scheme A:

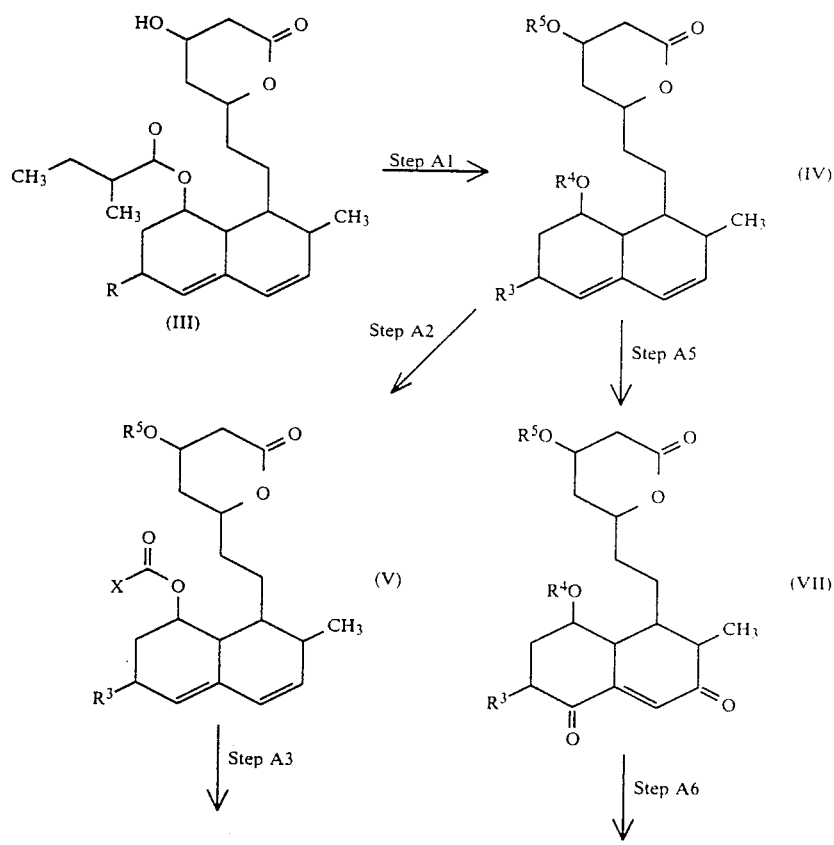

Reaction Scheme A -continued

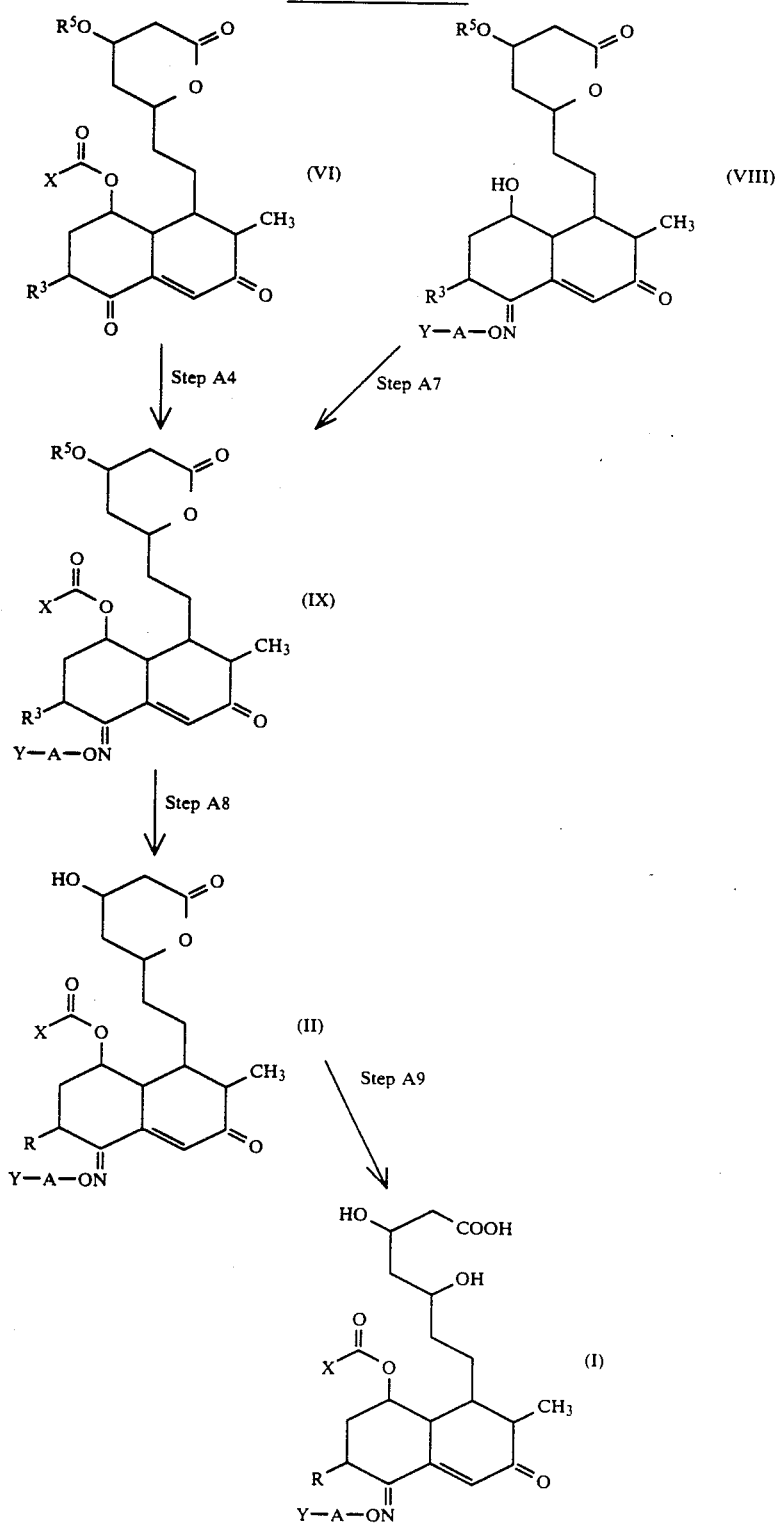

In the above formulae:

R, X, A, Y and the group of formula —A—Y are as defined above;

$R^3$ represents a hydrogen atom, a methyl group or a group of formula $R^7O$, wherein $R^7$ represents a hydrogen atom or a hydroxy-protecting group;

$R^4$ represents a hydrogen atom or a hydroxy-protecting group; and $R^5$ represents a hydrogen atom or a hydroxy-protecting group.

The starting material for the above reaction scheme is a compound of formula (III). Such a compound in which R represents a hydrogen atom is described, together with details of its preparation, for example, in U.S. Pat. No. 3,983,140 and in Japanese Provisional Patent Publication No. 51992/1981, the disclosures whereof are incorporated herein by reference. That in which R represents a methyl group is described, together with details of its preparation, for example, in U.K. Patent Specification No. 2 046 737, the disclosure of which is incorporated herein by reference. That wherein R represents a hydroxy group is described, together with details of its preparation, for example, in U.S. Pat. No. 4,346,227, No. 4,448,979, and No. 4,537,859, and in Japanese Provisional Patent Publications Nos. 155995/1982 and 10572/1983, the disclosures whereof are incorporated herein by reference.

A compound of formula (IV) wherein $R^3$, $R^4$ and $R^5$ each represents a hydrogen atom is described, together with details of its preparation, for example, in Japanese Provisional Patent Publications Nos. 136885/1976 and 83290/1982, the disclosures whereof are incorporated herein by reference; and that wherein $R^3$ represents a methyl group, and $R^4$ and $R^5$ each represents a hydrogen atom is described, together with details of its preparation, for example, in Japanese Provisional Patent Publication No. 139396/1980, the disclosure of which is incorporated herein by reference.

A compound of formula (V) wherein $R^3$ represents a hydrogen atom, a methyl group or a hydroxy group; X represents a 1-methylpropyl group; and $R^5$ represents a hydrogen atom is the same as the compound having the above general formula (III), which is described above. Compounds wherein X represents a group other than the 1-methylpropyl group are described, together with details of their preparation, for example, in U.K. Patent Specification No. 2 073 193 and USSN 906 034, filed 10 September 1986, in European Patent Publication No. 33 538, and in Japanese Provisional Patent Publication Nos. 175450/1984, the disclosures whereof are incorporated herein by reference.

A compound of formula (VI) wherein $R^3$ *l represents a hydrogen atom or a methyl group; X represents a* 1-methylpropyl group; and $R^5$ represents a hydrogen atom or a protecting group for the hydroxy group is described in U.S. Pat. Nos. 4,361,515, 4,604,472 and 4,733,003, the disclosures whereof are incorporated herein by reference.

A compound of formula (VII) wherein $R^3$ represents a hydrogen atom or a methyl group; and $R^4$ and $R^5$ each represents a hydrogen atom or a protecting group for the hydroxy group is described in Japanese Provisional Patent Publication No. 55443/1983, the disclosure of which is incorporated herein by reference.

In Step A1, a compound of formula (IV) is prepared from the starting material of formula (III) by:

(1) eliminating the 2-methylbutyryl group from the compound of formula (III); and, (2) if necessary, where R represents a hydroxy group, protecting that hydroxy group (to form the group represented by $R^3$).

Reaction (1), for eliminating the 2-methylbutyryl group, may be effected by contacting the compound of formula (III) with not less than 2 equivalents of an alkali metal hydroxide (such as sodium hydroxide, potassium hydroxide or lithium hydroxide). The reaction is preferably effected in the presence of a solvent. There is not particular restriction on the nature of the solvent to be employed, provided that it has no adverse effect on the reaction or on the reagents involved. Examples of suitable solvents include: water; alcohols, such as methanol, ethanol, propanol or ethylene glycol; ethers, such as tetrahydrofuran or dioxane; and mixtures of water with any one or more of the organic solvents mentioned above. The reaction can take place over a wide range of temperatures, and the precise reaction temperature is not critical to the invention. In general, we find it convenient to carry out the reaction at a temperature from about room temperature to 100° C., more preferably from 60 to 100° C. The time required for the reaction may also vary widely, depending on many factors, notably the reaction temperature and the nature of the reagents. However, provided that the reaction is effected under the preferred conditions outlined above, a period of from 3 to 48 hours, more preferably from 5 to 24 hours will usually suffice.

In most cases, this reaction will lead to the decyclization of the lactone moiety simultaneously with the elimination of the 2-methylbutyryl group, thereby forming an alkali metal salt in which the metal is derived from the alkali metal hydroxide used for the elimination of the 2-methylbutyryl group. Accordingly, it is possible, in this reaction, to use a ring-opened metal carboxylate as the starting material in place of the lactone compound of formula (III). Although the ring-opened metal carboxylate obtained directly from reaction (1) may be used as such for the subsequent reaction, we find that better yields are achieved if the lactone compound is used.

Accordingly, we normally then prefer to lactonize the compound obtained in reaction (1). In general terms, this may be achieved by the acidification of the reaction mixture from reaction (1). In more detail, the reaction mixture obtained in reaction (1) is cooled, and an inorganic acid, such as hydrochloric acid or sulfuric acid, is added to the cooled reaction mixture, to adjust its pH to a value of about 3. The mixture is then extracted with a water-immiscible organic solvent. There is no particular restriction on the nature of the solvent to be employed, provided that it has no adverse effect on the compounds and that it is water-immiscible. Examples of suitable solvents for the extraction include: organic esters, such as ethyl acetate; aromatic hydrocarbons, such as benzene or toluene; ethers, such as diethyl ether; and halogenated hydrocarbons, preferably halogenated aliphatic hydrocarbons, such as methylene chloride or chloroform. Of these, we prefer ethyl acetate, benzene or methylene chloride. The solvent is then distilled from the resulting extract to yield a ring-opened carboxylic acid product.

Lactonization of the ring-opened carboxylic acid product thus obtained can be achieved by contacting it directly with an acid in the presence of a solvent, without any intervening purifications, or by dehydration with heating. When the lactonization is to be effected by contact with an acid, the acid is preferably a strong organic acid, such as trifluoroacetic acid or p-toluenesulfonic acid, and the reaction is preferably effected in the presence of a solvent. There is no particular restriction on the nature of the solvent to be employed, provided that it has no adverse effect on the reaction or on the reagents involved. Examples of suitable solvents include: organic acid esters, such as ethyl acetate; halogenated hydrocarbons, preferably halogenated aliphatic hydrocarbons, such as methylene chloride; and nitriles, such as acetonitrile. The reaction can take place over a wide range of temperatures, and the precise reaction temperature is not critical to the invention. In general we find it convenient to carry out the reaction at a temperature from 0 to 100° C., more preferably from about room temperature to 60° C. The time required for the reaction may also vary widely, depending on many factors, notably the reaction temperature and the nature of the reagents. However, provided that the reaction is effected under the preferred conditions outlined above, a period of from 30 minutes to 10 hours, more preferably from 1 to 5 hours will usually suffice.

After completion of the reaction, the resulting lactone produce may be collected from the reaction mixture by conventional means. For example, one suitable recovery scheme comprises: when a waterimmiscible solvent is used as the reaction solvent, adding an aqueous solution of sodium bicarbonate to wash out the 2-methylbutyric acid (formed as a result of the reaction eliminating the 2-methylbutyryl group) and the acid catalyst; then washing the mixture with water; and finally removing the solvent from the reaction mixture to obtain the desired product.

Another alternative recovery scheme comprises, when a water-miscible solvent is used as the reaction solvent: adding an aqueous solution of sodium bicarbonate, to neutralize the reaction mixture; distilling off the solvent from the mixture; dissolving the resulting residue again in a water-immiscible organic solvent; washing the resulting solution with water to remove the 2-methylbutyric acid (formed as a result of the reaction eliminating the 2-methylbutyryl group) and the acid catalyst; and finally distilling the solvent from the reaction mixture.

Alternatively, when the lactonization is to be achieved by dehydration with heating, the carboxylic acid product is heated under reflux in a suitable solvent (for example, an aromatic hydrocarbon, such as toluene or benzene) using a Dean-Stark apparatus to separate continuously the water in the reaction. The time required for the reaction may vary widely, depending on many factors, especially on the reagents to be employed in the reaction and the reaction temperature; in general, a period of from 2 to 8 hours, more preferably from 3 to 5 hours will suffice.

After completion of the reaction, the resulting lactone product may be collected from the reaction mixture by conventional means. For example, one suitable recovery technique comprises: cooling the reaction mixture; adding an aqueous solution of sodium bicarbonate thereto to wash off the 2-methylbutyric acid formed as a result of the reaction eliminating the 2-methylbutyryl group; and then distilling the solvent from the reaction mixture. The desired compound thus obtained can be further purified, if desired, using a variety of conventional methods, such as recrystallization, reprecipitation, or the various chromatography techniques, such as column chromatography.

Of course, if the desired final product is a compound in which X—CO—is a 2-methylbutyryl group, then reaction (1) may be unnecessary and can then be omitted.

Reaction (2) may also be unnecessary if R represents a methyl group or a hydrogen atom. It involves protecting the hydroxy group represented by R. It may be effected by reacting the compound obtained by elimination of the 2-methylbutyryl group in reaction (1) with a compound which will form the hydroxy-protecting group. The nature of the reaction employed to form the protected hydroxy group will, of course, depend on the nature of the protecting group, as is well known in the art.

Examples of compounds for forming the protected hydroxy group include: silyl compounds, such as trimethylsilyl chloride, dimethyl-t-butylsilyl chloride or diphenyl-t-butylsilyl chloride; heterocyclic compounds, such as dihydropyran, dihydrothiopyran, dihydrothiophene or 4-methoxy-5,6-dihydro (2H)pyran; and unsaturated compounds, such as ethyl vinyl ether or methoxy-1-cyclohexene.

When a silyl compound is used, the reaction is preferably conducted in the presence of an organic base (such as triethylamine, dimethylaminopyridine, imidazole or pyridine) or of a sulfide compound [such as lithium sulfide ($Li_2S$)]. When a heterocyclic compound or an unsaturated compound is used, the reaction is preferably conducted in the presence of a small amount of an acid, for example: an inorganic acid, such as hydrochloric acid, sulfuric acid or phosphoric acid; another inorganic acidic compound, such as phosphorous oxychloride; or an organic acid, such as p-toluenesulfonic acid, trifluoroacetic acid, picric acid or benzenesulfonic acid. In any case, the reactions are preferably conducted in the presence of a solvent. There is no particular restriction on the nature of the solvent to be employed, provided that it has no adverse effect on the reaction or on the reagents involved. Examples of suitable solvents include: ethers, such as tetrahydrofuran; nitriles, such as acetonitrile; halogenated hydrocarbons, preferably halogenated aliphatic hydrocarbons, such as methylene chloride; and fatty acid amides, especially dialkylformamides, such as dimethylformamide. Also, particularly when a silyl compound is used, an organic amine, such as pyridine or triethylamine may be used as the solvent. In any case, the reaction can take place over a wide range of temperatures, and the precise reaction temperature is not critical to the invention. In general, we find it convenient to carry out the reaction at a relatively low temperature, e.g. a temperature from about 0° C. to room temperature. The time required for the reaction may also vary widely, depending on many factors, notably the reaction temperature and the nature of the reagents. However, provided that the reaction is effected under the preferred conditions outlined above, a period of from 30 minutes to 8 hours will usually suffice.

After completion of the reaction, the desired compound can be collected from the reaction mixture by conventional means. For example, a satisfactory recovery technique comprises: adding water to the reaction mixture; adding a water-immiscible organic solvent to extract the desired product; washing the extract with water; and finally distilling the solvent from the extract to obtain the desired product. The desired compound thus obtained can be further purified, if necessary, by conventional means, such as recrystallization, reprecipitation, or the various chromatography techniques, such as column chromatography. In this step, the desired hydroxy group can be protected selectively by appropriate choice of the selected compound used for forming the protecting group for the hydroxy group.

In Step A2 a compound of formula (V) is prepared from a compound of formula (IV), in which $R^4$ represents a hydrogen atom, by incorporating a group of formula X—CO—into the compound of formula (IV). This process is optional. Thus, when X represents, for example, 1-methylpropyl group, the compound of formula (V) is the same as the compound of formula (III) except that the former has a protecting group. Accordingly, this step is not an essential process.

In this Step, the group of formula $R^4O-$ at the 1-position is replaced by a group of formula $X-CO-$ in which X represents a group other than a 1-methylpropyl group. This reaction can be effected by contacting the compound of formula (IV) (in which $R^4$ represents a hydrogen atom and in which $R^5$ and $R^7$ each desirably represents a hydroxy-protecting group) with an organic acid having the formula X—COOH or an acid anhydride thereof or another reactive derivative thereof, such as an acid halide. When an organic acid is employed, the reaction is preferably conducted in the presence of a condensation agent, such as N,N-dicyclohexylcarbodiimide, [preferably in an amount of from 1 to 3 equivalents per equivalent of compound of formula (IV)] and, if necessary, of an organic base, such as 4-dimethylaminopyridine, 4-pyrrolidinopyridine or 4-hydroxybenzotriazole [preferably in an amount of from 1/10 to 3/10 equivalent per equivalent of the compound of formula (IV)]. The reaction is preferably conducted in the presence of a solvent. There is no particular restriction on the nature of the solvent to be employed, provided that it has o adverse effect on the reaction or on the reagents involved. Examples of suitable solvents include: amines, such as pyridine or triethylamine; halogenated hydrocarbons, preferably halogenated aliphatic hydrocarbons, such as methylene chloride or chloroform; ethers, such s tetrahydrofuran or dioxane; fatty acid amides, especially dialkylformamides, such as dimethylformamide; and dialkyl sulfoxides, such as dimethyl sulfoxide. The reaction can take place over a wide range of temperatures, and the precise reaction temperature is not critical to the invention. In general, we find it convenient to carry out the reaction at a temperature from about room temperature to 60° C. The time required for the reaction may also vary widely, depending on many factors, notably the reaction temperature and the nature of the reagents. However, provided that the reaction is effected under the preferred conditions outlined above, a period of from 5 to 48 hours will usually suffice.

When an acid anhydride or a acid halide is used, the amount employed is preferably from 3 to 5 equivalents of the acid anhydride or acid halide per equivalent of the compound of formula (IV). If necessary, the reaction may be carried out in the presence of an organic base, such as 4-dimethylaminopyridine, 4-pyrrolidinopyridine or 4-hydroxybenzotriazole, preferably in an amount of from 1/10 to 2/10 equivalent per equivalent of the compound of formula (IV).

The reaction is preferably conducted in the presence of a solvent. There is no particular restriction on the nature of the solvent to be employed, provided that it has no adverse effect on the reaction or on the reagents involved. Examples of suitable solvents include: amines, such as pyridine or triethylamine; halogenated hydrocarbons, preferably halogenated aliphatic hydrocarbons, such as methylene chloride or chloroform; and ethers, such a tetrahydrofuran or dioxane. The reaction can take place over a wide range of temperatures, and the precise reaction temperature is not critical to the invention. In general, we find it convenient to carry out the reaction at a temperature from 0 to 100° C. The time required for the reaction may also vary widely, depending on many factors, notably the reaction temperature and the nature of the reagents. However, provided that the reaction is effected under the preferred conditions outlined above, a period of from 3 to 24 hours will usually suffice.

After completion of the reaction, the desired compound can be collected from the reaction mixture by conventional means. For example, one suitable recovery technique comprises: adding a water-immiscible organic solvent to the reaction mixture to extract the desired compound; washing the extract successively with an aqueous acidic solution and with water; and finally distilling the solvent from the extract to obtain the desired product. The desired compound thus obtained can be further purified, if necessary, by conventional means ,such as recrystallization, reprecipitation, or the various chromatography techniques, such as column chromatography.

In Step A3 a compound of formula (VI) is prepared from the compound of formula (V), obtained in Step A2, by oxidizing the compound of formula (V). This reaction may be carried out by contacting the compound of formula (V) with an oxidizing agent in the presence of a solvent. There is no particular restriction on the nature of the oxidizing agents to be employed in this reaction, provided that they do not harm other parts of the molecule of the compound of formula (V), and any such compound commonly used in the art for this type of reaction may equally be used here. Examples include: a complex of chromic anhydride with an organic base [such as a complex of chromic anhydride with pyridine (Collin's reagent), pyridinium dichromate or pyridinium chlorochromate] or a complex of chromic anhydride with sulfuric acid (Jones reagent). Of these, a complex of chromic anhydride with pyridine is preferred. The reaction is preferably conducted in the presence of a solvent. There is no particular restriction on the nature of the solvent to be employed, provided that it has no adverse effect on the reaction or on the reagents involved. Examples of suitable solvents include: halogenated hydrocarbons, preferably halogenated aliphatic hydrocarbons, such as methylene chloride, 1,2-dichloroethane or chloroform; and fatty acid amides, especially dialkylformamides, such as dimethylformamide, and dialkylacetamides, such as dimethylacetamide. The reaction can take place over a wide range of temperatures, and the precise reaction temperature is not critical to the invention. In general, we find it convenient to carry out the reaction at a temperature from $-10$ to 50° C., preferably from 0° C. to about room temperature. The time required for the reaction may also vary widely, depending on many factors, notably the reaction temperature and the nature of the reagents. However, provided that the reaction is effected under the preferred conditions outlined above, a period of from 1 to 48 hours, preferably from 8 to 16 hours will usually suffice.

In Step A4, an oxime derivative of formula (IX) is prepared by contacting the compound of formula (VI) with a hydroxylamine derivative of formula $H_2NO-A-Y$ (in which A and Y are as defined above).

The hydroxylamine derivative of formula $H_2NO-A-Y$ used in this reaction may be commercially available or it can be synthesized following the method described in "Acta Chimica Acdemiae Scientiarum Hungaricae", Vol. 84, p. 167 (1975) or in "Synthesis", p. 682 (1976). The hydroxylamine derivative of formula $H_2NO-A-Y$ can be used as such or in the form of a salt with an inorganic acid such as hydrochloric acid, sulfuric acid or nitric acid, most preferably in the form of the hydrochloride.

This Step is preferably effected in the presence of a base, in order to facilitate the reaction. The nature of the base is not critical provided that it does not harm the reagents, and examples include tertiary alkylamines, such as triethylamine or tributylamine; aromatic amines, such as pyridine or lutidine; alkali metal salts of acetic acid, such as sodium acetate or potassium acetate; and alkali metal bicarbonates or carbonates, such as sodium bicarbonate, sodium carbonate or potassium carbonate. The most preferred bases are triethylamine, pyridine and sodium acetate.

The reaction is preferably conducted in the presence of a solvent. There is no particular restriction on the nature of the solvent to be employed, provided that it has no adverse effect on the reaction or on the reagents involved. Examples of suitable solvents include: alcohols, such as methanol, ethanol or propanol; ethers, such as tetrahydrofuran or dioxane; and mixtures of water with any one or more of these organic solvents.

Since the compound of formula (VI) used as the raw material in this Step contains a diketone moiety, the compound of formula (IX) can be selectively prepared by careful control of the amount of hydroxylamine derivative which is the oxime-forming agent. Specifically, by using from 1 to 1.2 equivalents of the hydroxylamine derivative for each equivalent of the compound of formula (VI), the compound of formula (IX) can be selectively prepared as the major product. If amounts of hydroxylamine derivative above this recommended range are employed, as the amount of hydroxylamine derivative increases, the amount of dioxime by-product will also tend to increase, which is undesirable.

The reaction can take place over a wide range of temperatures, and the precise reaction temperature is not critical to the invention. In general, we find it convenient to carry out the reaction at a temperature from −10 to 100° C., preferably at a temperature from 0 to 50° C. The time required for the reaction may also vary widely, depending on many factors, notably the reaction temperature and the nature of the reagents. However, provided that the reaction is effected under the preferred conditions outlined above, a period of from 30 minutes to 10 hours, preferably from 1 to 5 hours will usually suffice.

After completion of the reaction, the desired compound may be collected from the reaction mixture by conventional means. For example, one suitable recovery technique comprises: adding a water-immiscible organic solvent to the reaction mixture; washing the resulting mixture with water; and finally distilling off the solvent to obtain the desired compound. The desired compound thus obtained can be further purified, if necessary, by conventional means, such as recrystallization, reprecipitation, or the various chromatography techniques, such as column chromatography.

In Step A5, which is the beginning of an alternative sequence of reactions for preparing the compound of formula (IX), a compound of formula (VII) is prepared by oxidizing the compound of formula (IV). This reaction involves the same operations and may be carried out under the same conditions as described in Step A3.

In Step A6 a compound of formula (VIII) is prepared by:

(1) contacting the compound of formula (VII) with a hydroxylamine derivative of formula $H_2NO-A-Y$, and, if necessary, (2) eliminating the $R^4$ group when it is a hydroxy-protecting group.

These two reactions may be carried out in any order, i.e. either reaction (1) or (2) may be first, followed by the other.

Reaction (1) is effected by contacting the compound of formula (VII) with a hydroxylamine derivative of formula $H_2NO-A-Y$ under the same conditions as described in Step A4.

Reaction (2), in which the $R^4$ group is eliminated, when it is a hydroxy-protecting group, can be achieved using any method known in the art, although the exact reaction chosen will depend on the type of hydroxy-protecting group. When the hydroxy-protecting group is, for example, a tri-lower alkylsilyl group, diphenyl-lower alkylsilyl group or phenyl-di-lower alkylsilyl group, in which each alkyl group (which may be the same or different) preferably has from 1 to 4 carbon atoms, such as the trimethylsilyl, dimethyl-t-butylsilyl or diphenyl-t-butylsilyl group, the reaction is preferably effected by treating the compound with a compound generating fluoride ions (such as tetrabutylammonium fluoride or hydrofluoric acid) or with an acid, such as trichloroacetic acid or trifluoroacetic acid. The reaction is preferably effected in the presence of a solvent. There is no particular restriction on the nature of the solvent to be employed, provided that it has no adverse effect on the reaction or on the reagents involved. Examples of suitable solvents include: ethers, such as tetrahydrofuran or dioxane; and nitriles, such as acetonitrile. When a fluoride ion is used, an organic acid (such as acetic acid or propionic acid) may be added, if desired, in order to accelerate the reaction. The reaction can take place over a wide range of temperatures, and the precise reaction temperature is not critical to the invention. In general, we find it convenient to carry out the reaction at a temperature from about −10° C. to about room temperature. The time required for the reaction may also vary widely, depending on many factors, notably the reaction temperature and the nature of the reagents. However, provided that the reaction is effected under the preferred conditions outlined above, a period of from 2 to 10 hours will usually suffice.

Alternatively, when the hydroxy-protecting group is, for example, a heterocyclic group (such as the 2-tetrahydropyranyl, 2-tetrahydrothiopyranyl, 2-tetrahydrothienyl and 4-methoxytetrahydropyran-4-yl groups) or an alkoxy-substituted hydrocarbon group (such as the 1-ethoxyethyl and 1-methoxycyclohexane-1-yl groups), such elimination can be facilitated by contacting the resulting compound with a catalytic amount of acid. Acids which can be employed in the reaction preferably include: organic acids, such as formic acid, acetic acid, propionic acid, butyric acid, oxalic acid, malonic acid or p-toluenesulfonic acid, and inorganic acids, such as hydrochloric acid, hydrobromic acid or sulfuric acid. The reaction is preferably conducted in the presence of a solvent. There is no particular restriction on the nature of the solvent to be employed, provided that it has no adverse effect on the reaction or on the reagents involved. Examples of suitable solvents include: water; alcohols, such as methanol or ethanol; ethers, such as tetrahydrofuran or dioxane; and mixtures of water and any one or more of these organic solvents. The reaction can take place over a wide range of temperatures, and the precise reaction temperature is not critical to the invention. In general, we find it convenient to carry out the reaction at a temperature from room temperature to the reflux temperature of the solvent employed, particularly at room temperature. The time required for the reaction may also vary widely, depending on many factors, notably the reaction temperature and the nature of the reagents. However, provided that the reaction is effected under the preferred conditions outlined above, a period of from 1 to 5 hours will usually suffice.

After completion of the reaction, the desired compound may be collected from the reaction mixture by conventional means. For example, one suitable recovery technique comprises: adding a water-immiscible organic solvent to the reaction mixture; washing the resulting mixture with water; and finally distilling off the solvent to obtain the desired compound. The desired compound thus obtained can be further purified, if necessary, by conventional means, such as recrystallization, reprecipitation, or the various chromatography techniques, such as column chromatography.

In Step A7 a compound of formula (IX) is prepared by incorporating a group of formula X—CO— into the compound of formula (VIII). The reaction is essentially the same as and may be conducted under the same conditions as those described in Step A2.

In Step A8 a compound of formula (II) is prepared by eliminating the group(s) of formulae $R^5$ and/or $R^7$, when they are hydroxy-protecting groups. The reaction is conducted under the same conditions as described in Step A6.

In Step A9 a carboxylic acid of formula (I), or an ester or pharmacologically acceptable salt thereof, is prepared, if desired, by converting the compound of formula (II) into a metal salt of the carboxylic acid or into an ester derivative, each having a decyclized lactone moiety, using conventional reactions for this purpose, such as hydrolysis or solvolysis.

The preparation of the metal salt of the carboxylic acid can be effected by subjecting the lactone compound to ordinary hydrolytic treatment. For example, the lactone compound may be contacted with a suitable basic compound, such as a hydroxide or carbonate, of the desired metals, especially alkali or alkaline earth metals, such as sodium hydroxide, potassium hydroxide, calcium hydroxide or sodium carbonate, in a suitable solvent, for example water or an aqueous organic solvent such as an aqueous alcohol, aqueous acetone or aqueous dioxane, to give the desired compound. The amount of the alkali metal hydroxide or the like usually used in the reaction is preferably from 1 to 1.5 mole per mole of the compound of formula (II). The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents. However, provided that the reaction is effected under the preferred conditions outlined above, a period of from 1 to 5 hours will usually suffice.

After completion of the reaction, the desired compound may be collected from the reaction mixture by conventional means. For example, one suitable recovery technique comprises: distilling the solvent from the reaction mixture under reduced pressure; and then freeze-drying the residue, to obtain the desired compound. The desired compound thus obtained can be further purified, if necessary, by conventional means such as recrystallization, or the various chromatography techniques, such as column chromatography.

Preparation of a carboxylic acid ester derivative can be carried out by subjecting the lactone compound of formula (II) to ordinary solvolytic treatment.

For example, the compound of formula (II) may be contacted with an alcohol, such as methanol, ethanol, propanol or isopropanol, in the presence of an acid catalyst, such as: an inorganic acid, e.g. hydrochloric acid or sulfuric acid; a Lewis acid, such as boron trifluoride; or an acidic ion exchange resin. The reaction is preferably effected in the presence of a suitable inert organic solvent. There is no particular restriction on the nature of the solvent to be employed, provided that it has no adverse effect on the reaction or on the reagents involved. Examples of suitable solvents include: aromatic hydrocarbons, such as benzene, ethers, such as diethyl ether; and halogenated hydrocarbons, preferably halogenated aliphatic hydrocarbons, such as chloroform. Of these, we prefer to use an excess of the alcohol employed as a reagent as the solvent. The reaction can take place over a wide range of temperatures, and the precise reaction temperature is not critical to the invention. In general, we find it convenient to carry out the reaction with heating, e.g. at a temperature from about 50° C. to the boiling point of the reaction medium. The time required for the reaction may also vary widely, depending on many factors, notably the reaction temperature an the nature of the reagents. However, provided that the reaction is effected under the preferred conditions outlined above, a period of several hours will usually suffice.

After completion of the reaction, the desired compound may be collected from the reaction mixture by conventional means. For example, when an ion exchange resin is used as the catalyst, the desired compound can be obtained by filtering the reaction mixture and then removing the solvent from the filtrate; whereas, when an inorganic acid or a Lewis acid is used, it can be obtained by distillation of the solvent after neutralization, extraction with a suitable solvent and distillation of the solvent. The desired compound thus obtained can be further purified, if necessary, by conventional means such as recrystallization, or the various chromatography techniques, such as column chromatography.

Furthermore, the resulting compound can be further subjected to, for example, salt formation or esterification by conventional chemical means, as desired, to collect it easily.

These methods are all well known, and can be illustrated, for example, as follows:

The carboxylic acid of formula (I) can be obtained by adjusting a solution of the metal salt of the carboxylic acid to a pH value of 4 or less, preferably a pH value of from 3 to 4. The nature of the acids which may be employed in the reaction is not particularly critical to the process, provided that they do not affect the desired compound, and organic or mineral acids can be employed. For example, trifluoroacetic acid, hydrochloric acid or sulfuric acid are preferably used.

The carboxylic thus obtained can be extracted, washed, dehydrated or subjected to any other conventional procedures before it is used in any subsequent reaction.

An amine salt of the carboxylic acid of formula (I) can be obtained by contacting an amine with the carboxylic acid obtained above in an aqueous solvent. There is no particular restriction on the nature of the solvent to be employed, provided that it has no adverse effect on the reaction or on the reagents involved. Examples of suitable aqueous solvents include: water; or a mixture of water and an organic solvent e.g. an alcohols (such as methanol or ethanol), an ether (such as tetrahydrofuran) or a nitrile (such as acetonitrile); aqueous acetone is preferred. The reaction is preferably conducted at a pH value of from 7 to 8.5. The reaction can take place over a wide range of temperatures, and the precise reaction temperature is not critical to the invention. In general, we find it convenient to carry out the reaction at a temperature not higher than room temperature, particularly at a temperature from 5 to 10° C. The reaction will normally go instantaneously to completion. Alternatively, the same compound can be obtained, for example, by dissolving a metal salt of the carboxylic acid, obtained as described above, in an aqueous solvent, and then adding the desired amine salt of a mineral acid (e.g. the hydrochloride) thereto under the conditions described above to effect a salt exchange reaction.

An amino acid salt of the carboxylic acid of formula (I) can be obtained by contacting an amino acid with the carboxylic acid in an aqueous solvent. There is no particular restriction on the nature of the solvent to be employed, provided that it has no adverse effect on the reaction or on the reagents involved. Examples of suitable solvents include: water; and mixtures of water with an organic solvent, e.g. an alcohol (such as methanol or ethanol) or an ether (such as tetrahydrofuran). The reaction can take place over a wide range of temperatures, and the precise reaction temperature is not critical to the invention. In general, we find it convenient to carry out the reaction wit heating, e.g. at a temperature from about 50 to 60° C.

An alkyl ester of the carboxylic acid of formula (I) can alternatively be obtained by contacting the carboxylic acid obtained above with a diazoalkane. The reaction is usually conducted using an ether solution of the diazoalkane. Alternatively, the ester can be obtained by contacting the metal salt of the carboxylic acid obtained as described above with an alkyl halide. Both reactions are preferably effected in solution. There is no particular restriction on the nature of the solvent to be employed, provided that it has no adverse effect on the reaction or on the reagents involved. Examples of suitable solvents include: fatty acid amides, especially dialkylformamides, such as dimethylformamide; ethers, such as tetrahydrofuran; sulfoxides, such as dimethyl sulfoxide; and ketones, such as acetone.

All of these reactions can take place over a wide range of temperatures, and the precise reaction temperature is not critical to the invention. In general, we find it convenient to carry out the reactions at about room temperature, although they can be conducted with heating, if desired, depending on the nature of the reaction system.

The desired compound thus obtained can be collected, separated and purified using any suitable combination of conventional techniques, e.g. adsorption using various carriers such as activated carbon or silica gel; ion exchange chromatography; gel filtration using a Sephadex (trade mark) column; or extraction using an organic solvent, such as diethyl ether, ethyl acetate or chloroform.

In particular, separation of isomers can be achieved using the above-mentioned separation and purification methods in any suitable order and combination.

An alternative route for the preparation of the compound of formula (VI) from the compound of formula (V) comprises subjecting the compound of formula (VO successively to epoxidization, diolization and oxidation. These reactions are illustrated by the following Reaction Scheme B:

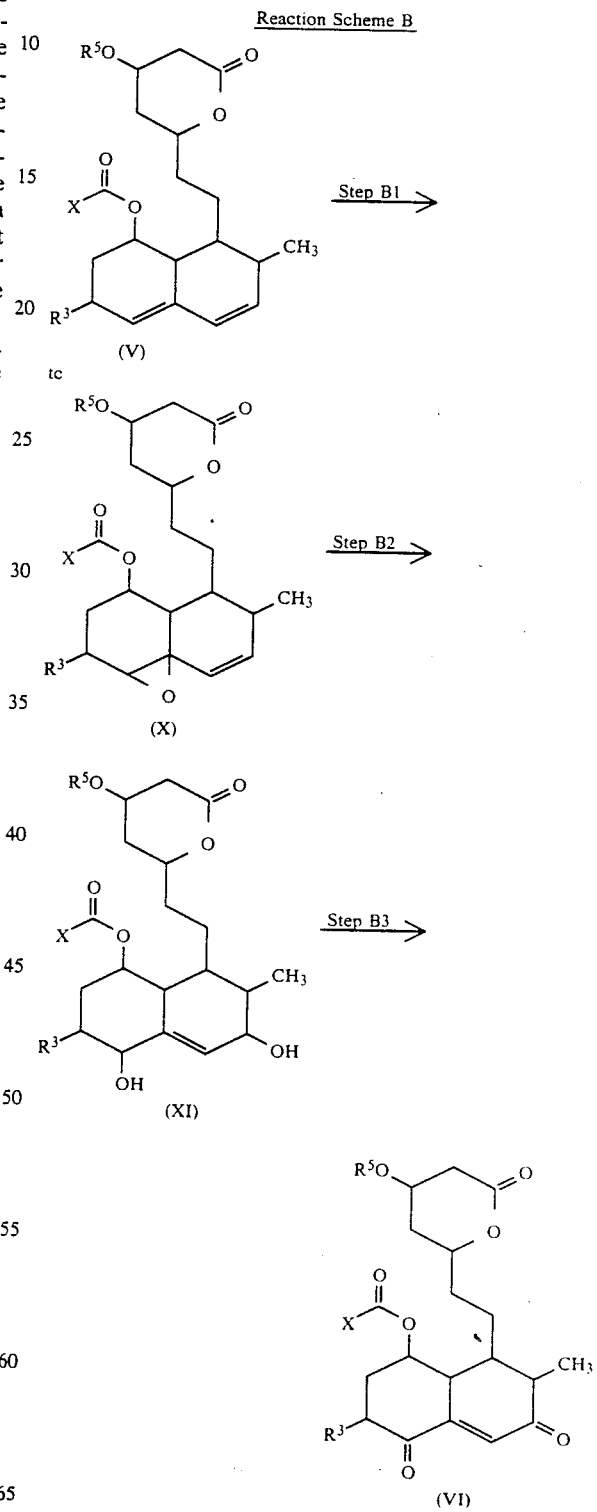

In the above formulae, $R^3$, $R^5$ and X are as defined above.

In Step B1, the compound of formula (V) is epoxidized by reacting it with an organic peracid, preferably in the presence of a solvent, to give the epoxy compound of formula (X). Organic peracids which can be employed in the reaction include, for example, peracetic acid, perbenzoic acid, m-chloroperbenzoic acid and peroxyphthalic acid, preferably m-chloroperbenzoic acid. The reaction is preferably conducted in the presence of a solvent. There is no particular restriction on the nature of the solvent to be employed, provided that it has no adverse effect on the reaction or on the reagents involved. Examples of suitable solvents include: aromatic hydrocarbons, such as benzene or toluene; halogenated hydrocarbons, preferably halogenated aliphatic hydrocarbons, such as methylene chloride or chloroform; and esters of organic acids, such as ethyl acetate. The reaction can take place over a wide range of temperatures, and the precise reaction temperature is no critical to the invention. In general, we find it convenient to carry out the reaction at a temperature from $-20$ to $50°$ C., preferably from $0°$ C. to room temperature. The time required for the reaction may also vary widely, depending on many factors, notably the reaction temperature and the nature of the reagents. However, provided that the reaction is effected under the preferred conditions outlined above, a period of from 1 to 10 hours, preferably 3 to 6 hours will usually suffice.

In Step B2, the epoxy compound of formula (X) is converted into a dihydroxy compound of formula (XI). THis conversion may be achieved by contacting the epoxy compound of formula (X) obtained as described above with an aqueous solution of an acid (e.g. 1% v/v aqueous hydrochloric acid or sulfuric acid) after completion of the epoxidization reaction of Step B1, without isolation from the reaction mixture. The compound of formula (XI) may then be isolated from the reaction mixture by contacting it with an aqueous solution of sodium bicarbonate and then distilling off the solvent from the reaction mixture.

In Step B3, the dihydroxy compound of formula (XI) is converted into the compound of formula (VI) by oxidizing the dihydroxy compound of formula (XI). The reaction is conducted under the same conditions as those described above in relation to Step A3.

Alternatively and preferably, the reaction is conducted in the presence of a solvent using as the oxidizing agent: an active organic halogen compound, such as N-bromoacetamide, N-chlorosuccinimide or N-bromophthalimide; or other conventional oxidizing agent systems, such as dimethyl sulfoxide-dicyclohexylcarbodiimide, dimethyl sulfoxide-oxalyl chloride, dimethyl sulfoxide-trifluoroacetic anhydride or dimethyl sulfoxide-pyridine-sulfuric anhydride. An acid catalyst, such as phosphoric acid or trifluoroacetic acid, may be employed when dimethyl sulfoxidedicyclohexylcarbodiimide is used; whereas a base catalyst such as a tertiary alkylamine, e.g. trimethylamine, may be employed when dimethyl sulfoxide-oxalyl chloride, dimethyl sulfoxide-pyridine-sulfuric anhydride is used. The reaction is preferably conducted in the presence of a solvent. There is no particular restriction on the nature of the solvent to be employed, provided that it has no adverse effect on the reaction or on the reagents involved. Examples of suitable solvents include: aqueous organic solvents, especially aqueous alcohols (such as aqueous t-butanol), aqueous ketones (such as aqueous acetone) and aqueous organic amines (such as aqueous pyridine) when an active organic halogen compound is used. When dimethyl sulfoxidedicyclohexylcarbodiimide, dimethyl sulfoxide-oxalyl chloride, dimethyl sulfoxide-trifluoroacetic anhydride or dimethyl sulfoxide-pyridine-sulfuric anhydride is employed, suitable solvents include: sulfoxides, such as dimethyl sulfoxide; aromatic hydrocarbons, such as benzene or toluene; and halogenated hydrocarbons, preferably halogenated aliphatic hydrocarbons, such as methylene chloride or chloroform. The reaction can take place over a wide range of temperatures, and the precise reaction temperature is not critical to the invention. In general, however, the preferred reaction temperature will depend on the type of oxidizing agent employed in the reaction. For example, in the case of dimethyl sulfoxide-oxalyl chloride or dimethyl sulfoxidetrifluoroacetic anhydride, the reaction temperature is preferably from $-70$ to $40°$ C., more preferably from $-50°$ C. to room temperature. When reagents other than these mentioned above are used, the reaction temperature is preferably from 0 to $50°$ C., more preferably from 10 to $30°$ C. The time required for the reaction may also vary widely, depending on many factors, notably the reaction temperature an the nature of the reagents. However, provided that the reaction is effected under the preferred conditions outlined above, a period of from 10 minutes to 6 hours will usually suffice.

After completion of the reaction, the desired compound may be collected from the reaction mixture by conventional means. For example, one suitable recovery technique comprises: adding a water-immiscible organic solvent to the reaction mixture to effect extraction of the desired compound; washing the extract with water; and then distilling off the solvent from the extract to give the desired compound. The desired compound thus obtained can be further purified, if necessary, by conventional means such as recrystallization, reprecipitation, or the various chromatography techniques, such as column chromatography.

The compounds of the present invention act to inhibit the synthesis of cholesterol, and thereby reduce the level of lipids in the blood. They can, therefore, be utilized in therapy, for example, as a hypolipemic agent or as an arteriosclerosis prophylactic.

These compounds can be administered orally or parenterally, for example, in the form of capsules, tablets, injections, or other conventional dosage forms. The dosage of such compound will depend on the age, condition and body weight, of the patient, as well as on the nature and severity of the symptoms, but we would normally suggest a dosage for an adult human patient of from 0.5 mg to 500 mg per day, which can be administered in a single dose or in divided doses, preferably in divided doses, e.g. in 2 to 4 doses daily. However, it can be used in an amount above this range, as necessary.

The compounds of the invention can be, and preferably are, administered in conventional pharmaceutical formulations in admixture with one or more conventional excipients, carriers or diluents, as are well known for use with compounds having this type of activity.

The invention is further illustrated by the following Examples, which illustrate the preparation of compounds of the present invention. The subsequent Preparations illustrate the preparation of certain of the starting materials used in the preparation of the compounds of the invention.

In the following Example, the compound referred to as "the dioxo compound " is 16-t-butyldimethylsilyloxy-1-(2-methylbutyryl)-3,4-dihydro-4,6-dioxoiso- ML-236A lactone. The preparation and properties of this compound are described in Example 1(i) of European Patent Specification No. 76 601, where it is referred to by the alternative name "16-t-butyldimethylsilyloxy-3,4-dihydro-4,6-dioxoIsoML-236B lactone". The description of European Patent Specification No. 76 601 is hereby incorporated by reference.

EXAMPLE 1(a)

1-(2-Methylbutyryl)-3,4-dihydro-6-oxo-4-benzyloxyiminoiso-ML-236A lactone (Compound No. 1)

15 g (28 mM) of the dioxo compound were dissolved in 150 ml of ethanol, and 4.48 g (28 mM) of O-benzylhydroxylamine hydrochloride were added to the resulting solution. 2.76 g (33.6 mM) of anhydrous sodium acetate were then added in small portions, whilst stirring and ice-cooling. The reaction mixture was then stirred for 2 hours, after which water was added to it, and it was then extracted with ethyl acetate. The extract was washed with water and dried over anhydrous sodium sulfate, and then the solvent was removed by distillation under reduced pressure from the extract, to yield 18.6 g of a residue. The whole of this residue was purified by fractionation by silica gel flash chromatography (using a 3 : 2 by volume mixture of diethyl ether and hexane as eluent), to yield 11 g of 16-t-butyldimethylsilyloxy-1-(2-methylbutyryl)-3,4-dihydro-6-oxo-4-benzyloxyiminoiso-ML-236A lactone.

2.74 g of the 16-t-butyldimethylsilyloxy-1-(2-methylbutyryl)-3,4-dihydro-6-oxo-4-benzyloxyiminoiso ML-236A lactone (obtained as described above) were then dissolved in 28 ml of a hydrofluoric acid/acetonitrile solution (a solution comprising 5 ml of a 50% w/v aqueous hydrofluoric acid solution dissolved in 95 ml of acetonitrile), and the resulting solution was stirred at room temperature for 1 hour. At the end of this time, the reaction mixture was ice-cooled and then neutralized by the addition of a saturated aqueous solution of sodium bicarbonate. The solvent was then distilled from the reaction mixture under reduced pressure, and the resulting residue was then extracted with ethyl acetate. The extract was washed with water and dried over anhydrous sodium sulfate, after which the solvent was removed from the extract by distillation under reduced pressure. The resulting residue was purified by silica gel flash chromatography (using a 4 : 1 by volume mixture of ethyl acetate and hexane as eluent), to afford 1.46 g of the title compound as a colorless foam.

Nuclear Magnetic Resonance Spectrum (CDC$\lambda_3$, 270 MHz) δppm:
7.36 (5H);
6.54 (1H, doublet);
5.47 (1H, singlet);
5.20 (2H, quartet);
4.66 (1H, multiplet);
4.37 (1H, broad singlet);
3.17 (1H, multiplet);
Infrared Absorption Spectrum (CHC$\lambda_3$) $v_{max}$cm$^{-1}$: 3450, 1725, 1660.

EXAMPLE 1(b)

Sodium 1-(2-methylbutyryl)-3,4-dihydro-6-oxo-4-benzyloxyiminoiso-ML-236A carboxylate 525 mg of 1-(2-methylbutyryl)-3,4-dihydro-6-oxo-4-benzyloxyiminoiso-ML-236A-lactone [obtained as described in Example 1(a)] were dissolved in 10 ml of ethanol, and then 10 ml (1 equivalent) of a 0.1N aqueous sodium hydroxide solution were added thereto. The resulting mixture was then stirred at room temperature for 2 hours. At the end of this time, the ethanol was removed from the reaction mixture by distillation under reduced pressure, and then the resulting residue was freeze-dried, to yield 530 mg of the title compound as a light brown, hydroscopic powder.

EXAMPLE 1(c)

Benzyl 1-(2-methylbutyryl)-3,4-dihydro-6-oxo-4-benzyloxyiminoiso-ML-236A carboxylate 280 mg of sodium 1-(2-methylbutyryl)-3,4-dihydro-6-oxo-4-benzyloxyiminoiso-ML-236A carboxylate [obtained as described in Example 1(b)] were dissolved in 5 ml of dimethylformamide, and then 120 mg (1.4 equivalents) of benzyl bromide were added to the resulting solution. The resulting mixture was then stirred at room temperature for 5 hours. At the end of this time, water was added to the reaction mixture, which was then extracted with ethyl acetate. The extract was washed with water and then dried over anhydrous sodium sulfate, after which the solvent was removed from the extract by distillation under reduced pressure. The resulting residue was purified by silica gel flash chromatography (using a 15 : 85 by volume mixture of ethyl acetate and hexane as eluent), to afford 340 mg of the title compound as a pale yellow viscous material.

Nuclear Magnetic Resonance Spectrum (CDC$\lambda_3$, 270 MHz) δppm:
7.35 (10H);
6.53 (1H, doublet);
5.50 (1H, singlet);
5.20 (2H, doublet);
5.15 (2H, singlet);
4.26 (1H, multiplet);
3.79 (1H, multiplet);
3.18 (1H, multiplet).
Infrared Absorption Spectrum (liquid) $v_{max}$cm$^{-1}$: 3450, 1730, 1660, 1575.

EXAMPLE 2(a)

1-(2-Methylbutyryl)-3,4-dihydro-6-oxo-4-(4-methoxybenzyl)oxyiminoiso-ML-236A lactone (Compound No. 6)

A procedure similar to that described in Example 1(a) was repeated, except that 5.3 g (10 mM) of the dioxo compound and 1.9 g (10 mM) of O-(4-methoxybenzyl)-hydroxylamine hydrochloride were employed, to yield 1.76 g of the title compound as a pale yellow viscous material.

Nuclear Magnetic Resonance Spectrum (CDC$\lambda_3$, 270 MHz) δppm:
7.31 (2H);
6.91 (2H);
6.55 (1H, doublet);
5.48 (1H, broad singlet);
5.13 (2H, quartet);
4.63 (1H, multiplet);
4.38 (1H, multiplet);
3.81 (3H, singlet);
3.16 (1H, multiplet).
Infrared Absorption Spectrum (CHC$\lambda_3$) $v_{max}$cm$^{-1}$: 3450, 1725, 1655.

EXAMPLE 2(b)

Sodium 1-(2-methylbutyryl)-3,4-dihydro-6-oxo-4-(4-methoxybenzyl)oxyiminoiso-ML-236A carboxylate A procedure similar to that described in Example 1(b) was repeated, except that 180 mg of 1-(2-methylbutyryl)-3,4-dihydro-6-oxo-4-(4-methoxybenzyl)oxyiminoiso-ML-236A lactone [obtained as described in Example 2(a)] were employed, to yield 180 mg of the title compound, as a pale purple powder.

EXAMPLE 3(a)

1-(2-Methylbutyryl)-3,4-dihydro-6-oxo-4-(4-fluorobenzyl)oxyiminoiso-ML-236A lactone (Compound No. 129)

A procedure similar to that described in Example 1(a) was repeated, except that 530 mg (1 mM) of the dioxo compound and 180 mg (1mM) of O-(4-fluorobenzyl)-hydroxylamine hydrochloride were employed, to yield 220 mg of the title compound as a colorless foam.

Nuclear Magnetic Resonance Spectrum (CDC$\lambda_3$, 270 MHz) $\delta$ppm:
7.0–7.3 (4H);
6.52 (1H, doublet);
5.46 (1H, broad singlet);
5.15 (3H, quartet);
4.63 (1H, multiplet);
4.38 (1H, multiplet);
3.14 (1H, multiplet).

EXAMPLE 3(b)

Sodium 1-(2-methylbutyryl)-3,4-dihydro-6-oxo-4-(4-fluorobenzyl)oxyiminoiso-ML-236A carboxylate A procedure similar to that described in Example 1(b) was repeated, except that 6 mg of 1-(2-methylbutyryl)-3,4-dihydro-3,4-dihydro-6-oxo-4-(4-fluorobenzyl)oxyiminoiso-ML-236A lactone [obtained as described in Example 3(a)] were employed, to yield 57 mg of the title compound as a light brown powder.

EXAMPLE 4(a)

1-(2-Methylbutyryl)-3,4-dihydro-6-oxo-4-(4-nitrobenzyl)-oxyiminoiso-ML-236A lactone (Compound No. 15)

A procedure similar to that described in Example 1(a) was repeated, except that 530 mg (1 mM) of the dioxo compound and 210 mg (1 mM) of O-(4-nitrobenzyl)-hydroxylamine hydrochloride were employed, to yield 115 mg of the title compound as a pale yellow foam.

Nuclear Magnetic Resonance Spectrum (CDC$\lambda_3$, 270 MHz) $\delta$ppm:
7.3–8.4 (4H);
6.58 (1H, doublet);
5.48 (1H, broad singlet);
5.30 (2H, singlet);
4.64 (1H, multiplet);
4.38 (1H, multiplet);
3.18 (1H, multiplet).

Infrared Absorption Spectrum (CHC$\lambda_3$) $\nu_{max}$cm$^{-1}$: 3400, 1725, 1650, 1530.

EXAMPLE 4(b)

Sodium 1-(2-methylbutyryl)-3,4-dihydro-6-oxo-4-(4-nitrobenzyl)oxyiminoiso-ML-236A carboxylate A procedure similar to that described in Example 1(b) was repeated, except that 80 mg of 1-(2-methylbutyryl)-3,4-dihydro-6-oxo-4-(4-nitrobenzyl) oxyiminoiso-ML-236A lactone [obtained as described in Example 4(a)] were employed, to yield 80 mg of the title compound as a light red powder.

EXAMPLE 5(a)

1-(2-Methylbutyryl)-3,4-dihydro-6-oxo-4-(3-trifluoromethylbenzyl)oxyiminoiso-ML-236A lactone (Compound No. 119)

A procedure similar to that described in Example 1(a) was repeated, except that 530 mg (1 mM) of the dioxo compound and 230 mg (1 mM) of O-(3-trifluorobenzyl)-hydroxylamine hydrochloride were employed, to yield 410 mg of the title compound as a colorless foam.

Nuclear Magnetic Resonance Spectrum (CDC$\lambda_3$, 270 MHz) $\delta$ppm:
7.5–7.7 (4H);
6.51 (1H, doublet);
5.48 (1H, broad singlet);
5.24 (2H, singlet);
4.63 (1H, multiplet);
4.38 (1H, multiplet);
3.14 (1H, multiplet).

Infrared Absorption Spectrum (CHC$\lambda_3$) $\nu_{max}$cm$^{-1}$: 3450, 1725, 1660.

EXAMPLE 5(b)

Sodium 1-(2-methylbutyryl)-3,4-dihydro-6-oxo-4-(3-trifluoromethylbenzyl)oxyiminoiso-ML-236A carboxylate A procedure similar to that described in Example 1(b) was repeated, except that 240 mg of 1-(2-methylbutyryl)-3,4-dihydro-6-oxo-4-(3-trifluoro methylbenzyl)-oxyiminoiso-ML-236A lactone [obtained as described in Example 5(a)] were employed, to yield 240 mg of the title compound as a colorless powder.

EXAMPLE 6(a)

1-(2-Methylbutyryl)-3,4-dihydro-6-oxo-4-(2-hydroxymethylbenzyl)oxyiminoiso-ML-236A lactone (Compound No. 11)

A procedure similar to that described in Example 1(a) was repeated, except that 5.3 g (10 mM) of the dioxo compound and 1.9 g (10 mM) of O-(2-hydroxymethylbenzyl)hydroxylamine hydrochloride were employed, to yield 3.7 g of the title compound as a pale yellow, viscous material.

Nuclear Magnetic Resonance Spectrum (CDC$\lambda_3$, 270 MHz) $\delta$ppm:
7.4 (4H, multiplet);
6.48 (1H, doublet);
5.46 (1H, broad singlet);
5.31 (2H, singlet);
4.76 (2H, singlet);
4.63 (1H, multiplet);
4.38 (1H, multiplet);
3.12 (1H, multiplet).

Infrared Absorption Spectrum (CHCλ₃) $\nu_{max}$cm⁻¹: 3500, 1720, 1665.

EXAMPLE 6(b)

Sodium 1(2-methylbutyryl)-3,4-dihydro-6-oxo-4-(2-hydroxymethylbenzyl)oxyiminoiso-ML-236A carboxylate A procedure similar to that described in Example 1(a) was repeated, except that 1.0 g of 1-(2-methylbutyryl)-3,4-dihydro-6-oxo-4-(2-hydroxymethyl benzyl)-oxyiminoiso-ML-236A lactone [obtained as described in Example 6(a)] was employed, to yield 980 mg of the title compound as a colorless powder.

EXAMPLE 7(a)

1-(2-Methylbutyryl)-3,4-dihydro-6-oxo-4-(3-hydroxybenzyl)oxyiminoiso-ML-236A lactone (Compound No. 5)

A procedure similar to that described in Example 1(a) was repeated, except that 1.6 g (3 mM) of the dioxide compound and 535 mg (3 mM) of O-(3-hydroxybenzyl)-hydroxylamine hydrochloride were employed, to yield 430 mg of the title compound as a light red foam.

Nuclear Magnetic Resonance Spectrum (CDCλ₃, 270 MHz) δppm:
6.8–7.3 (4H);
6.55 (1H, doublet);
5.46 (1H, broad singlet);
5.17 (2H, quartet);
4.65 (1H, multiplet);
4.38 (1H, multiplet);
3.15 (1H, multiplet).

Infrared Absorption Spectrum (CHCλ₃) $\nu_{max}$cm⁻¹: 3650, 3400, 1720, 1660, 1610.

EXAMPLE 8(a)

1-(2-Methylbutyryl)-3,4-dihydro-6-oxo-4-phenyloxyiminoiso-ML-236A lactone (Compound No. 16)

A procedure similar to that described in Example 1(a) was repeated, except that 530 mg (1 mM) of the dioxo compound and 145 mg (1 mM) of O-phenylhydroxylamine hydrochloride were employed, to yield 420 mg of the title compound as a colorless foam.

Nuclear Magnetic Resonance Spectrum (CDCλ₃, 270 MHz) δppm:
7.1–7.4 (5H);
6.70 (1H, doublet);
5.52 (1H, broad singlet);
4.63 (1H, multiplet);
4.30 (1H, multiplet);
3.40 (1H, multiplet).

Infrared Absorption Spectrum (CHCλ₃) $\nu_{max}$cm⁻¹: 3400, 1725, 1660, 1600.

EXAMPLE 8(b)

Sodium 1-(2-methylbutyryl)-3,4-dihydro-6-oxo-4-phenyloxyiminoiso-ML-236A carboxylate A procedure similar to that described in Example 1(b) was repeated, except that 220 mg of 1-(2-methylbutyryl)-3,4-dihydro-6-oxo-4-phenyloxyiminoiso-ML-236A carboxylate A procedure similar to that described in Example 1(b) was repeated, except that 220 mg of 1-(2-methylbutyryl)-3,4-dihydro-6-oxo-4-phenyloxyiminoiso-ML-236A lactone [obtained as described in Example 8(a)] were employed, to yield 220 mg of the title compound as a colorless powder.

EXAMPLE 9(a)

1-(2-Methylbutyryl)-3,4-dihydro-6-oxo-4-(3-phenylpropyl)-oxyiminoiso-ML-236A lactone (Compound No. 18)

A procedure similar to that described in Example 1(a) was repeated, except that 530 mg (1 mM) of the dioxo compound and 190 mg (1 mM) of O-(3-phenylpropyl)-hydroxylamine hydrochloride were employed, to yield 480 of the title compound as a light yellow, viscous material.

Nuclear Magnetic Resonance Spectrum (CDCλ₃, 270 MHz) δppm:
7.25 (5H);
6.53 (1H, doublet);
5.48 (1H, broad singlet);
4.64 (1H, multiplet);
4.38 (1H, broad singlet);
4.20 (2H, multiplet);
3.08 (1H, multiplet);

Infrared Absorption Spectrum (CHCλ₃) $\nu_{max}$cm⁻¹: 3450, 1730, 1660.

EXAMPLE 9(b)

Sodium 1-(2-methylbutyryl)-3,4-dihydro-6-oxo-4-(3-phenylpropyl)oxyiminoiso-ML-236A carboxylate A procedure similar to that described in Example 1(b) was repeated, except that 160 mg of 1-(2-methylbutyryl)-3,4-dihydro-6-oxo-4-(3-phenylpropyl) oxyiminoiso-ML-236A lactone [obtained as described in Example 9(a)] were employed, to yield 165 mg of the title compound as a colorless powder.

EXAMPLE 10(a)

1-(2-Methylbutyryl)-3,4-dihydro-6-oxo-4-(3-pyridylmethyl)oxyiminoiso-ML-236A lactone (Compound No. 37)

A procedure similar to that described in Example 1(a) was repeated, except that 1.1 g (2 mM) of the dioxo compound, 400 mg (2 mM) of O-(3-picolyl)hydroxylamine dihydrochloride and 500 mg (6 mM) of anhydrous sodium acetate were employed, to yield 680 mg of the title compound as a light yellow, viscous material.

Nuclear Magnetic Resonance Spectrum (CDCλ₃, 270 MHz) δppm:
8.62 (2H);
7.72 (1H);
7.31 (1H);
6.50 (1H, doublet);
5.48 (1H, broad singlet);
5.21 (2H, singlet);
4.63 (1H, multiplet);
4.38 (1H, multiplet);
3.15 (1H, multiplet);

Infrared Absorption Spectrum (CHCλ₃) $\nu_{max}$cm⁻¹: 3500, 1725, 1660, 1620.

EXAMPLE 10(b)

Sodium 1-(2-methylbutyryl)-3,4-dihydro-6-oxo-4-(3-pyridylmethyl)oxyiminoiso-ML-236A carboxylate A procedure similar to that described in Example 1(b) was repeated, except that 420 mg of 1-(2-methylbutyryl)-3,4-dihydro-6-oxo-4-(3-pyridyl methyl)ox- yiminoiso-ML-236A lactone [obtained as described in Example 10(a)] were employed, to yield 430 mg of the title compound as a light red powder.

EXAMPLE 11(a)

1-(2-Methylbutyryl)-3,4-dihydro-6-oxo-4-furfurylox- yiminoiso-ML-236A lactone (Compound No. 39)

A procedure similar to that described in Example 1(a) was repeated, except that 1.6 g (3 mM) of the dioxo compound and 450 mg (3 mM) of O-furfurylhydroxyla- mine hydrochloride were employed, to yield 1.42 g of the title compound as a light brown, viscous material.

Nuclear Magnetic Resonance Spectrum (CDC$\lambda_3$, 270 MHz) $\delta$ppm:
4.73 (1H);
6.41 (2H);
6.53 (1H, doublet);
5.47 (1H, broad singlet);
5.12 (2H, quartet);
4.64 (1H, multiplet);
4.40 (1H, multiplet);
3.61 (1H, multiplet).

Infrared Absorption Spectrum (CHC$\lambda_3$) $\nu_{max}$cm$^{-1}$: 3450, 1725, 1650.

EXAMPLE 11(b)

Sodium 1-(2-methylbutyryl)-3,4-dihydro-6-oxo-4-furfurylox- yiminoiso-ML-236A carboxylate A procedure similar to that described in Example 1(b) was repeated, except that 450 mg of 1-(2-methyl- butyryl)-3,4-dihydro-6-oxo-4-furfuryloxyiminoiso-ML- 236A lactone [obtained as described in Example 11(a)] were employed, to yield 450 mg of the title compound as a light brown powder.

EXAMPLE 11(c)

Benzyl 1-(2-methylbutyryl)-3,4-dihydro-6-oxo-4-furfurylox- yiminoiso-ML-236A carboxylate A procedure similar to that described in Example 1(c) was repeated, except that 550 mg of sodium 1-(2- methylbutyryl)-3,4-dihydro-6-oxo-4-furfurylox- yiminoiso-ML-236A carboxylate [obtained as described in Example 11(b)] and 240 mg of benzyl bromide were employed, to yield 590 mg of the title compound as a light brown, viscous material.

Nuclear Magnetic Resonance Spectrum (CDC$\lambda_3$, 270 MHz) $\delta$ppm:
7.45 (1H);
6.42 (2H);
7.35 (5H);
6.54 (1H, doublet);
5.48 (1H. broad singlet);
5.20 (2H, singlet);
5.12 (2H, quartet);
4.28 (1H, multiplet);
3.75 (1H, multiplet);
3.45 (1H, multiplet).

Infrared Absorption Spectrum (liquid) $\nu_{max}$cm$^{-1}$: 3450, 1730, 1660.

EXAMPLE 11(d)

Ethyl 1-(2-methylbutyryl)-3,4-dihydro-6-oxo-4-furfurylox- yiminoiso-ML-236A carboxylate 320 mg of sodium 1-(2-methylbutyryl)-3,4-dihydro-6- oxo-4-furfuryloxyiminoiso-ML-236A carboxylate [ob- tained as described in Example 11(b)] were dissolved in 5 ml of dimethylformamide, and 200 mg of ethyl iodide were added to the resulting solution. The resulting mix- ture was then stirred at room temperature for 6 hours. At the end of this time, water was added to the resulting reaction mixture, after which the mixture was extracted with ethyl acetate. The extract thus obtained was washed with water and dried over anhydrous sodium sulfate, after which the solvent was removed from the extract by distillation under reduced pressure. The re- sulting residue was purified by silica gel flash chroma- tography (using a 1 : 1 by volume mixture of ethyl acetate and hexane as eluent), to afford 310 mg of the title compound as a colorless, viscous material.

Nuclear Magnetic Resonance Spectrum (CDC$\lambda_3$, 270 MHz) $\delta$ppm:
7.43 (1H);
6.42 (1H);
6.38 (1H);
6.52 (1H, doublet);
5.50 (1H, broad singlet);
5.12 (2H, quartet);
4.27 (1H, multiplet);
4.17 (2H, quartet);
3.83 (1H, multiplet);
3.14 (1H, multiplet).

Infrared Absorption Spectrum (liquid) $\nu_{max}$cm$^{-1}$: 3500, 1720, 1660.

EXAMPLE 11(e)

1-(2-Methylbutyryl)-3,4-dihydro-6-oxo-4-furfurylox- yiminoiso-ML-236A carboxylic acid dicyclohexylamine salt 280 mg of sodium 1-(2-methylbutyryl)-3,4-dihydro-6- oxo-4-furfuryloxyiminoiso-ML-236A carboxylate [ob- tained as described in Example 11(b)] were dissolved in 5 ml of water, and sufficient 10% w/v aqueous sulfuric acid was added to the resulting solution to make the solution acidic. The solution was then extracted with ethyl acetate. The extract obtained was washed with a saturated aqueous solution of sodium chloride and dried over anhydrous sodium sulfate. The solvent was then removed from the extract by distillation under reduced pressure, to yield 243 mg (0.46 mM) of 1-(2-methyl- butyryl)-3,4-dihydro-6-oxo-4-furfuryloxyiminoiso-ML- 236A carboxylic acid as a viscous material.

The whole of this 1-(2-methylbutyryl)-3,4-dihydro-6- oxo-4-furfuryloxyiminoiso-ML-236A carboxylic acid was immediately dissolved in 1 ml of ethyl acetate, and 83 mg (0.46 mM) of dicyclohexylamine were added to the resulting solution, after which the solvent was re- moved by distillation under reduced pressure. Diethyl ether was added to the resulting residue to precipitate crystals, which were filtered off and washed with more diethyl ether. The resulting crystals were recrystallized from a mixture of hexane and ethanol, to afford 230 mg of the title compound as light yellow prisms having a decomposition point of 145 to 146° C.

Elemental analysis:
Calculated for $C_{40}H_{62}N_2O_9$:

C, 67.20%; H, 8.74%; N, 3.92%.
Found: C, 66.89%; H, 8.71%; N, 3.92%.

EXAMPLE 12(a)

-(2-Methylbutyryl)-3,4-dihydro-6-oxo-4-(2-tetrahydrofurylmethyl)oxyiminoiso-ML-236A lactone (Compound No. 45)

A procedure similar to that described in Example 1(a) was repeated, except that 530 mg (1mM) of the dioxo compound and 155 mg (1 mM) of O-(2-tetrahydrofurylmethyl)hydroxylamine hydrochloride were employed, to yield 410 mg of the title compound as a colorless, viscous material.

Nuclear Magnetic Resonance Spectrum (CDC$\lambda_3$, 270 MHz) δppm:
 6.52 (1H, broad singlet);
 5.48 (1H, broad singlet);
 4.66 (1H, multiplet);
 4.38 (1H, multiplet);
 4.20 (2H, multiplet);
 3.8 (2H, multiplet);
 3.18 (1H, multiplet);

Infrared Absorption Spectrum (CHC$\lambda_3$) $\nu_{max}$cm$^{-1}$: 3450, 1730, 1660.

EXAMPLE 12(b)

Sodium 1-(2-methylbutyryl)-3,4-dihydro-6-oxo-4-(2-tetrahydrofurylmethyl)oxyiminoiso-ML-236A carboxylate A procedure similar to that described in Example 1(b) was repeated, except that 210 mg of 1-(2-methylbutyryl)-3,4-dihydro-6-oxo-4-(2-tetrahydro furylmethyl)-oxyiminoiso-ML-236A lactone [obtained as described in Example 12(a)] were employed, to yield 215 mg of the title compound as a colorless powder.

EXAMPLE 13(a)

1-(2-Methylbutyryl)-3,4-dihydro-6-oxo-4-(2-tetrahydropyranylmethyl)oxyiminoiso-ML-236A lactone (Compound No. 47)

A procedure similar to that described in Example 1(a) was repeated, except that 530 ; mg (1 mM) of the dioxo compound and 170 mg (1mM) of O-(2-tetrahydropyranylmethyl)hydroxylamine hydrochloride were employed, to yield 380 mg of the title compound as a colorless, viscous material.

Nuclear Magnetic Resonance Spectrum (CDC$\lambda_3$, 270 MHz) δppm:
 6.52 (1H, doublet);
 5.48 (1H, broad singlet);
 4.64 (1H, multiplet);
 4.38 (1H, multiplet);
 4.0-4.2 (3H, multiplet);
 3.65 (1H, multiplet);
 3.40 (1H, multiplet);
 3.20 (1H, multiplet);

Infrared Absorption Spectrum (liquid) $\nu_{max}$cm$^{-1}$: 3450, 1730, 1660.

EXAMPLE 13(b)

Sodium 1-(2-methylbutyryl)-3,4-dihydro-6-oxo-4-(2-tetrahydropyranylmethyl)oxyiminoiso-ML-236A carboxylate A procedure similar to that described in Example 1(b) was repeated, except that 200 mg of 1-(2-methylbutyryl)-3,4-dihydro-6-oxo-4-(2-tetrahydro pyranylmethyl)-oxyiminoiso-ML-236A lactone [obtained as described in Example 13(a)] were employed, to yield 200 mg of the title compound as a colorless powder.

EXAMPLE 14(a)

1-(2-Methylbutyryl)-3,4-dihydro-6-oxo-4-cyclohexylmethyloxyiminoiso-ML-236A lactone (Compound No. 60)

A procedure similar to that described in Example 1(a) was repeated, except that 3.2 g (6 mM) of the dioxo compound and 1.0 g (6 mM) of O-(cyclohexylmethyl)-hydroxylamine hydrochloride were employed, to yield 2.8 g of the title compound as a colorless, viscous material.

Nuclear Magnetic Resonance Spectrum (CDC$\lambda_3$, 270 MHz) δppm:
 6.54 (1H, doublet);
 5.46 (1H, broad singlet);
 4.60 (1H, multiplet);
 4.29 (1H, multiplet);
 4.00 (2H, multiplet);
 3.14 (1H, multiplet).

Infrared Absorption Spectrum (CHC$\lambda_3$) $\nu_{max}$cm$^{-1}$: 3450, 1725, 1660.

EXAMPLE 14(b)

Sodium 1-(2-methylbutyryl)-3,4-dihydro-6-oxo-4-cyclohexylmethyloxyiminoiso-ML-236A carboxylate A procedure similar to that described in Example 1(b) was repeated, except that 1.4 g of 1-(2-methylbutyryl)-3,4-dihydro-6-oxo-4-cyclohexylmethyloxy iminoiso-ML-236A lactone [obtained as described in Example 14(a)] were employed, to yield 1.45 g of the title compound as a colorless powder.

EXAMPLE 15(a)

1-(2-Methylbutyryl)-3,4-dihydro-6-oxo-4-(cis-4-hydroxycyclohexylmethyl)oxyiminoiso-ML-236A lactone (Compound No. 61)

A procedure similar to that described in Example 1(a) was repeated, except that 1.6 g (3 mM) of the dioxo compound and 550 mg (3 mM) of O-(cis-4-hydroxycyclohexylmethyl)hydroxylamine hydrochloride were employed, to yield 1.32 g of the title compound as a colorless, viscous material.

Nuclear Magnetic Resonance Spectrum (CDC$\lambda_3$, 270 MHz) δppm:
 6.53 (1H, doublet);
 5.48 (1H, broad singlet);
 4.64 (1H, multiplet);
 4.39 (1H, multiplet);
 4.07 (2H, doublet);
 4.03 (1H, multiplet);
 3.16 (1H, multiplet);

INfrared Absorption Spectrum (CHC$\lambda_3$) $\nu_{max}$cm$^{-1}$: 3450, 1725, 1665.

EXAMPLE 15(b)

Sodium 1-(2-methylbutyryl)-3,4-dihydro-6-oxo-4-(cis-4-hydroxycyclohexylmethyl)oxyiminoiso-ML-236A carboxylate A procedure similar to that described in Example 1(b) was repeated, except that 320 mg of 1-(2-methylbutyryl)-3,4-dihydro-6-oxo-4-(cis-4-hydroxycyclohexylmethyl)oxyiminoiso-ML-236A-lactone [obtained as described in Example 15(a)] were employed, to yield 330 mg of the title compound as a colorless powder.

EXAMPLE 15(c)

Benzyl 1-(2-methylbutyryl)-3,4-dihydro-6-oxo-4-(cis-4-hydroxycyclohexylmethyl)oxyiminoiso-ML-236A carboxylate A procedure similar to that described in Example 1(c) was repeated, except that 200 mg of sodium 1-(2-methylbutyryl)-3,4-dihydro-6-oxo-4-(cis-4-hydroxycyclohexylmethyl)oxyiminoiso-ML-236A carboxylate [obtained as described in Example 15(b)] and 82 mg of benzyl bromide were employed, to yield 210 mg of the title compound as a light yellow, viscous material.

Nuclear Magnetic Resonance Spectrum (CDC$\lambda_3$, 270 MHz) δppm:
7.35 (5H);
6.52 (1H, doublet);
5.51 (1H, broad singlet);
5.15 (2H, singlet);
4.28 (1H, multiplet);
4.03 (3H, multiplet);
3.80 (1H, multiplet);
3.13 (1H, multiplet).

Infrared Absorption Spectrum (liquid) $v_{max}$cm$^{-1}$: 3500, 1730, 1660.

EXAMPLE 16(a)

1-(2-Methylbutyryl)-3,4-dihydro-6-oxo-4-(1,3-dioxan-5-yl methyl)oxyiminoiso-ML-236A lactone (Compound No. 54)

A procedure similar to that described in Example 1(a) was repeated, except that 530 mg (1 mM) of the dioxo compound and 170 mg (1 mM) of O-(1,3-dioxan-5-ylmethyl)hydroxylamine hydrochloride were employed, to yield 380 mg of the title compound as a colorless, viscous material.

Nuclear Magnetic Resonance Spectrum (CDC$\lambda_3$, 270 MHz) δppm:
6.50 (1H, doublet);
5.48 (1H, broad singlet);
4.85 (2H, quartet);
4.66 (1H, multiplet);
4.38 (1H, multiplet);
4.25 (2H, doublet);
4.02 (2H, multiplet);
3.75 (2H, multiplet);
3.14 (1H, multiplet).

Infrared Absorption Spectrum (liquid) $v_{max}$cm$^{-1}$: 3450, 1725, 1660.

EXAMPLE 16(b)

Sodium 1-(2-methylbutyryl)-3,4-dihydro-6-oxo-4-(1,3-dioxan-5-ylmethyl)oxyiminoiso-ML-236A carboxylate A procedure similar to that described in Example 1(b) was repeated, except that 220 mg of 1-(2-methylbutyryl)-3,4-dihydro-6-oxo-4-(1,3-dioxan-5-ylmethyl)oxyiminoiso-ML-236A lactone [obtained as described in Example 16(a) were employed, to yield 220 mg of the title compound as a colorless powder.

EXAMPLE 17(a)

1-(2-Methylbutyryl)-3,4-dihydro-6-oxo-4-(3-methyl-2-butenyl)oxyiminoiso-ML-236A lactone (Compound No. 64)

A procedure similar to that described in Example 1(a) was repeated, except that 1.1 g (2 mM) of the dioxo compound and 280 mg (2 mM) of O-(3-methyl-2-butenyl)-hydroxylamine hydrochloride were employed, to yield 780 mg of the title compound as a colorless, viscous material.

Nuclear Magnetic Resonance Spectrum (CDC$\lambda_3$, 270 MHz) δppm:
6.54 (1H, doublet);
5.47 (1H, broad singlet);
5.43 (1H, triplet);
4.68 (2H, doublet);
4.64 (1H, multiplet);
4.38 (1H, multiplet);
3.15 (1H, multiplet).

Infrared Absorption Spectrum (liquid) $v_{max}$cm$^{-1}$: 3450, 1725, 1660.

EXAMPLE 17(b)

Sodium 1-(2-methylbutyryl)-3,4-dihydro-6-oxo-4-(3-methyl-2-butenyl)oxyiminoiso-ML-236A carboxylate A procedure similar to that described in Example 1(b) was repeated, except that 280 mg of 1-(2-methylbutyryl)-3,4-dihydro-6-oxo-4-(3-methyl-2-butenyl)oxyiminoiso-ML-236A lactone [obtained as described in Example 17(a)] were employed, to yield 290 mg of the title compound as a colorless powder.

EXAMPLE 18(a)

1-(2-Methylbutyryl)-3,4-dihydro-6-oxo-4-(4-hydroxy-3-methyl-2-butenyl)oxyiminoiso-ML-236A lactone (Compound No. 65)

A procedure similar to that described in Example 1(a) was repeated, except that 530 mg (1mM) of the dioxo compound and 160 mg (1mM) of O-(4-hydroxy-3-methyl-2-butenyl)hydroxylamine hydrochloride were employed, to yield 410 mg of the title compound as a light yellow, viscous material.

Nuclear Magnetic Resonance Spectrum (CDC$\lambda_3$, 270 MHz) δppm:
6.53 (1H, doublet);
5.71 (1H, triplet);
5.48 (1H, broad singlet);
4.76 (2H, doublet);
4.66 (1H, multiplet);
4.38 (1H, broad singlet);
4.08 (2H, singlet);
3.15 (1H, multiplet);

Infrared Absorption Spectrum (liquid) $v_{max}$cm$^{-1}$: 3550, 1730, 1660.

EXAMPLE 18(b)

Sodium 1-(2-methylbutyryl)-3,4-dihydro-6-oxo-4-(4-hydroxy-3-methyl-2-butenyl)oxyiminoiso-ML -236A carboxylate A procedure similar to that described in Example 1(b) was repeated, except that 200 mg of 1-(2-methylbutyryl)-3,4-dihydro-6-oxo-4-(4-hydroxy--3-methyl-2-butenyl)oxyiminoiso-ML-236A lactone [obtained as described in Example 18(a)] were employed, to yield 210 mg of the title compound as a colorless, hygroscopic powder.

EXAMPLE 19(a)

1-(2-Methylbutyryl)-3,4-dihydro-6-oxo-4-(2-hydroxy-2-phenylethyl)oxyiminoiso-ML-236A lactone (Compound No. 22)

A procedure similar to that described in Example 1(a) was repeated, except that 530 mg (1 mM) of the dioxo compound and 190 mg (1 mM) of O-(2-hydroxy-2-phenylethyl)hydroxylamine hydrochloride were employed, to yield 280 mg of the title compound as a light yellow, viscous material.

Nuclear Magnetic Resonance Spectrum (CDC$\lambda_3$, 270 MHz) δppm:
7.40 (5H);
6.52 (1H, doublet);
5.49 (1H, broad singlet);
5.09 (1H, multiplet);
4.64 (1H, multiplet);
4.38 (1H, broad singlet);
4.29 (1H, multiplet);
3.20 (1H, multiplet).

Infrared Absorption Spectrum (CHC$\lambda_3$) $\nu_{max}$cm$^{-1}$: 3500, 1725, 1660.

EXAMPLE 20(a)

1-(2-Methylbutyryl)-3,4-dihydro-6-oxo-4-(1-naphthylmethyl)oxyiminoiso-ML-236A lactone (Compound No. 34)

A procedure similar to that described in Example 1(a) was repeated, except that 530 mg (1 mM) of the dioxo compound and 210 mg (1 mM) of O-(1-naphthylmethyl)hydroxylamine hydrochloride were employed, to yield 430 mg of the title compound as a light brown foam.

Nuclear Magnetic Resonance Spectrum (CDC$\lambda_3$, 270 MHz) δppm:
7.4–8.1 (7H);
6.58 (1H, doublet);
5.66 (2H, quartet);
5.45 (1H, singlet);
4.62 (1H, multiplet);
4.37 (1H, multiplet);
3.12 (1H, multiplet).

Infrared Absorption Spectrum (CHC$\lambda_3$) $\nu_{max}$cm$^{-1}$: 3450, 1720, 1660, 1590.

EXAMPLE 21(a)

1-(2-Methylbutyryl)-3,4-dihydro-6-oxo-4-(4-methylbenzyl)oxyiminoiso-ML-236A lactone (COmpound No. 123)

A procedure similar to that described in Example 1(a) was repeated, except that 3.30 g (6.2 mM) of the dioxo compound and 1.18 g (6.8 mM) of O-(4-methylbenzyl)hydroxylamine hydrochloride were employed, to yield 1.0 g of the title compound as a colorless foam.

Nuclear Magnetic Resonance Spectrum (CDC$\lambda_3$, 270 MHz) δppm:
7.28 (2H, doublet);
7.17 (2H, doublet);
6.54 (1H, doublet);
5.47 (1H, broad singlet);
5.16 (2H, quartet);
4.65 (1H, multiplet);
4.39 (1H, multiplet);
3.16 (1H, multiplet);
2.35 (3H, singlet).

Elemental analysis:
Calculated for C$_{31}$H$_{41}$O$_7$N:
C, 68.99%; H, 7.66%; N, 2.60%.
Found: C, 68.67%; H, 7.59%; N, 2.56%.

EXAMPLE 22(a)

1-(2-Methylbutyryl)-3,4-dihydro-6-oxo-4-(2,5-dimethylbenzyl)oxyiminoiso-ML-236A lactone (Compounds No. 124)

1.1 g (2.6 mM) of 1-(2-methylbutyryl)-3,4-dihydro-4,6-dioxoiso-ML-236A lactone (prepared as described in Example 6 of U.S. Pat. No. 4,361,515, the disclosure of which is incorporated herein by reference) were dissolved in 10 ml of ethanol, and 516 mg (2.7 mM) of O-(2,5-dimethylbenzyl)hydroxylamine hydrochloride were added to the resulting solution. 320 mg (3.9 mM) of anhydrous sodium acetate were then added to the mixture, whilst ice-cooling at −20° C., and the mixture was stirred for 2 hours. At the end of this time, water was added to the reaction mixture, and the mixture was extracted with ethyl acetate. The extract was then washed with water and dried over anhydrous sodium sulfate, after which the solvent was removed by distillation under reduced pressure, to obtain 1.46 g of a residue. The residue was purified by fractionation using silica gel flash chromatography (using a 2 : 1 by volume mixture of ethyl acetate and hexane as eluent), to yield 450 mg of the title compound as a colorless foam.

Nuclear Magnetic Resonance Spectrum (CDC$\lambda_3$, 270 MHz) δppm:
7.0–7.2 (3H);
6.55 (1H, doublet);
5.48 (1H, broad singlet);
5.20 (2H, quartet);
4.64 (1H, multiplet);
4.40 (1H, multiplet);
3.15 (1H, multiplet);
2.33 (3H, singlet).

Elemental analysis:
Calculated for C$_{32}$H$_{43}$O$_7$N:
C, 69.42%; H, 7.83%; N, 2.53%.
Found: C, 69.21%; H, 7.79%; N, 2.37%.

EXAMPLE 23(a)

1-(2-Methylbutyryl)-3,4-dihydro-6-oxo-4-[2-(1-hydroxy-1-methylethyl)benzyl]oxyiminoiso-ML-236A lactone (Compound No. 125)

A procedure similar to that described in Example 22(a) was repeated, except that 1.0 g (2.4 mM) of the desilylated dioxo compound and 517 mg (2.4 mM) of O-[2-(1-hydroxy-1-methylethyl)benzyl]hydroxylamine hydrochloride were employed, to yield 640 mg of the title compound as a colorless foam.

Nuclear Magnetic Resonance Spectrum (CDC$\lambda_3$, 270 MHz) δppm:
7.25–7.45 (4H);
6.50 (1H, doublet);
5.63 (1H, multiplet);
5.48 (2H, quartet);
4.63 (1H, multiplet);
4.37 (1H, multiplet);
3.15 (1H, multiplet);
1.67 (3H, singlet);
1.65 (3H, singlet).

Elemental analysis:

Calculated for $C_{33}H_{45}O_8N$:
C, 67.90%; H, 7.77%; N, 2.40%.
Found: C, 67.59%; H, 7.52%; N, 2.16%.

EXAMPLE 24(a)

1-(2-Methylbutyryl)-3,4-dihydro-6-oxo-4-(2-ethoxybenzyl)oxyiminoiso-ML-236A lactone (Compound No. 126)

A procedure similar to that described in Example 22(a) was repeated, except that 1.0 g (2.4 mM) of the desilylated dioxo compound and 490 mg (2.4 mM) of O-(2-ethoxybenzyl)hydroxylamine hydrochloride were employed, to yield 560 mg of the title compound as a light yellow foam.

Nuclear Magnetic Resonance Spectrum (CDC$\lambda_3$, 270 MHz) δppm:
6.8–7.4 (4H);
6.56 (1H, doublet);
5.48 (1H, broad singlet);
5.30 (2H, singlet);
4.64 (1H, multiplet);
4.38 (1H, multiplet);
4.07 (2H, quartet);
3.20 (1H, multiplet).
Elemental analysis:
Calculated for $C_{32}H_{43}O_8N$:
C, 67.47%; H, 7.61%; N, 2.46%.
Found: C, 67.21%; H, 7.50%; N, 2.27%.

EXAMPLE 25(a)

1-(2-Methylbutyryl)-3,4-dihydro-6-oxo-4-(4-butoxybenzyl)oxyiminoiso-ML-236A lactone (Compound No. 127)

A procedure similar to that described in Example 1(a) was repeated, except that 4.0 g (7.5 mM) of the dioxo compound and 1.74 g (7.5 mM) of O-(4-butoxybenzyl)hydroxylamine hydrochloride were employed, to yield 2.4 g of the title compound as a colorless foam.

Nuclear Magnetic REsonance Spectrum (CDC$\lambda_3$, 270 MHz) δppm:
7.31 (2H, doublet);
6.90 (2H, doublet);
6.55 (1H, doublet);
5.47 (1H, broad singlet);
5.12 (2H, quartet);
4.66 (1H, multiplet);
4.38 (1H, multiplet);
3.96 (2H, triplet);
3.14 (1H, multiplet).
Elemental analysis:
Calculated for $C_{34}H_{47}O_8N$:
C, 68.32%; H, 7.93%; N, 2.34%.
Found: C, 68.10%; H, 7.91%; N, 2.36%.

EXAMPLE 26(a)

1-(2-Methylbutyryl)-3,4-dihydro-6-oxo-4-(5-isoxazolylmethyl)oxyiminoiso-ML-236A lactone (Compound No. 128)

A procedure similar to that described in Example 22(a) was repeated, except that 1.0 g (2.4 mM) of the desilylated dioxo compound and 360 mg (2.4 mM) of O-(5-isoxazolylmethyl)hydroxylamine hydrochloride were reacted together, after which the reaction produce was purified by fractionation using a Lobar column (LiChroprep RP-18 size B, solvent: a 6 : 4 by volume mixture of acetonitrile and water), to yield 640 mg of the title compound as a light yellow foam.

Nuclear Magnetic Resonance Spectrum (CDC$\lambda_3$, 270 MHz) δppm:
8.24 (1H, doublet);
6.48 (1H, doublet);
6.32 (1H, doublet);
5.48 (1H, broad singlet);
5.28 (2H, singlet);
4.65 (1H, multiplet);
4.38 (1H, multiplet);
3.15 (1H, multiplet).
Elemental analysis:
Calculated for $C_{27}H_{36}N_2O_8$:
C, 62.78%; H, 7.02%; N, 5.42%.
Found: C, 62.50%; H, 7.06%; N, 5.11%.

EXAMPLE 27(a)

1-(2-Methylbutyryl)-3,4-dihydro-6-oxo-4-(2-morpholinoethyl)oxyiminoiso-ML-236A lactone (Compound No. 122)

A procedure similar to that described in Example 1(a) was repeated, except that 2.65 g (4.96 mM) of the dioxo compound and 1.3 g (5.9 mM) of O-(2-morpholinoethyl)hydroxylamine dihydrochloride were reacted together, after which the reaction product was purified by fractionation by silica gel flash chromatography (using a 3 : 1 by volume mixture of ethyl acetate and ethanol as eluent), to yield 1.06 g of the title compound as a colorless foam.

Nuclear Magnetic Resonance Spectrum (CDC$\lambda_3$, 270 MHz) δppm:
6.53 (1H, doublet);
5.48 (1H, broad singlet);
4.65 (1H, multiplet);
4.3–4.5 (3H, multiplet);
3.74 (4H, multiplet);
3.13 (1H, multiplet);
Elemental analysis:
Calculated for $C_{29}H_{44}O_8N_2$:
C, 63.48%; H, 8.08%; N, 5.11%.
Found: C, 63.22%; H, 7.97%; N, 5.05%.

EXAMPLES 21(b) TO 27(b)

A procedure similar to that described in Example 1(b) was repeated, except that in each case one of the lactone compounds of Examples 21(a) to 27(a), respectively, was employed in a solution of one equivalent of aqueous 0.1N sodium hydroxide solution dissolved in ethanol, to yield the corresponding sodium carboxylates, as follows:

EXAMPLE 21(b)

170 mg of sodium 1-(2-methylbutyryl)-3,4-dihydro-6-oxo-4-(4-methylbenzyl)oxyiminoiso-ML-236A carboxylate were obtained, as a colorless powder, from 180 mg of 1-(2-methylbutyryl)-3,4-dihydro-6-oxo-4-(4-methylbenzyl)oxyiminoiso-ML-236A lactone.

EXAMPLE 22(b)

100 mg of sodium 1-(2-methylbutyryl)-3,4-dihydro-6-4-(2,5-dimethylbenzyl)oxyiminoiso-ML-236A carboxylate were obtained, as a colorless powder, from 100 mg of 1- (2-methylbutyryl)-3,4-dihydro-6-oxo-4-(2,5-dimethylbenzyl)oxyiminoiso-ML-236A lactone.

EXAMPLE 23(b)

110 mg of sodium 1-(2-methylbutyryl)-3,4-dihydro-6-oxo-4-[2(1-hydroxy-1-methylethyl) benzyl]oxyiminoiso-ML-236A carboxylate were obtained, as a pale purple powder, from 110 mg of 1-(2-methylbutyryl)-3,4-dihydro-6-4-[2-(1-hydroxy-1-methylethyl)benzyl]oxyiminoiso-ML-236A lactone.

EXAMPLE 24(b)

125 mg of sodium 1-(2-methylbutyryl)-3,4-dihydro-6-oxo-4-(4-butoxybenzyl)oxyiminoiso-ML-236A carboxylate were obtained, as a pale purple powder, from 160 mg of 1-(b 2-methylbutyryl)-3,4-dihydro-6-oxo-4-(4-butoxybenzyl)oxyiminoiso-ML-236A lactone.

EXAMPLE 26(b)

110 mg of sodium 1-(2-methylbutyryl)-3,4-dihydro-6-oxo-4-(5-isoxazolylmethyl)oxyiminoiso-ML-236 A carboxylate were obtained, as a colorless powder, from 110 mg of 1-(2-methylbutyryl)-3,4-dihydro-6-oxo-4-(5-isoxazolylmethyl)oxyiminoiso-ML-236A lactone.

EXAMPLE 27(b)

565 mg of sodium 1-(b 2-methylbutyryl)-3,4-dihydro-6-oxo-4-(2-morpholinoethyl)oxyiminoiso-ML-236A carboxylate were obtained, as a colorless powder, from 550 mg of 1-(2-methylbutyryl)-3,4-dihydro-6-oxo-4-(2-morpholinoethyl)oxyiminoiso-ML-236A lactone.

PREPARATION 1

44.6 mg of sodium 3-hydroxy-ML-236B carboxylate (a compound having the above general formula (III) wherein R represents a hydroxyl group; which is identical to the compound described in Japanese Patent Publication No. 13699/1986 as the "M-4 Na salt") were introduced into a 2 liter flask, and 600 ml of a 1/3N aqueous solution of sodium hydroxide were added thereto. The resulting mixture was heated under reflux for 3 hours, after which it was cooled to room temperature to obtain a solution containing sodium 3-hydroxy-ML-236A carboxylate, whose physical properties are as follows:

1) Nuclear Magnetic Resonance Spectrum ($D_2O$, 270 MHz) δppm:
 0.69 (3H, doublet);
 3.65 (1H, multiplet);
 3.93 (1H, multiplet);
 4.22 (1H, multiplet);
 4.34 (1H, multiplet);
 5.33 (1H, broad singlet);
 5.85 (2H, multiplet).

2) Elemental analysis:
Calculated for $C_{18}H_{27}O_6Na\ H_2O$:
C, 56.83%; H, 7.68%.
Found: C, 57.02%; H, 7.64%.

The solution containing sodium 3-hydroxy-ML-236A carboxylate (obtained as described above) was adjusted to a pH value of 3.0 by the addition of 6N aqueous hydrochloric acid and saturated with sodium chloride. It was then extracted three times with ethyl acetate (1.5 liters twice, 1.0 liter once). The extracts were combined and washed with 300 ml of a saturated aqueous solution of sodium chloride and then dried over anhydrous sodium sulfate to obtain a solution containing 3-hydroxy-ML-236A-carboxylic acid, whose physical properties are as follows:

1) High-performance liquid chromatography Retention time: 5.81 minutes under the following conditions:

| Column: | NovaPak C 18 (available from Waters), having an inner diameter of 8 mm and a length of 10 cm |
|---|---|
| Movable phase: | 18% v/v acetonitrile/0.2% v/v triethylamine-phosphate buffer solution (pH 3.3) |
| Flow rate: | 2 ml/minute |
| Detector: | UV 238 nm. |

The solution containing 3-hydroxy-ML-236A carboxylic acid (obtained as described above) was concentrated at 50° C. by evaporation under reduced pressure to a volume of about 2liters, and 2.0 ml of trifluoroacetic acid were added to the concentrated solution. The resulting mixture was heated at 50 to 60° C. for about 2 hours. At the end of this time, 1 liter of ethylacetate was added to the reaction mixture. The resulting mixture was washed in turn with a 10% w/v aqueous solution of sodium bicarbonate (400 ml once, 200 ml once) and with a saturated aqueous solution of sodium chloride (200 ml twice) and dried over anhydrous sodium sulfate. The solvent was then removed from the reaction mixture by distillation under reduced pressure, to yield 18 g of crude crystals. These crude crystals were then recrystallized from a small amount of acetone to afford 11.7 g of 3-hydroxy-ML-236A-lactone as colorless amorphous crystals, melting at 158–161° C. and having the following physical properties:

1) Mass analysis:
m/e=286 ($M-H_2O$), 268 ($M-2H_2O$)

2) Elemental analysis:
Calculated for $C_{18}H_{26}O_5$:
C, 67.06%; H, 8.13%.
Found C, 66.89%; H, 7.95%.

3) Infrared Absorption Spectrum (Nujol - trade mark)
$\nu_{max}cm^{-1}$:
3430, 3330, 3220, 1730.

4) $^1H$ Nuclear Magnetic Resonance Spectrum [$(CD_3)_2CO+CD_3OD$, 90 MHz] δppm:
 0.9 (3H, doublet);
 2.65 (2H, doublet);
 4.2–4.9 (4H, multiplet);
 5.55 (1H, multiplet);
 5.9 (2H, multiplet).

5) $^{13}C$ Nuclear Magnetic Resonance Spectrum ($CD_3OD$, 22.5 MHz) δppm:
14.0, 63.15, 65.44, 66.89, 78.10, 127.35, 128.94, 135.89, 136.03, 173.44

6) Thin layer chromatography
Rf value: 0.27
Adsorbent: silica gel plate No. 5719 (available from Merck & Co., Inc.)
Developing solvent: benzene/acetone/acetic acid=50:50:3 by volume

BIOLOGICAL ACTIVITY

The compounds of the present invention have a marked ability to reduce the levels of serum cholesterol. Specifically, the biosynthesis of chlolesterol in an enzyme system or a culture cell system separated from an experimental animal is inhibited through competition with the rate limiting enzyme of 3-hydroxy-3-methyl-glutaryl-CoA reductase. This suggests that the compounds will exhibit a powerful serum cholesterol reducing effect when employed in the treatment of humans and other animals. The determination of the inhibitory activity of the compounds was made using the method of Kuroda et al ["Biochimica et Biophysica Acta" Vol. 486, pp. 70-81 (1977)] which is a modification of the known method of D. J. Shapiro et al ["Analytical Biochemistry" Vol. 31, pp. 383-390 (1969)] with some improvements.

We repeated the experiment using the following known compounds from European Patent Specification No. 76 601, which were selected as being the best and most representative of the compounds disclosed in that prior art:

Compound A: Sodium 1-(2-methylbutyryl)-3,4-dihydro-6-4-hydroxyiminoiso-ML-236A carboxylate
Compound B: Sodium 1-(2-methylbutyryl)-3,4-dihydro-6-4-hydroxyiminoiso-ML-236A carboxylate The results are shown in Table 2, in which $IC_{50}$ is the concentration to achieve 50 % inhibition of 3-hydroxy-3-methyl-glutaryl CoA reductase (nM).

TABLE 2

| Test Compound | $IC_{50}$ |
| --- | --- |
| Compound of Example 1(b) | 18.5 |
| Compound of Example 1(c) | 33.1 |
| Compound of Example 3b | 26.5 |
| Compound of Example 4b | 21.0 |
| Compound of Example 6b | 18.4 |
| Compound of Example 10b | 31.4 |
| Compound of Example 11b | 36.0 |
| Compound of Example 17b | 21.3 |
| Compound A | 35.7 |
| Compound B | 39.5 |

It can be seen from Table 2 that the compounds of the present invention exhibit superior activity to that of the two known compounds in terms of the concentration required to achieving a 50% inhibition of 3-hydroxy-3-methylglutaryl-CoA reductase.

We claim:

1. A compound of formula (I):

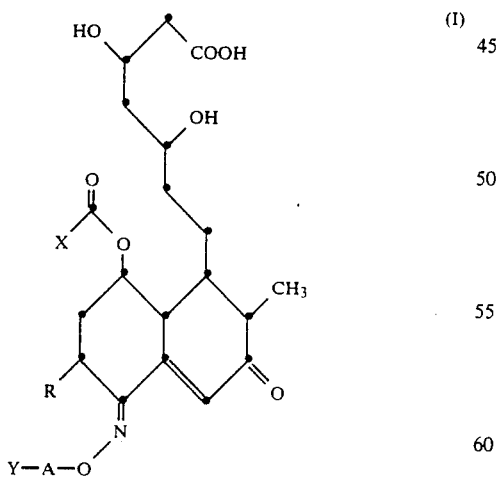

in which:
R represents a hydrogen atom, a methyl group or a hydroxy group;
X represents a $C_1$-$C_{10}$ alkyl group, a $C_3$-$C_{10}$ alkenyl group, a $C_3$-$C_{10}$ cycloalkyl group, a $C_6$-$C_{10}$ aryl group, or a $C_7$-$C_{12}$ aralkyl group; said alkyl and alkenyl groups being unsubstituted or having one to four substituents selected from the group consisting of substituents (a), defined below, and said cycloalkyl, aryl, and aralkyl groups being unsubstituted or having one to four substituents selected from the group consisting of substituents (b), defined below;

A represents a single bond, A $C_1$-$C_{10}$ alkylene group, a $C_3$-$C_{10}$ alkenylene group, a $C_3$-$C_{10}$ alkynylene group or a $C_5$-$C_{10}$ alkadienylene group, said alkylene, alkenylene, alkynylene and alkadienylene groups being unsubstituted or have one to three selected from the group consisting of substituents (c), defined below;

Y is

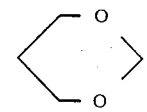

which is unsubstituted or having one to three substituents selected from the group consisting of substituents (d), defined below;

substituents (a):
halogen atoms, hydroxy groups, $C_1$-$C_4$ alkoxy groups, $C_2$-$C_5$ aliphatic carboxylic acyloxy groups, amino groups, carboxy groups and protected carboxy groups;

substituents (b):
halogen atoms, hydroxy groups, $C_1$-$C_4$ alkoxy groups, $C_2$-$C_5$ aliphatic carboxylic acyloxy groups, amino groups, carboxy groups and protected carboxy groups, $C_1$-$C_5$ alkyl groups and $C_1$-$C_5$ haloalkyl groups;

substituents (c):
halogen atoms, hydroxy groups, $C_1$-$C_4$ alkoxy groups, $C_6$-$C_{14}$ aryloxy groups, $C_7$-$C_9$ aralkyloxy groups, $C_2$-$C_5$ aliphatic carboxylic acyloxy groups, $C_7$-$C_{15}$ aromatic carboxylic acyloxy groups, amino groups, $C_1$-$C_4$ alkylamino groups, dialkylamino groups in which each alkyl group is $C_1$-$C_4$, $C_6$-$C_{14}$ arylamino groups, diarylamino groups in which each aryl group is $C_6$-$C_{14}$, $C_7$-$C_9$ aralkylamino groups, diaralkylamino groups in which each aralkyl group is $C_7$-$C_9$, $C_2$-$C_5$ aliphatic carboxylic acylamino groups, $C_7$-$C_{15}$ aromatic carboxylic acylamino groups, carboxy groups and protected carboxy groups, wherein the aryl groups of said aryloxy, aralkyloxy, aromatic carboxylic acyloxy, arylamino, diarylamino, aralkylamino, diaralkylamino and aromatic carboxylic acylamino groups are unsubstituted or have one to three substituents selected from the group consisting of substituents (e), defined below;

substituents (d):
halogen atoms, hydroxy groups, $C_1$-$C_4$ alkoxy groups, $C_6$-$C_{14}$ aryloxy groups, $C_7$-$C_9$ aralkyloxy groups, $C_2$-$C_5$ aliphatic carboxylic acyloxy groups, $C_7$-$C_{15}$ aromatic carboxylic acyloxy groups, mercapto groups, $C_1$-$C_4$ alkylthio groups, $C_6$-$C_{14}$ arylthio groups, $C_7$-$C_9$ aralkylthio groups, amino groups, $C_1$-$C_4$ alkylamino groups, dialkylamino groups in which each alkyl group is $C_1$-$C_4$, $C_6$-$C_{14}$ arylamino groups, diarylamino groups in which each aryl group is $C_6$-$C_{14}$, $C_7$-$C_9$ aralkylamino groups, diaralkylamino groups in which each aralkyl group is $C_7$-$C_9$, $C_2$-$C_5$ aliphatic carboxylic acylamino groups, $C_7$-$C_{15}$ aromatic carboxylic acylamino groups, nitro groups, cyano groups, carboxy groups, protected carboxy groups, $C_1$-$C_5$ alkyl groups and $C_1$-$C_5$ alkyl groups having at least one substituent selected from the group consisting of substituents (f), defined below, wherein the aryl groups of said aryloxy, aralkyloxy, aromatic carboxylic acyloxy, arylthio, aralkylthio, arylamino, diarylamino, aralkylamino, diaralkylamino and aromatic carboxylic acylamino groups are unsubstituted or have one to three substituents selected from the group consisting of substituents (e), defined below;

substituents (e):
$C_1$-$C_4$ alkyl groups, hydroxy groups, halogen atoms, $C_1$-$C_4$ alkoxy groups, carboxy groups, protected carboxy groups and amino groups;

substituents (f):
halogen atoms, hydroxy groups and $C_2$-$C_5$ aliphatic carboxylic acyloxy groups;

wherein the protected carboxy groups in substituents (a), (b), (c) and (d) are protected by $C_1$-$C_4$ alkyl, $C_6$-$C_{10}$ aryl, $C_2$-$C_4$ alkenyl, $C_1$-$C_4$ haloalkenyl tri($C_1$-$C_4$) alkyl, or triphenylsilyl ($C_1$-$C_4$) alkyl;

or a pharmaceutically acceptable salt or ester thereof, or a corresponding ring-closed lactone.

2. The compound of claim 1, having the formula (II):

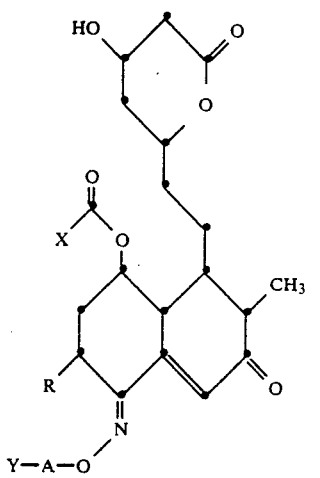

(II)

in which R, X, A and Y are as defined in claim 1.

3. The compound of claim 1, wherein the salt is the sodium salt.

4. The compound of claim 1, wherein the ester is the benzyl ester.

5. The compound of claim 1, wherein:
R represents a hydrogen atom, a methyl group or a hydroxy group;
X represents a $C_1$-$C_{10}$ alkyl group, a $C_3$-$C_{10}$ alkenyl group, a $C_3$-$C_{10}$ cycloalkyl group, a phenyl group, or a $C_7$-$C_9$ aralkyl group said alkyl and alkenyl groups are unsubstituted or have from 1 to 4 substituents selected from the group consisting of substituents (a'), defined below, and said cycloalkyl, phenyl, aralkyl and heterocyclic groups are unsubstituted or have from 1 to 4 substituents selected from the group consisting of sustituents (b), defined in claim 1;

A represents a $C_1$-$C_{10}$ alkylene group, a $C_5$-$C_{10}$ alkadienylene group, a $C_3$-$C_{10}$ alkenylene group or a $C_3$-$C_5$ alkynylene group, in which said alkylene, alkenylene, alkadienylene and alkynylene groups are unsubstituted or have 1 or 2 substituents selected from the group consisting of substituents (c'), defined below and Y is

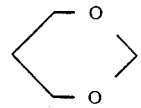

being unsubstituted or having 1 or 2 substituents selected from the group consisting of substituents (d'), defined below;

substituents (a'):
halogen atoms, hydroxy groups, $C_1$-$C_4$ alkoxy groups, $C_2$-$C_5$ aliphatic carboxylic acyloxy groups, amino groups, carboxy groups and protected carboxy groups;

substituents (c'):
halogen atoms, hydroxy groups, $C_1$-$C_4$ alkoxy groups, $C_6$-$C_{14}$ aryloxy groups, $C_2$-$C_5$ aliphatic carboxylic acyloxy groups, amino groups, mono- and di-$C_1$-$C_4$ alkyl-substituted amino groups, $C_2$-$C_5$ aliphatic carboxylic acylamino groups, $C_7$-$C_{15}$ aromatic carboxylic acylamino groups, carboxy groups and protected carboxy groups, in which the aryl groups of said aryloxy and aromatic carboxylic acylamino groups are unsubstituted or have from 1 to 3 substituents selected from the group consisting of substituents (e'), defined below;

substituents (d')
halogen atoms, hydroxy groups, $C_1$-$C_4$ alkoxy groups, $C_6$-$C_{14}$ aryloxy groups, $C_7$-$C_9$ aralkyloxy groups, $C_2$-$C_5$ aliphatic carboxylic acyloxy groups, $C_7$-$C_{15}$ aromatic carboxylic acyloxy groups, mercapto groups, $C_1$-$C_4$ alkylthio groups, amino groups, mono- and di-$C_1$-$C_4$ alkylsubstituted amino groups, $C_2$-$C_5$ aliphatic carboxylic acylamino groups, nitro groups, cyano groups, carboxy groups, protected carboxy groups, $C_1$-$C_5$ alkyl groups, $C_1$-$C_5$ haloalkyl groups, $C_1$-$C_5$ hydroxyalkyl groups and $C_1$-$C_5$ alkyl groups having a $C_2$-$C_5$ aliphatic carboxylic acyloxy substituent, in which the aryl groups of said aryloxy, aralkyloxy and aromatic carboxylic acyloxy groups are unsubstituted or have from 1 to 3 substituents selected from the group consisting of substituents (e'), defined below; and substituents (e')
$C_1$-$C_4$ alkyl groups, hydroxy groups, halogen, $C_1$-$C_4$ alkoxy groups, carboxy groups, protected carboxy groups and amino groups;

or a pharmaceutically acceptable salt or ester thereof and the corresponding ring-closed lactones.

6. The compound of claim 1, wherein:
R represents a hydrogen atom, a methyl group or a hydroxy group;
X represents a $C_1$-$C_{10}$ alkyl group, a $C_3$-$C_{10}$ alkenyl group or a $C_3$-$C_7$ cycloalkyl group, in which said alkyl and alkenyl groups are unsubstituted or have 1 or 2 substituents selected from the group consisting of substituents (a″), defined below, and said cycloalkyl groups are unsubstituted or have 1 or 2 substituents selected from the group consisting of substituents (b′), defined below;

A represents a $C_1$–$C_5$ alkylene group, a $C_3$–$C_5$ alkenylene group or a $C_5$–$C_8$ alkadienylene group, in which said alkylene, alkenylene and alkadienylene groups are unsubstituted or have 1 or 2 substituents independently selected from the group consisting of substituents (c″), defined below; and Y is

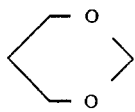

being unsubstituted or having 1 or 2 independently substituents selected from the group consisting of substituents (d″), defined below;

substituents (a″):
halogen atoms, hydroxy groups, $C_2$–$C_5$ aliphatic carboxylic acyloxy groups, carboxy groups and protected carboxy groups;

substituents (b′):
halogen atoms, hydroxy groups, $C_1$–$C_4$ alkoxy groups, $C_2$–$C_5$ aliphatic carboxylic acyloxy groups, $C_1$–$C_5$ alkyl groups and $C_1$–$C_5$ haloalkyl groups;

substituents (d″):
halogen atoms, hydroxy groups, $C_1$–$C_4$ alkoxy groups, amino groups, mono and di-$C_1$–$C_4$ alkyl-substituted amino groups and $C_2$–$C_5$ aliphatic carboxylic acylamino groups; and substituents (d″):
halogen atoms, hydroxy groups, $C_1$–$C_4$ alkoxy groups, $C_6$–$C_{14}$ aryloxy groups, $C_7$–$C_9$ aralkyloxy groups, amino groups, mono- and di-$C_1$–$C_4$ alkyl-substituted amino groups, $C_2$–$C_5$ aliphatic carboxylic acylamino groups, nitro groups, cyano groups, carboxy groups, protected carboxy groups, $C_1$–$C_5$ alkyl groups, $C_1$–$C_5$ haloalkyl groups, $C_1$–$C_5$ hydroxyalkyl groups and $C_1$–$C_5$ alkyl groups having a $C_2$–$C_5$ aliphatic carboxylic acyloxy substituent;

or a pharmaceutically acceptable salt or ester thereof and the corresponding ring-closed lactone.

7. The compound of claim 1, wherein:
R represents a hydrogen atom;
X represents a $C_1$–$C_7$ alkyl group, a $C_3$–$C_5$ alkenyl group or a $C_3$–$C_7$ cycloalkyl group, said alkyl and alkenyl groups being unsubstituted or having 1 or 2 substituents independently selected from the group consisting of substituents (a$^{iv}$), defined below, and said cycloalkyl groups being unsubstituted or having at least one substituent selected from the group consisting of substituents (b‴), defined below;

A represents a $C_1$–$C_5$ alkylene group or a $C_3$–$C_5$ alkenylene group, each of which may be unsubstituted or have 1 or 2 substituents independently selected from the group consisting of substituents (c$^{iv}$), defined below; and Y is

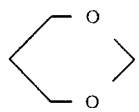

which may be unsubstituted or have 1 or 2 substituents independently selected from the group consisting of substituents (d$^{iv}$), defined below;

substituents (a$^{iv}$):
halogen atoms and carboxy groups;

substituents (b‴):
halogen atoms and $C_1$–$C_5$ haloalkyl groups;

substituents (c$^{iv}$):
hydroxy groups and $C_1$–$C_4$ alkoxy groups;

substituents (d$^{iv}$):
halogen atoms, hydroxy groups, $C_1$–$C_4$ alkoxy groups, amino groups, mono- and di-$C_1$–$C_4$ alkyl-substituted amino groups, $C_2$–$C_5$ haloalkyl groups and $C_1$–$C_5$ hydroxyalkyl groups;

or a pharmaceutically acceptable salt or ester thereof and the corresponding ring-closed lactone.

8. The compound of claim 1, wherein:
R represents a hydrogen atom;
X represents A $C_1$–$C_1$. alkyl group, a $C_3$–$C_{10}$ alkenyl group or a $C_3$–$C_{10}$ cycloalkyl group, said alkyl and alkenyl groups being unsubstituted or having at least one substituent selected from the group consisting of substituents (a‴), defined below, and said cycloalkyl groups being unsubstituted or have at least one substituent selected from the group consisting of substituents (b″), defined below;

A represents a single bond, a $C_1$–$C_{10}$ alkylene group or a $C_3$–$C_{10}$ alkenylene group, said alkylene and alkenylene groups being unsubstituted or have at least one substituent selected from the group consisting of substituents (c‴), defined below;

Y is

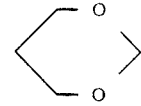

being unsubstituted or having at least one substituent selected from the group consisting of substituents (d‴), defined below;

substituents (a‴):
halogen atoms, carboxy groups and protected carboxy groups;

substituents (b″):
halogen atoms, carboxy groups, protected carboxy groups, $C_1$–$C_5$ alkyl groups and $C_1$–$C_5$ haloalkyl groups;

substituents (c‴):
halogen atoms, hydroxy groups and $C_1$–$C_4$ alkoxy groups; and substituents (d‴):
halogen atoms, hydroxy groups, $C_1$–$C_4$ alkoxy groups, amino groups, $C_1$–$C_4$ alkylamino groups, dialkylamino groups in which each alkyl group is $C_1$–$C_4$, nitro groups, carboxy groups, protected carboxy groups, $C_1$–$C_5$ alkyl groups and $C_1$–$C_5$ alkyl groups having at least one substituent selected from the group consisting of halogen atoms and hydroxy groups;

or a pharmaceutically acceptable salt or ester thereof and the corresponding ring-closed lactone.

9. The compound of claim 1, selected from the group consisting of 1-(2-methylbutyryl)-3,4-dihydro-6-oxo-4-(1,3-dioxan-5-yl-methyl)oxyiminoiso-ML-236A lactone pharmaceutically acceptable salt or ester of the corresponding free acid.

10. The compound of claim 1, which is sodium 1-(2-methylbutyryl)-3,4-dihydro-6-oxo-4-(1,3-dioxan-5-yl-methyl)oxyiminoiso-ML-236A carboxylate.

11. The compound of claim 1, wherein
X is a $C_1$-$C_{10}$ alkyl group, a $C_3$-$C_{10}$ cycloalkyl group, a $C_6$-$C_{10}$ aryl group, a $C_7$-$C_{12}$ aralkyl group, said alkyl and alkenyl groups being unsubstituted or having at least one substituent selected from the group consisting of substituent (a), and said cycloalkyl, aryl, aralkyl being unsubstituted
Y is

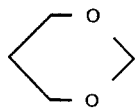

being unsubstituted or having at least one substituent selected from substituents (d).

12. A pharmaceutical composition comprising an effective amount of a compound of claim 1 for inhibiting cholesterol biosynthesis in admixture with a pharmaceutically acceptable carrier or diluent.

13. The composition of claim 12, wherein said compound has the formula (II):

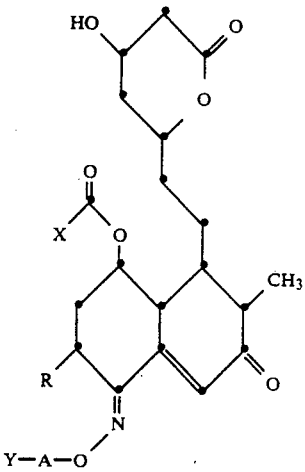

(II)

in which R, X, A and Y are as defined in claim 12.

14. The composition of claim 12, wherein:
R represents a hydrogen atom, a methyl group or a hydroxy group;
X represents a $C_1$-$C_{10}$ alkyl group, a $C_3$-$C_{10}$ alkenyl group or a $C_3$-$C_7$ cycloalkyl group, in which said alkyl and alkenyl groups are unsubstituted or have 1 or 2 substituents selected from the group consisting of substituents (a''), defined below, and said cycloalkyl groups are unsubstituted or have 1 or 2 substituents selected from the group consisting of substituents (b'), defined below;
A represents a $C_1$-$C_5$ alkylene group, a $C_3$-$C_5$ alkenylene group or a $C_5$-$C_8$ alkadienylene group, in which said alkylene, alkenylene and alkadienylene groups are unsubstituted or have 1 or 2 substituents independently selected from the group consisting of substituents (c''), defined below; and
Y is

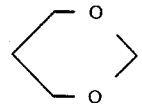

being unsubstituted or having 1 or 2 independently substituents selected from the group consisting of substituents (d''), defined below;
substituents (a''):
halogen atoms, hydroxy groups, $C_2$-$C_5$ aliphatic carboxylic acyloxy groups, carboxy groups and protected carboxy groups;
substituents (b'):
halogen atoms, hydroxy groups, $C_1$-$C_4$ alkoxy groups, $C_2$-$C_5$ aliphatic carboxylic acyloxy groups, $C_1$-$C_5$ alkyl groups and $C_1$-$C_5$ aliphatic carboxylic acylamino groups; and
substituents (d''):
halogen atoms, hydroxy groups, $C_1$-$C_4$ alkoxy groups, $C_6$-$C_{14}$ aryloxy groups, $C_7$-$C_9$ aralkyloxy groups, amino groups, mono- and di-$C_1$-$C_4$ alkyl-substituted amino groups, $C_2$-$C_5$ aliphatic carboxylic acylamino groups, nitro groups, cyano groups, carboxy groups, protected carboxy groups, $C_1$-$C_5$ alkyl groups, $C_1$-$C_5$ haloalkyl groups, hydroxyalkyl groups and $C_1$-$C_5$ alkyl groups having a $C_2$-$C_5$ aliphatic carboxylic acyloxy substituent;
pharmaceutically acceptable salt or esters thereof and the corresponding ring-closed lactone.

15. The composition of claim 12, wherein:
R represents a $C_1$-$C_7$ alkyl group, a $C_3$-$C_5$ alkenyl group or a $C_3$-$C_7$ cycloalkyl group, said alkyl and alkenyl groups being unsubstituted or having 1 or 2 substituents independently selected from the group consisting of substituents ($a^{iv}$), defined below, and said cycloalkyl groups being unsubstituted or having at least one substituent selected from the group consisting of substituents ($b'''$), defined below;
A represents a $C_1$-$C_5$ alkylene group or a $C_3$-$C_5$ alkenylene group, each of which may be unsubstituted or have 1 or 2 substituents independently selected from the group consisting of substituents ($C^{iv}$), defined below; and
Y is

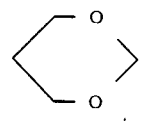

which may be unsubstituted or have 1 or 2 substituents independently selected from the group consisting of substituents ($d^{iv}$), defined below;
substituents ($a^{iv}$):
halogen atoms and carboxy groups;
substituents ($b'''$):
halogen atoms and $C_1$-$C_5$ haloalkyl groups;
substituents ($c^{iv}$):
hydroxy groups and $C_1$-$C_4$ alkoxy groups;
substituents ($d^{iv}$):

halogen atoms, hydroxy groups, C₁-C₄ alkoxy groups, amino groups, mono- and di-C₁-C₄ alkyl-substituted amino groups, C₂-C₅ aliphatic carboxylic acylamino groups, nitro groups, C₁-C₅ alkyl groups, C₁-C₅ haloalkyl groups and C₁-C₅ hydroxyalkyl groups;

or a pharmaceutically acceptable salt or ester thereof and the corresponding ring-closed lactone.

16. The composition of claim 12, wherein:

R represents a hydrogen atom;

X represents a $C_1$-$C_{10}$ alkyl group, a $C_3$-$C_{10}$ alkenyl group or a $C_3$-$C_{10}$ cycloalkyl group, said alkyl and alkenyl groups being unsubstituted or having at least one substituent selected from the group consisting of substituents (a'''), defined below, and said cycloalkyl groups being unsubstituted or having at least one substituent selected from the group consisting of substituents (b'''), defined below;

A represents a single bond, a $C_1$-$C_{10}$ alkylene group of a $C_3$-$C_{10}$ alkenylene group, said alkylene and alkenylene groups being unsubstituted or having at least one substituent selected from the group consisting of substituents (c'''), defined below;

Y is

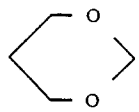

being unsubstituted or having at least one substituent selected from the group consisting of substituents (d'''), defined below;

substituents (1'''):
halogen atoms, carboxy groups and protected carboxy groups;

substituents (b'''):
halogen atoms, carboxy groups, protected carboxy groups, C₁-C₅ alkyl groups and C₁-C₅ haloalkyl groups;

substituents (c'''):
halogen atoms, hydroxy groups and C₁-C₄ alkoxy groups; and substituents (d'''):
halogen atoms, hydroxy groups, C₁-C₄ alkoxy groups, amino groups, C₁-C₄ alkylamino groups, dialkylamino groups in which each alkyl group is C₁-C₄, nitro groups, carboxy groups, protected carboxy groups, C₁-C₅ alkyl groups and C₁-C₅ alkyl groups having at least one substituent selected from the group consisting of halogen atoms and hydroxy groups;

or a pharmaceutically acceptable salt or ester thereof and the corresponding ring-closed lactone.

17. The composition of claim 12, wherein said compound is:
1-(2-methylbutyryl)-3,4-dihydro-6-oxo-4-(1,3-dioxan-5-yl-methyl)oxyiminoiso-ML-236A lactone;
or a pharmaceutically acceptable salt or ester of the corresponding free acid.

18. The composition of claim 12, wherein said compound is:
sodium 1-(2-methylbutyryl)-3,4-dihydro-6-oxo-4-(1,3-dioxan-5-ylmethyl)oxyiminoiso-ML-236A carboxylate.

19. A method of treating a mammal suffering form a disorder arising from a blood cholesterol imbalance, which comprises administering to said mammal an effective amount to inhibit cholesterol biosynthesis a compound of claim 1.

20. The method of claim 19, wherein said compound has the formula (II):

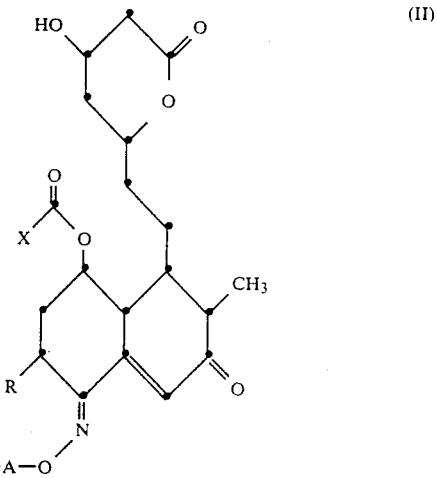

in which R, X, A and Y are as defined in claim 19.

21. The method of claim 19, wherein said compound is:
1-(2-methylbutyryl)-3,4-dihydro-6-oxo-4-(1,3-dioxan-5-yl-methyl)oxyiminoiso-ML-236A lactone;
or a pharmaceutically acceptable salt or ester of the corresponding free acid.

22. The method of claim 19, wherein said compound is:
sodium 1-(2-methylbutyryl)-3,4-dihydro-6-oxo-4-(1,3-dioxan-5-ylmethyl)oxyiminoiso-ML-236A carboxylate.

23. The pharmaceutical composition of claim 12, wherein

X is a $C_1$-$C_{10}$ alkyl group, a $C_3$-$C_{10}$ alkenyl group, a $C_3$-$C_{10}$ cycloalkyl group, a $C_6$-$C_{10}$ aryl group, a $C_7$-$C_{12}$ aralkyl group, said alkyl and alkenyl groups being unsubstituted or having at least one substituent selected from the group consisting of substituents (a), and said cycloalkyl, aryl, aralkyl being unsubstituted Y is

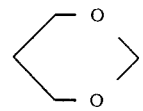

being unsubstituted or having at least one substituent selected from substituents (d).

24. The method of claim 19, wherein

X is a $C_1$-$C_{10}$ alkyl group, a $C_3$-$C_{10}$ alkenyl group, a $C_3$-$C_{10}$ cycloalkyl group, a $C_6$-$C_{10}$ aryl group, a $C_7$-$C_{12}$ aralkyl group, said alkyl and alkenyl groups being unsubstituted or having at lest one substituent selected from the group consisting of substituents (a), and said cycloalkyl, aryl, aralkyl being unsubstituted Y is

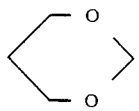

being unsubstituted or having at least one substituent selected from substituents (d).

* * * * *

UNITED STATES PATENT AND TRADEMARK OFFICE
CERTIFICATE OF CORRECTION

PATENT NO. : 4,997,848

DATED : March 5, 1991

INVENTOR(S) : KURABAYASHI et al

It is certified that error appears in the above-identified patent and that said Letters Patent is hereby corrected as shown below:

Title page, Section [56] Cited References, insert under "FOREIGN PATENT DOCUMENTS:

```
2 046 737  11/1980  Great Britain
2 073 193  10/1981  Great Britain
2 073 199  10/1981  Great Britain
2 075 013  11/1981  Great Britain
0 076 601   4/1983  European
```

Column 9, line 52, change "al" to --all--.

Column 15, line 11, before "$C_1 - C_4$", insert --the mercapto group;--.

Column 17, line 47, change "slats" to --salts--.

Column 31, lines 39-40, change "$R^3$ l represents a hydrogen atom or a methyl group; X represents a" to --$R^3$ represents a hydrogen atom or a methyl group; x represents a --.

Column 68, line 26 (claim 8), change "A" to --a--.

Column 69, line 17 (Claim 11), after "unsubstituted", insert --or having at least one substituent selected from the groups consisting of substituents (b);--.

Column 69, lines 25-26 (Claim 11), delete "or having at least one substituent selected from substituents (d)".

UNITED STATES PATENT AND TRADEMARK OFFICE
CERTIFICATE OF CORRECTION

PATENT NO. : 4,997,848
DATED : March 5, 1991
INVENTOR(S) : KURABAYASHI, et al

It is certified that error appears in the above-identified patent and that said Letters Patent is hereby corrected as shown below:

Column 72, line 42 (Claim 23), after "unsubstituted", insert --or having at least one substituent selected from the groups consisting of substituents (b)--.

Column 72, lines 50-51 (Claim 23), delete "or having at least one substituent selected from substituents (d)".

Column 72, line 58 (Claim 24), after "unsubstituted", insert --or having at least one substituent selected from the groups consisting of substituents (b)--.

Column 72, lines 66-67 (claim 24), delete "or having at least one substituent selected from substituents (d)".

Signed and Sealed this

Seventh Day of June, 1994

Attest:

BRUCE LEHMAN

Attesting Officer

Commissioner of Patents and Trademarks